(12) United States Patent
Taylor

(10) Patent No.: US 12,077,803 B2
(45) Date of Patent: *Sep. 3, 2024

(54) MICRORNAs AS BIOMARKERS FOR ENDOMETRIOSIS

(71) Applicant: YALE UNIVERSITY, New Haven, CT (US)

(72) Inventor: Hugh Taylor, Easton, CT (US)

(73) Assignee: Yale University, New Haven, CT (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/517,014

(22) Filed: Nov. 2, 2021

(65) Prior Publication Data

US 2022/0049312 A1    Feb. 17, 2022

Related U.S. Application Data

(63) Continuation of application No. 17/184,894, filed on Feb. 25, 2021, now Pat. No. 11,220,713, which is a continuation of application No. 16/329,436, filed as application No. PCT/US2017/049284 on Aug. 30, 2017, now Pat. No. 10,982,282.

(60) Provisional application No. 62/381,130, filed on Aug. 30, 2016.

(51) Int. Cl.
*C12Q 1/6883* (2018.01)
*G01N 33/53* (2006.01)
*G01N 33/68* (2006.01)

(52) U.S. Cl.
CPC ....... *C12Q 1/6883* (2013.01); *G01N 33/5308* (2013.01); *G01N 33/689* (2013.01); *C12Q 2600/112* (2013.01); *C12Q 2600/158* (2013.01); *C12Q 2600/178* (2013.01); *G01N 2800/364* (2013.01)

(58) Field of Classification Search
None
See application file for complete search history.

(56) References Cited

U.S. PATENT DOCUMENTS

| | | |
|---|---|---|
| 10,982,282 B2 | 4/2021 | Taylor |
| 11,220,713 B2 | 1/2022 | Taylor |
| 11,315,660 B2 | 4/2022 | Taylor |
| 2009/0317820 A1 | 12/2009 | Wong |
| 2012/0093936 A1 | 4/2012 | Lindenberg |
| 2014/0024590 A1 | 1/2014 | Weidhaas |
| 2014/0342937 A1 | 11/2014 | Jeanson-Leh |
| 2015/0267257 A1 | 9/2015 | Nagarkatti |
| 2016/0251718 A1 | 9/2016 | Giudice |
| 2017/0175190 A1 | 6/2017 | Taylor |
| 2018/0127828 A1* | 5/2018 | Belli .............. A61P 25/20 |
| 2019/0276893 A1 | 9/2019 | Taylor |
| 2020/0206303 A1 | 7/2020 | Bowerman |
| 2020/0321077 A1 | 10/2020 | Taylor |
| 2021/0180134 A1 | 6/2021 | Taylor |
| 2022/0049312 A1 | 2/2022 | Taylor |

FOREIGN PATENT DOCUMENTS

| | | |
|---|---|---|
| CN | 103237901 | 8/2013 |
| EP | 2924126 | 9/2015 |
| EP | 2924126 B1 | 4/2018 |
| JP | 2014513521 A | 6/2014 |
| JP | 2015504655 A | 2/2015 |
| WO | 2010056337 A2 | 5/2010 |
| WO | 2012103355 A2 | 8/2012 |
| WO | 2012112883 | 8/2012 |
| WO | 2013148151 A1 | 10/2013 |
| WO | 2015073972 A1 | 5/2015 |
| WO | 2015128671 A1 | 9/2015 |
| WO | 2015148919 | 10/2015 |
| WO | 2018044979 A1 | 3/2018 |
| WO | 2019046494 | 3/2019 |
| WO | 2020092672 | 5/2020 |
| WO | 2020223238 | 11/2020 |

OTHER PUBLICATIONS

Turchinovich et al., 2011, "Characterization of extracellular circulating microRNA." Nucleic Acids Res, 39:7223-7233.
U.S. Appl. No. 15/129,663 Examiner Interview Summary dated Nov. 20, 2020, 5 pages.
Ulivi et al., 2014, "miRNAs as non-invasive biomarkers for lung cancer diagnosis." Molecules, 19:8220-8237.
Vodolazkaia et al., "Evaluation of a panel of 28 biomarkers for the non-invasive diagnosis of endometriosis." Hum Reprod, 27: 2698-2711, Jun. 26, 2012.
Voelkerding et al. (Clinical Chemistry, 2009 vol. 55:641-658).
Wang et al., "Correlation and quantitation of microRNA aberrant expression in tissues and sera from patients with breast tumor." Gynecol Oncol, 119: 586-593, Jul. 2010.
Wang et al., "Serum miR-146a and miR-223 as potential new biomarkers for sepsis." Biochem Biophys Res Commun, 394: 184-188, Feb. 2010.
Wang et al., 2012, "Circulating MIR-125b as a marker predicting chemoresistance in breast cancer." PLoS One, 7: e34210 (8 pages).
Wang et al., 2012, "Evidence for serum miR-15a and miR-16 levels as biomarkers that distinguish sepsis from systemic inflammatory response syndrome in human subjects." Clin Chem Lab Med, 50:1423-1428.
Wang et al., 2013, "Circulating microRNAs identified in a genome-wide serum microRNA expression analysis as noninvasive biomarkers for endometriosis." J Clin Endocrinol Metab, 98:281-289.
Wang et al., 2015, "MicroRNA-125b may function as an oncogene in lung cancer cells." Mol Med Rep, 11(5):3880-3887.
Wang, et al. Analysis of Serum microRNA Profile by Solexa Sequencing in Women With Endometriosis. Reprod Sci. Oct. 2016;23(10):1359-70. doi: 10.1177/1933719116641761. Epub Jul. 13, 2016.
Weber, et al. The microRNA spectrum in 12 body fluids. Clinical chemistry 56.11 (2010): 1733-1741.

(Continued)

*Primary Examiner* — Kimberly Chong
(74) *Attorney, Agent, or Firm* — Riverside Law LLP

(57) ABSTRACT

Disclosed herein are compositions and methods useful for the diagnosis, assessment, and characterization of endometriosis in a subject in need thereof, based upon the expression level of at least one miRNA that is associated with endometriosis.

16 Claims, 11 Drawing Sheets

Specification includes a Sequence Listing.

(56) References Cited

OTHER PUBLICATIONS

Wen-Tao Wang et al, "Circulating MicroRNAs Identified in a Genome-Wide Serum MicroRNA Expression Analysis as Noninvasive Biomarkers for Endometriosis", Journal of Clinical Endocrinology & Metabolism, (Jan. 1, 2013), vol. 98, No. 1, doi:10.1210/jc.2012-2415, ISSN 0021-972X, pp. 281-289, XP055127854.
Xu et al., 2014, "Tumor-suppressing effects of miR451 in human osteosarcoma." Cell Biochem Biophys, 69(1):163-168.
Yang et al., "MicroRNA expression profiling in human ovarian cancer: miR-214 induces cell survival and cisplatin resistance by targeting PTEN." Cancer Res, 68: 425-433, Jan. 15, 2008.
Yang et al., "MicroRNA microarray identifies Let-7i as a novel biomarker and therapeutic target in human epithelial ovarian cancer." Cancer Res, 68: 10307-10314.
Zhao et al., 2006, "KRAS variation and risk of endometriosis." Molecular Human Reproduction. vol. 12, No. 11, pp. 671-676.
Zhao et al., 2012, "Circulating microRNA miR-323-3p as a biomarker of ectopic pregnancy." Clin Chem, 58:896-905.
Zhu et al., 2008, "Heme oxygenase-1 suppresses hepatitis C virus replication and increases resistance of hepatocytes to oxidant injury." Hepatology, 48: 1430-1439.
Zhu et al., 2014, Different miRNA expression profiles between human breast cancer tumors and serum. Front Genet, 5:149, 7 pages.
Afshar, et al. Changes in eutopic endometrial gene expression during the progression of experimental endometriosis in the baboon, *Papio anubis*. Biology of reproduction 88.2 (2013): 44-1.
Aitana Braza-Bols et al, "MicroRNA expression profile in endometriosis: its relation to angiogenesis and fibrinolytic factors", Human Reproduction, GB, (Mar. 6, 2014), vol. 29, No. 5, doi:10.1093/humrep/deu019, ISSN 0268-1161, pp. 978-988, XP055402965.
Akao et al., 2007, "MicroRNA-143 and- 145 in colon cancer." DNA Cell Biol, 26: 311-320.
Arroyo et al., 2011, "Argonaute2 complexes carry a population of circulating microRNAs independent of vesicles in human plasma." Proc Natl Acad Sci U S A, 108:5003-5008.
Azmy et al. (Medical Research Journal: Dec. 2012—vol. 11:pp. 1-13).
Bandiera et al., 2015, "miR-122—a key factor and therapeutic target in liver disease . . . " J Hepatol, 62:448-457.
Bell et al., 2013, "Insulin-like growth factor 2 mRNA-binding proteins (IGF2BPs): post-transcriptional drivers of cancer progression?" Cell Mol Life Sci, 70: 2657-2675.
Brest et al., "A synonymous variant in IRGM alters a binding site for miR-196 and causes deregulation of IRGM-dependent xenophagy in Crohn's disease." Nat Genet, 43: 242-245, Jan. 10, 2011.
Chang et al. BMPR1B Up-Regulation via a miRNA Binding Site Variation Defines Endometriosis Susceptibility and CA125 Levels. PLoS One 2013, 8:e80630-e80630, 10 pages.
Chen et al. MIR-125b regulates endometrial receptivity by targeting MMP26 in women undergoing IVF-ET with elevated progesterone on HCG priming day. Scientific reports 6 (2016): 25302. (12 pages).
Chen et al., 2008, "Characterization of microRNAs in serum: a novel class of biomarkers for diagnosis of cancer and other diseases." Cell Res, 18:997-1006.
Chen et al., 2014, "MicroRNA 125b suppresses the proliferation and osteogenic differentiation of human bone marrow derived mesenchymal stem cells." Mol Med Rep, 9(5):1820-1826.
Cheng, et al. Print CG, Charnock-Jones DS. Activation of mutated K-ras in donor endometrial epithelium and stroma promotes lesion growth in an intact immunocompetent murine model of endometriosis. J Pathol 224.2 (2011): 261-269.
Cho et al. Aromatase inhibitor regulates let-7 expression and let-7f-induced cell migration in endometrial cells from women with endometriosis. Fertility and sterility 106.3 (2016): 673-680.
Cho et al., 2012, "Urinary vitamin D-binding protein is elevated in patients with endometriosis." Hum Reprod, 27:515-522.
Cho et al., 2015, "Circulating microRNAs as potential biomarkers for endometriosis." Fertil Steril, 103(5):1252-1260.
Co-pending U.S. Appl. No. 17/289,882, inventor Taylor; Hugh, filed Apr. 29, 2021.
Co-pending U.S. Appl. No. 17/703,321, inventors Taylor; Hugh et al., filed Mar. 24, 2022.
Co-pending U.S. Appl. No. 17/834,762, inventors Bowerman; Heather et al., filed Jun. 7, 2022.
Co-pending U.S. Appl. No. 16/860,792, filed Apr. 28, 2020 (82 pages).
Cosar, et al. Serum microRNAs as diagnostic markers of endometriosis: a comprehensive array-based analysis. Fertil Steril. Aug. 2016;106(2):402-9. doi: 10.1016/j.fertnstert.2016.04.013. Epub May 11, 2016.
Coskun et al., 2012, "MicroRNAs in inflammatory bowel disease—pathogenesis, diagnostics and therapeutics . . . " World J Gastroenterol, 18:4629-4634.
D'Hooghe, et al. Lack of an Association between a Polymorphism in the KRAS 3' Untranslated Region (rs61764370) and Endometriosis in a Large European Case-Control Study.Gynecologic and obstetric investigation 84.6 (2019):575-582.
D'Alessandra et al., 2010, "Circulating microRNAs are new and sensitive biomarkers of myocardial infarction." Eur Heart J, 31: 2765-2773.
Dai et al., 2012, MiR-199a attenuates endometrial stromal cell invasiveness through suppression of the IKKβ/NF-κB pathway and reduced interleukin-8 expression. Mol Hum Reprod, 18: 136-145.
Dorval et al., 2013, "Circulating microRNAs in Alzheimer's disease: the search for novel biomarkers . . . " Front Mol Neurosci, 6:24 (6 pages).
EP15769372.2 Extended Search Report dated Sep. 8, 2017. (11 pages).
EP17847431.8 Extended European Search Report dated Jul. 22, 2020 (15 pages).
EP17847431.8 The Partial Supplemental European Search Report dated Apr. 8, 2020. (14 pages).
EP18852025.8 Extended Search Report dated Aug. 3, 2021.
EP20194688.6 Extended European Search Report dated Feb. 22, 2021.
Gallo et al., 2012, "The majority of microRNAs detectable in serum and saliva is concentrated in exosomes." PLoS One, 7: e30679 (5 pages).
Ghazal et al. H19 lncRNA alters stromal cell growth via IGF signaling in the endometrium of women with endometriosis. EMBO molecular medicine 7.8 (2015): 996-1003.
Giray et al., 2014, "Profiles of serum microRNAs; miR-125b-5p and miR223-3p serve as novel biomarkers for HBV-positive hepatocellular carcinoma." Mol Biol Rep, 41(7):4513-4519.
Graham et al. The expression of microRNA-451 in human endometriotic lesions is inversely related to that of macrophage migration inhibitory factor (MIF) and regulates MIF expression and modulation of epithelial cell survival. Human Reproduction 30.3 (2015): 642-652.
Grechukhina et al., 2012, "A polymorphism in a let-7 microRNA binding site of KRAS in women with endometriosis." EMBO Mol Med, 4: 206-217.
Hou et al., "The let-7 microRNA enhances heme oxygenase-1 by suppressing Bach1 and attenuates oxidant injury in human hepatocytes." Biochim Biophys Acta, 1819: 1113-1122, Jun. 2012.
Iorio et al., "MicroRNA gene expression deregulation in human breast cancer." Cancer Res, 65: 7065-7070, Aug. 15, 2005.
Jarry et al., 2014, The validity of circulating microRNAs in oncology: five years of challenges and contradictions. Mol Oncol, 8: 819-829.
Jia et al., 2013, "Plasma miR-17-5p, miR-20a and miR-22 are down-regulated in women with endometriosis." Hum Reprod, 28:322-330.
Jin et al., 2013, "Circulating microRNAs: a novel class of potential biomarkers for diagnosing and prognosing central nervous system diseases . . . " Cell Mol Neurobiol, 5:601-613.
Joshi et al. Altered expression of microRNA-451 in eutopic endometrium of baboons (*Papio anubis*) with endometriosis. Human Reproduction 30.12 (2015): 2881-2891.
Kennedy et al. (Hum Reprod., 2005 vol. 20:2698-2704).

(56) References Cited

OTHER PUBLICATIONS

Lai et al., 2014, "Modulated expression of human peripheral blood microRNAs from infancy to adulthood and its role in aging." Aging Cell, 13:679-689.

Laudanski et al., Expression of selected tumor suppressor and oncogenes in endometrium of women wiht endometriosis, Hum Reprod. Aug. 2009;24(8): 1880-90.

Lawrie et al., "Detection of elevated levels of tumour-associated microRNAs in serum of patients with diffuse large B-cell lymphoma . . . " Br J Haematol, 141: 672-675, Jan. 2, 2008.

Liu et al., 2014, "MicroRNAs as potential biomarkers for gastric cancer." World J Gastroenterol, 20:12007-12017.

Liu et al., 2016, "MicroRNA 451 inhibits neuroblastoma proliferation, invasion and migration by targeting macrophage migration inhibitory factor." Mol Med Rep, 13(3): 2253-60; doi: 10.3892/mmr. 4770.

Luong, et al. No evidence for genetic association with the let-7 microRNA-binding site or other common KRAS variants in risk of endometriosis. Human reproduction 27.12 (2012): 3616-3621.

Marsh et al., "Differential expression of microRNA species in human uterine leiomyoma versus normal myometrium . . . " Fertil Steril, 89: 1771-1776, Dec. 15, 2008.

Matamala et al., 2015, "Tumor microRNA expression profiling identifies circulating microRNAs for early breast cancer detection." Clin Chem, 61(8):1098-1106.

May et al., 2010, "Peripheral biomarkers of endometriosis: a systematic review." Hum Reprod, 16:651-674.

Medical News Today downloaded from Sputum: Definition, colors, causes, and when to see a doctor (medicalnewstoday.com on Dec. 1, 2021.

Mitchell et al., "Circulating microRNAs as stable blood-based markers for cancer detection." Proc Natl Acad Sci USA, 105: 10513-10518, May 12, 2008.

Mol, et al. "The performance of CA-125 measurement in the detection of endometriosis: a meta-analysis." Fertil Steril, 70: 1101-1108, Dec. 1998.

Mongroo et al., "IMP-1 displays cross-talk with K-Ras and modulates colon cancer cell survival through the novel proapoptotic protein CYFIP2." Cancer Res, 71: 2172-2182, Jan. 20, 2011.

Moustafa, et al. Accurate diagnosis of endometriosis using serum microRNAs. Am J Obstet Gynecol. Mar. 9, 2020. pii: S0002-9378(20)30321-5. doi: 10.1016/j.ajog.2020.02.050. [Epub ahead of print], 28 pages.

Mu, et al. Expression, regulation and function of MicroRNAs in endometriosis.Die Pharmazie—An International Journal of Pharmaceutical Sciences 71.8 (2016): 434-438.

Murri et al., 2013, "Effects of polycystic ovary syndrome (PCOS), sex hormones, and obesity on circulating miRNA-21, miRNA-27b, miRNA-103, and miRNA-155 expression." J Clin Endocrinol Metab, 98:E1835-1844.

Nagel et al., "Regulation of the adenomatous polyposis coli gene by the miR-135 family in colorectal cancer." Cancer Res, 68: 5795-5802, Jul. 15, 2008.

Nakasa et al., "Expression of microRNA-146 in rheumatoid arthritis synovial tissue." Arthritis Rheum, 58: 1284-1292, May 2008.

Naqvi et al., 2016, "Endometriosis Located Proximal to or Remote From the Uterus Differentially Affects Uterine Gene Expression." Reprod Sci, 23:186-191.

Nematian et al. Systemic inflammation induced by microRNAs: endometriosis-derived alterations in circulating microRNA 125b-5p and Let-7b-5p regulate macrophage cytokine production. The Journal of Clinical Endocrinology & Metabolism 103.1 (2017): 64-74.

Nisenblat, et al. Blood biomarkers for the non-invasive diagnosis of endometriosis. Cochrane Database Syst Rev. May 1, 2016;(5):CD012179. (654 pages).

Notice of Allowability dated Dec. 14, 2021 for U.S. Appl. No. 17/184,894 (pp. 1-2).

Notice of Allowability dated Feb. 1, 2021 for U.S. Appl. No. 16/329,436 (pp. 1-3).

Notice of Allowability dated Sep. 9, 2021 for U.S. Appl. No. 15/129,663 (pp. 1-5).

Notice of Allowance dated Jan. 27, 2021 for U.S. Appl. No. 16/329,436 (pp. 1-8).

Notice of Allowance dated Jul. 26, 2021 for U.S. Appl. No. 15/129,663 (pp. 1-5).

Notice of Allowance dated Sep. 21, 2021 for U.S. Appl. No. 17/184,894 (pp. 1-7).

Office Action (Final Rejection) dated Jun. 29, 2022 for U.S. Appl. No. 15/129,663 (pp. 1-15).

Office Action (Non-Final Rejection) dated May 23, 2023 for U.S. Appl. No. 15/129,663 (pp. 1-15).

Office Action dated Apr. 8, 2020 for U.S. Appl. No. 16/329,436 (pp. 1-19).

Office Action dated Aug. 4, 2021 for U.S. Appl. No. 17/184,894 (pp. 1-6).

Office Action dated Dec. 6, 2021 for U.S. Appl. No. 15/129,663 (pp. 1-17).

Office Action dated Jan. 15, 2020 for U.S. Appl. No. 15/129,663 (pp. 1-12).

Office Action dated Jul. 29, 2019 for U.S. Appl. No. 15/129,663 (pp. 1-11).

Office Action dated Nov. 1, 2018 for U.S. Appl. No. 15/129,663 (pp. 1-12).

Office Action dated Oct. 23, 2020 for U.S. Appl. No. 15/129,663 (pp. 1-17).

Office Action dated Oct. 27, 2020 for U.S. Appl. No. 16/329,436 (pp. 1-20).

Pan et al., "The expression profile of micro-RNA in endometrium and endometriosis and the influence of ovarian steroids on their expression." Mol Hum Reprod, 13: 797-806 (Retracted), Aug. 31, 2007.

PCT/US2015/022986 International Preliminary Report on Patentability dated Sep. 27, 2016. (10 pages).

PCT/US2015/022986 International search report with written opinion dated Aug. 10, 2015, 11 pages.

PCT/US2017/049284 International Search Report and Written Opinion dated Nov. 28, 2017. (15 pages).

PCT/US2018/048649 International Search Report dated Jan. 2, 2019. (14 pages).

Rafaella Petracco et al, "MicroRNA 135 Regulates HOXA10 Expression in Endometriosis", Journal of Clinical Endocrinology & Metabolism, (Dec. 1, 2011), vol. 96, No. 12, doi:10.1210/jc.2011-1231, ISSN 0021-972X, pp. E1925-E1933, XP055187310.

Ramon et al., "microRNAs expression in endometriosis and their relation to angiogenic factors." Hum Reprod, 26: 1082-1090, Jan. 17, 2011.

Reis et al., 2012, "Diagnostic value of serum activin A and follistatin levels in women with peritoneal, ovarian and deep infiltrating endometriosis." Hum Reprod, 27:1445-1450.

Rekker et al., 2013, "Circulating microRNA Profile throughout the menstrual cycle." PLoS One, 8: e81166, (6 pages).

Resnick et al., 2008, "The detection of differentially expressed microRNAs from the serum of ovarian cancer patients using a novel real-time PCR platform." Gynecol Oncol, 112: 55-59.

Ruan Yu et al., "[Study on microRNA expression in endometrium of luteal phase and its relationship with infertility of endometriosis]", Chung-Hua Fu Ch'an K'O Tsa Chih—Chinese Journal of Obstetricsand Gyneco, Chinese Medical Journals Publ. House, CN, (Dec. 1, 2013), vol. 48, No. 12, ISSN 0529-567X, pp. 907-910, XP008170439.

Sayed et al., 2014, "Diagnosis, Prognosis and Therapeutic Role of Circulating miRNAs in Cardiovascular Diseases." Heart Lung Cir, 23:503-510.

Schwarzenbach et al., 2014, "Clinical relevance of circulating cell-free microRNAs in cancer." Nat Rev Clin Oncol, 11:145-156.

Small et al., "Pervasive roles of microRNAs in cardiovascular biology." Nature, 469: 336-342, Jan. 20, 2011.

Sredni et al., 2011, "A Parallel Study of mRNA and microRNA Profiling of Peripheral Blood in Young Adult Women." Front Genet, 2:49 (6 pages).

Suryawanshi et al., 2013, "Plasma microRNAs as novel biomarkers for endometriosis and endometriosis-associated ovarian cancer." Clin Cancer Res, 19:1213-1224.

(56) References Cited

OTHER PUBLICATIONS

Tang et al., "MiR-135a functions as a tumor suppressor in epithelial ovarian cancer and regulates HOXA10 expression." Cell Signal, 26: 1420-1426, Mar. 2014.

Taylor, et al. Treatment of Endometriosis-Associated Pain with Elagolix, an Oral GnRH Antagonist . . . N Engl J Med. Jul. 6, 2017;377(1):28-40.

Teague et al., "MicroRNA-regulated pathways associated with endometriosis." Mol Endocrinol, 23: 265-275, Dec. 2008, 11 pages.

Teague et al., 2010, The role of microRNAs in endometriosis and associated reproductive conditions. Hum Reprod Update, 16: 142-165.

Office Action (Notice of Allowance and Fees Due (PTOL-85)) dated Jan. 18, 2024 for U.S. Appl. No. 15/129,663 (pp. 1-13).

Yang et al., 2008, "MicroRNA microarray identifies Let-7i as a novel biomarker and therapeutic target in human epithelial ovarian cancer." Cancer Res, 68: 10307-10314.

\* cited by examiner

MICRORNAs AS BIOMARKERS FOR ENDOMETRIOSIS

CROSS-REFERENCE TO RELATED APPLICATIONS

This application is a continuation of U.S. patent application Ser. No. 17/184,894, filed Feb. 25, 2021, which is a continuation of U.S. patent application Ser. No. 16/329,436, filed Feb. 28, 2019, which is a U.S. national phase application filed under 35 U.S.C. § 371 claiming benefit to PCT International Patent Application No. PCT/US2017/049284, filed on Aug. 30, 2017, which claims priority to U.S. Provisional Application No. 62/381,130, filed Aug. 30, 2016, each of which disclosures is incorporated herein by reference in its entirety.

REFERENCE TO A "SEQUENCE LISTING," A TABLE, OR A COMPUTER PROGRAM LISTING APPENDIX SUBMITTED AS AN ASCII TEXT FILE

The present application hereby incorporates by reference the entire contents of the text file named "047162-5124_02US_SequenceListing.txt" in ASCII format. The text file containing the Sequence Listing of the present application was created on Nov. 1, 2021 and is 8,613 bytes in size.

BACKGROUND

Micro RNAs (miRNAs) are a class of highly conserved small endogenous noncoding, functional RNA molecules of 19-24 nucleotides; they control the translation and stability of targeted RNAs by base-pairing to complementary sites and induce repression or degradation of messenger RNA transcripts (Bartel et al., 2009, Cell, 136:215-233). They play a pivotal role in the regulation of development and cellular homeostasis of diverse biological processes (Hassan et al., 2015, Bone, 81:746-756). They exist intracellularly as well as in the serum (Corcoran et al., 2011, Clin Chem, 57(1):18-32) and possess specific characteristics that make them promising biomarker candidates for the diagnosis of various diseases (Sayed et al., 2014, Heart Lung Cir, 23:503-510, Coskun et al., 2012, World J Gastroenterol, 18:4629-4634, Dorval et al., 2013, Front Mol Neurosci, 6:24, Jin et al., 2013, Cell Mol Neurobiol, 5:601-613, Liu et al., 2014, World J Gastroenterol, 20:12007-12017, Ulivi et al., 2014, Molecules, 19:8220-8237, Zhu et al., 2014, Front Genet, 5:149, Bandiera et al., 2015, J Hepatol, 62:448-457). Cell-free miRNAs are stably present in several body fluids, including blood serum and plasma, urine, and saliva (Chen et al., 2008, Cell Res, 18:997-1006). Serum miRNA expression is stable, reproducible, and consistent among individuals. Specific expression patterns have been identified as biomarkers for numerous diseases including cancers (Schwarzenbach et al., 2014, Nat Rev Clin Oncol, 11:145-156). miRNAs remain stable as they are released from cells to the extracellular space in membrane vesicles (Gallo et al., 2012, PLoS One, 7: e30679) or bound to protein complexes (Turchinovich et al., 2011, Nucleic Acids Res, 39:7223-7233, Arroyo et al., 2011, Proc Natl Acad Sci USA, 108: 5003-5008). Alterations in miRNA levels in blood may reflect changes during normal physiologic processes (Lai et al., 2014, Aging Cell, 13:679-689, Redni et al., 2011, Front Genet, 2:49) and have been related to several pathologic conditions, including gynecologic diseases (Zhao et al., 2012, Clin Chem, 58:896-905, Murri et al., 2013, J Clin Endocrinol Metab, 98:E1835-1844).

Endometriosis is a common gynecological disorder, affecting 10% of reproductive-aged women (Taylor et al., 2011, Reprod Sci, 18(9):814-823). It is characterized by the deposition and proliferation of the endometrial cells outside the uterine cavity (Giudice et al., 2010, N Engl J Med, 362:2389-2398, Bulun et al., 2009, N Engl J Med, 360:268-279). The major symptoms of endometriosis are pelvic pain in 50% of patients (Eskenazi et al., 1997, Obstet Gynecol Clin North Am, 24:235-258) and infertility in 40 to 50% of patients (Ozkan et al., 2008, Ann N Y Acad Sci, 1127:92-100, Moradi et al., 2014, BMC Womens Health, 14:123). Unfortunately, there are no currently available accurate serum biomarkers of this disease. Imaging techniques such as ultrasound are unreliable in the diagnosis and staging of endometriosis (Dunselman et al., 2014, Hum Reprod, 29:400-412). Definitive diagnosis of endometriosis is often made only at late stages of the disease by direct visualization of the lesions with laparascopy and confirmation of pathology. A major impediment to successful treatment of endometriosis is the failure of diagnosis at an early stage. A simple blood test for endometriosis-specific biomarkers would offer a more timely and accurate diagnosis of the disease and could lead to earlier treatment intervention. Although there have been considerable efforts to identify such biomarkers (Wang et al., 2012, Clin Chem Lab Med, 50:1423-1428, Jia et al., 2013, Hum Reprod, 28:322-330, Suryawanshi et al., 2013, Clin Cancer Res, 19:1213-1224), no clear choice for such noninvasive diagnostic tools has been identified. Serum CA-125 is elevated in some women with endometriosis, however it is not specific and has poor sensitivity and specificity. As described above, miRNAs have been carefully evaluated as biomarkers for several diseases; they hold promise for a diagnostic marker of endometriosis.

Despite the fact that endometriosis is present in 10% of all reproductive-aged women, and in 20-50% in infertile women, there is no definite diagnostic biomarker for endometriosis yet available. Imaging techniques, such as ultrasound and magnetic resonance imaging, have been shown to be unreliable in the diagnosis or staging of this disease. The direct visualization of lesions and histologic confirmation through surgical procedures are currently essential for the definitive diagnosis of endometriosis, which requires general anesthesia, developed surgical skills, procedural costs, and the risk of potential complications. Therefore, development of new noninvasive diagnostic markers for endometriosis is crucial for early diagnosis and proper treatment and management of the disease. Thus there is a need in the art for improved compositions and methods for noninvasive biomarkers of endometriosis. The present disclosure satisfies this unmet need.

SUMMARY

This disclosure provides novel methods of detecting, diagnosing, and/or prognosing endometriosis in female subjects suspected of having endometriosis, as well as novel methods of treating endometriosis. Many of the methods provided herein generally relate to detecting miRNA biomarkers in samples such as blood, serum, or saliva. As such, the methods may be used in non-invasive or minimally-invasive assays to detect endometriosis and may help many female patients avoid more invasive procedures such as biopsies of endometrial tissue. The methods may also promote early diagnosis and may promote treatment of endometriosis at an early stage, before the patient has developed more severe or serious symptoms.

In one aspect, this disclosure provides a method of diagnosing a subject suspected of having endometriosis comprising: (a) providing a saliva, sputum, urine, lymphatic fluid, synovial fluid, cerebrospinal fluid, stool, or mucus sample from the subject, wherein the saliva, sputum, urine, lymphatic fluid, synovial fluid, cerebrospinal fluid, stool, or mucus sample comprises miRNA associated with endometriosis; (b) detecting a level of the miRNA associated with endometriosis; (c) comparing the detected level of miRNA associated with endometriosis with a reference value in order to determine a relative level of miRNA associated with endometriosis in the saliva, sputum, urine, lymphatic fluid, synovial fluid, cerebrospinal fluid, stool, or mucus sample; and (d) diagnosing the subject with endometriosis based on the relative level of miRNA associated with endometriosis in the saliva, sputum, urine, lymphatic fluid, synovial fluid, cerebrospinal fluid, stool, or mucus sample, wherein the diagnosing the subject with endometriosis has a specificity or sensitivity greater than 90%.

In some embodiments, the sample is a fluid. In other embodiments, the sample is blood, plasma, or serum. In other embodiments the sample is saliva. In other embodiments, the sample is a cell-free sample.

In other embodiments, the miRNA is selected from the group consisting of miR-125, miR-451, and miR-3613. In other embodiments, the miRNA is miR-125b. In other embodiments, the miRNA is miR-125b-5p. In other embodiments, the miRNA is miR-451a. In other embodiments, the miRNA is miR-3613-5p. In some embodiments, the at least one miRNA is let-7, let-7a, let-7b, let-7b-3p, let-7b-5p, let-7c, let-7d, let-7e, let-7f, or let-7g. In some embodiments, the miRNA is at least two of the following: miR-125b-5p, let-7b, miR-150, miR-342, and miR-3613. In some embodiments, the reference value is the presence of the at least one miRNA in samples from subjects that do not have endometriosis.

In another aspect, this disclosure provides a method of detecting miRNA comprising: (a) providing a saliva, sputum, urine, lymphatic fluid, synovial fluid, cerebrospinal fluid, stool, or mucus sample from a subject, wherein the sample comprises nucleic acids and wherein the subject is suspected of having endometriosis; (b) performing an amplification or sequencing reaction on the nucleic acids in order to detect a presence of at least one miRNA in the sample, wherein the at least one miRNA is selected from the group consisting of miR-18, miR-125, miR-126, miR-143, miR-145, miR-150, miR-214, miR-342, miR-451, miR-500, miR-553, miR-3613, miR-4668, and miR-6755; and (c) comparing the presence of the miRNA to a reference value. In some embodiments, the sample is a fluid. In other embodiments, the sample is blood, plasma, or serum. In other embodiments the sample is saliva. In other embodiments, the sample is cell-free.

In other embodiments, the miRNA is selected from the group consisting of miR-125, miR-451, and miR-3613. In other embodiments, the miRNA is miR-125b. In other embodiments, the miRNA is miR-125b-5p. In other embodiments, the miRNA is miR-451a. In other embodiments, the miRNA is miR-3613-5p. In some embodiments, the miRNA is at least two of the following: miR-125b-5p, let-7b, miR-150, miR-342, and miR-3613. In some embodiments, the reference value is the presence of the at least one miRNA in samples from subjects that do not have endometriosis.

In yet another aspect, the disclosure provides for a method comprising: (a) providing a sample from a subject, wherein the sample comprises nucleic acids and wherein the subject is suspected of having endometriosis; (b) performing a sequencing reaction on the nucleic acids to detect a presence of at least one miRNA in the sample, wherein the at least one miRNA is selected from the group consisting of miR-18, miR-125, miR-126, miR-143, miR-145, miR-150, miR-214, miR-342, miR-451, miR-500, miR-553, miR-3613, miR-4668, and miR-6755; and (c) comparing the presence of the miRNA to a reference value. In some embodiments, the at least one miRNA is detected by high-throughput or massively-parallel sequencing. In some embodiments, the miRNA is at least one of the following, at least two of the following, or all of the following: miR-125b-5p, miR-451a, and miR-3613-5p. In some embodiments, the miRNA is at least one of the following or all of the following: miR-125b-5p, let-7b, miR-150, miR-342, and miR-3613. In some embodiments, the miRNA is at least two of the following: miR-125b-5p, let-7b, miR-150, miR-342, and miR-3613.

In yet another aspect, the disclosure provides for a method of diagnosing a subject exhibiting symptoms of endometriosis or suspected of having endometriosis, the method comprising: (a) detecting a presence of at least one miRNA that is not let-7, miR-135, miR-449a, miR-34c, miR-200a, miR-200b, miR-141, miR-125b-5p, miR-150-5p, miR-342-3p, miR-145-5p, miR-143-3p, miR-500a-3p, miR-451a, miR-18a-5p, miR-6755-3p, or miR-3613-5p; and (b) diagnosing the subject with endometriosis, when the detected miRNA level is above a threshold level, wherein the diagnosing the subject with endometriosis has a specificity or sensitivity greater than 90%. In some embodiments, the disclosure provides for a method comprising: (a) detecting a presence of at least one miRNA that is not let-7, let-7a, let-7b, let-7c, let-7d, let-7e, let-7f, let-7g, miR-17-5p, miR-20a, miR-22, miR-135a, miR-135b, miR-135, miR-449a, miR-34c, miR-199a, miR-122, miR-145, miR-141, miR-542-3p, miR-9, miR-200a, miR-200a-3p, miR-200b-3p, miR-200b, miR-141, miR-141-3p, miR-125b-5p, miR-150-5p, miR-342-3p, miR-145-5p, miR-143-3p, miR-500a-3p, miR-451a, miR-18a-5p, miR-6755-3p, or miR-3613-5p.

In some embodiments, the miRNA is cell-free. In some embodiments, the miRNA is present in a cell-free sample, such as cell-free plasma, serum, saliva and/or urine.

In some embodiments, the diagnosing the subject with endometriosis is diagnosing the subject with early stage endometriosis. In other embodiments, the diagnosing the subject with endometriosis is diagnosing the subject with moderate-to-severe disease. In other embodiments, the diagnosing the subject with endometriosis is diagnosing the subject with stage III or Stage IV endometriosis. In other embodiments, the diagnosing the subject with endometriosis further comprises monitoring the subject for changes in miRNA expression levels following treatment.

In other embodiments, the diagnosing the subject with endometriosis has a specificity or sensitivity greater than 75%, greater than 80%, greater than 85%, greater than 90%, greater than 95%, or greater than 99%. In other embodiments, the diagnosing the subject with endometriosis has a specificity or sensitivity greater than 95%.

In some embodiments, the method further comprises treating the subject for endometriosis. In other embodiments, treatment is a medication to relieve pain. In other embodiments, treatment is hormone therapy. In other embodiments, treatment is a hormonal contraceptive. In other embodiments, treatment is a Gonadotropin-releasing hormone agonist. In other embodiments, treatment is a Gonadotropin-releasing hormone antagonist.

In some embodiments, the detecting comprises: (i) amplifying miRNA within the sample by performing a reverse transcription assay using a primer that specifically binds the at least one miRNA or using a universal primer, thereby producing cDNA; (ii) contacting the produced cDNA with a probe specific for the at least one miRNA, wherein the probe emits a signal upon binding the produced cDNA; and (iii) using a detector to detect the signal emitted by the probe.

In a further aspect, the disclosure provides for a method of detecting miRNA comprising: (a) providing a sample from a subject, wherein the sample comprises nucleic acids and wherein the subject is suspected of having endometriosis; (b) performing an amplification, microarray or sequencing reaction on the nucleic acids; (c) detecting a presence of at least one miRNA in the sample, wherein the at least one miRNA is selected from the group consisting of miR-126, miR-214, miR-553, and miR-4668; and (d) comparing the presence of the miRNA to a reference value. In some embodiments, the sample is a fluid. In other embodiments, the sample is blood, plasma, saliva, or serum. In some embodiments, the reference value is the presence of the at least one miRNA in samples from subjects that do not have endometriosis.

In some embodiments, the detecting is by polymerase chain reaction (PCR). In other embodiments, the detecting is by quantitative PCR. In some embodiments, the detecting is by real-time PCR. In other embodiments, the detecting comprises hybridizing a unique primer to the at least one miRNA or to cDNA derived from the at least one miRNA. In other embodiments the detecting further comprises performing a reverse transcription reaction on the at least one miRNA using at least one primer or probe specific for the at least one miRNA or using at least one universal primer. In other embodiments, the detecting comprises: (i) amplifying miRNA within the sample by performing a reverse transcription assay using a primer that specifically binds the at least one miRNA or using a universal primer, thereby producing cDNA; (ii) contacting the produced cDNA with an intercalating dye that emits a signal; and (iii) using a detector to detect the emitted signal over time. In other embodiments, the detecting comprises: (i) amplifying miRNA within the sample by performing a reverse transcription assay using a primer that specifically binds the at least one miRNA or using a universal primer, thereby producing cDNA; (ii) contacting the produced cDNA with a probe specific for the at least one miRNA, wherein the probe emits a signal upon binding the produced cDNA; and (iii) using a detector to detect the signal emitted by the probe. In other embodiments, the probe is attached to a fluorophore and a quencher. In other embodiments the detecting is by sequencing.

In some embodiments, the endometriosis is diagnosed when the at least one miRNA is at least 2-fold greater than the reference value. In other embodiments, the endometriosis is diagnosed when the at least one miRNA is at least 2-fold less than the reference value. In other embodiments, the endometriosis is diagnosed when miRNA-125b-5p is upregulated, miR-150-5p is upregulated, miR-342-3p is upregulated, miR-145-5p is upregulated, miR-143-3p is upregulated, miR-500a-3p is upregulated, or miR-18a-5p is upregulated. In other embodiments, the endometriosis is diagnosed when at least three miRNA are upregulated wherein the at least three miRNA are from the group consisting of miRNA-125b-5p, miR-150-5p, miR-342-3p, miR-145-5p, miR-143-3p, miR-500a-3p, and miR-18a-5p. In other embodiments, the endometriosis is diagnosed when miR-6755-3p is downregulated or miR-3613-5p is downregulated. In other embodiments, the endometriosis is diagnosed when miR-125b-5p is upregulated, miR-451a is upregulated, and miR-3613-5p is downregulated. In some embodiments, the endometriosis is diagnosed when miR-125b-5p is upregulated. In some embodiments, the endometriosis is diagnosed when let-7b is upregulated.

In some embodiments, the subject is negative for the presence of a KRAS variant allele. In other embodiments, the detected miRNA level is used to determine severity of disease. In other embodiments, the subject is a human subject.

In yet a further aspect, the disclosure provides a method of treating a subject with endometriosis, comprising administering an endometriosis treatment to a subject identified as having a differential level of at least one miRNA selected from the group consisting of miR-18a-5p, miR-125, miR-126, miR-143, miR-145, miR-150-5p, miR-214, miR-342, miR-451, miR-500, miR-553, miR-3613, miR-4668, and miR-6755 in a biological sample of the subject as compared to a comparator. In some embodiments, the method further comprises diagnosing the subject with endometriosis when the subject is identified as having a differential level of at least one miRNA selected from the group consisting of miR-18a-5p, miR-125, miR-126, miR-143, miR-145, miR-150-5p, miR-214, miR-342, miR-451, miR-500, miR-553, miR-3613, miR-4668, and miR-6755, as compared to the comparator.

In some embodiments, the diagnosing the subject with endometriosis comprises providing a biological sample from the subject and detecting in the biological sample the differential level of at least one miRNA selected from the group consisting of the miR-18a-5p, miR-125, miR-126, miR-143, miR-145, miR-150-5p, miR-214, miR-342, miR-451, miR-500, miR-553, miR-3613, miR-4668, and miR-6755, as compared to the comparator. In some embodiments, the at least one miRNA is at least one of the following, at least two of the following, or all of the following: miR-125b-5p, miR-451a, and miR-3613-5p. In some embodiments, the at least one miRNA is at least one of the following or all of the following: miR-125b-5p, let-7b, miR-150, miR-342, and miR-3613. In some embodiments, the at least one miRNA is at least two of the following: miR-125b-5p, let-7b, miR-150, miR-342, and miR-3613.

In some embodiments, the biological sample is a body fluid. In some embodiments, the body fluid is blood, plasma, or serum. In some embodiments, the body fluid is saliva. In some embodiments, the body fluid is urine.

In some embodiments, the diagnosing the subject with endometriosis is diagnosing the subject with early stage endometriosis. In other embodiments, the diagnosing the subject with endometriosis is diagnosing the subject with moderate-to-severe disease. In other embodiments, the diagnosing the subject with endometriosis is diagnosing the subject with stage III or stage IV endometriosis. In other embodiments, the diagnosing the subject with endometriosis further comprises monitoring the subject for changes in miRNA expression levels following treatment.

In some embodiments, the diagnosing the subject with endometriosis has a specificity or sensitivity greater than 95%. In other embodiments, the treatment is a medication to relieve pain. In other embodiments, the treatment is hormone therapy. In other embodiments, treatment is selected from the group consisting of a hormonal contraceptive, a Gonadotropin-releasing hormone agonist, and a Gonadotropin-releasing hormone antagonist.

In some embodiments, the method further comprises detecting the at least one miRNA by performing a polymerase chain reaction (PCR). In some embodiments, the method further comprises detecting the at least one miRNA by performing quantitative PCR. In some embodiments, the method further comprises detecting the at least one miRNA by: (i) amplifying miRNA within the sample by performing a reverse transcription assay using a primer that specifically binds the at least one miRNA or using a universal primer, thereby producing cDNA; (ii) contacting the produced cDNA with an intercalating dye that emits a signal; and (iii) using a detector to detect the emitted signal over time. In other embodiments, the method further comprises detecting the at least one miRNA by: (i) amplifying miRNA within the sample by performing a reverse transcription assay using a primer that specifically binds the at least one miRNA or using a universal primer, thereby producing cDNA; (ii) contacting the produced cDNA with a probe specific for the at least one miRNA, wherein the probe emits a signal upon binding the produced cDNA; and (iii) using a detector to detect the signal emitted by the probe. In other embodiments, the method further comprises detecting the at least one miRNA by sequencing. In other embodiments, the method further comprises detecting the at least one miRNA by high-throughput sequencing or massively parallel sequencing.

In some embodiments, the at least one miRNA is present at a level at least 2-fold greater than the reference value. In some embodiments, the subject is negative for the presence of KRAS variant allele. In some embodiments the subject is a human subject. In some embodiments, a level of the at least one miRNA is used to determine severity of disease.

In some embodiments, the endometriosis is diagnosed when miRNA-125b-5p is upregulated, miR-150-5p is upregulated, miR-342-3p is upregulated, miR-145-5p is upregulated, miR-143-3p is upregulated, miR-500a-3p is upregulated, or miR-18a-5p is upregulated. In other embodiments, the endometriosis is diagnosed when at least three miRNA are upregulated wherein the at least three miRNA are from the group consisting of miRNA-125b-5p, miR-150-5p, miR-342-3p, miR-145-5p, miR-143-3p, miR-500a-3p, and miR-18a-5p. In other embodiments, the endometriosis is diagnosed when miR-6755-3p is downregulated or miR-3613-5p is downregulated. In other embodiments, the endometriosis is diagnosed when miR-125b-5p is upregulated, miR-451a is upregulated, and miR-3613-5p is downregulated. In other embodiments the endometriosis is diagnosed when miR-125b-5p is upregulated.

In a further aspect, the disclosure provides a method of diagnosing and treating a subject suspected of having endometriosis, comprising: (a) providing a saliva, sputum, urine, lymphatic fluid, synovial fluid, cerebrospinal fluid, stool, or mucus sample from the subject, wherein the sample comprises miRNA associated with endometriosis; (b) detecting a level of the miRNA associated with endometriosis; (c) comparing the detected level of miRNA associated with endometriosis with a reference value in order to determine a relative level of miRNA associated with endometriosis in the fluid sample; (d) diagnosing the subject with endometriosis based on the relative level of miRNA associated with endometriosis in the saliva, sputum, urine, lymphatic fluid, synovial fluid, cerebrospinal fluid, stool or mucus sample, wherein the diagnosing the subject with endometriosis has a sensitivity or specificity greater than 90%; and (e) administering a treatment to the subject diagnosed with endometriosis.

In some embodiments, the sample from the subject is a saliva sample. In some cases, the sample from the subject is a urine sample. In some cases, the sample from the subject is a mucus sample.

In some embodiments, the diagnosing the subject with endometriosis is diagnosing the subject with early stage endometriosis. In other embodiments, the diagnosing the subject with endometriosis is diagnosing the subject with moderate-to-severe disease. In other embodiments, the diagnosing the subject with endometriosis is diagnosing the subject with stage III or stage IV endometriosis. In other embodiments, the diagnosing the subject with endometriosis further comprises monitoring the subject for changes in miRNA expression levels following treatment.

In some embodiments, the diagnosing the subject with endometriosis has a specificity or sensitivity greater than 95%. In other embodiments, the treatment is a medication to relieve pain. In other embodiments, the treatment is hormone therapy. In other embodiments, treatment is selected from the group consisting of a hormonal contraceptive, a Gonadotropin-releasing hormone agonist, and a Gonadotropin-releasing hormone antagonist.

In some embodiments, the method further comprises detecting the at least one miRNA by performing a polymerase chain reaction (PCR). In some embodiments, the method further comprises detecting the at least one miRNA by performing quantitative PCR. In some embodiments, the method further comprises detecting the at least one miRNA by: (i) amplifying miRNA within the sample by performing a reverse transcription assay using a primer that specifically binds the at least one miRNA or using a universal primer, thereby producing cDNA; (ii) contacting the produced cDNA with an intercalating dye that emits a signal; and (iii) using a detector to detect the emitted signal over time. In other embodiments, the method further comprises detecting the at least one miRNA by: (i) amplifying miRNA within the sample by performing a reverse transcription assay using a primer that specifically binds the at least one miRNA or using a universal primer, thereby producing cDNA; (ii) contacting the produced cDNA with a probe specific for the at least one miRNA, wherein the probe emits a signal upon binding the produced cDNA; and (iii) using a detector to detect the signal emitted by the probe. In other embodiments, the method further comprises detecting the at least one miRNA by sequencing. In other embodiments, the method further comprises detecting the at least one miRNA by high-throughput sequencing or massively parallel sequencing.

In some embodiments, the at least one miRNA is present at a level at least 2-fold greater than the reference value. In some embodiments, the subject is negative for the presence of KRAS variant allele. In some embodiments the subject is a human subject. In some embodiments, a level of the at least one miRNA is used to determine severity of disease.

In some embodiments, the endometriosis is diagnosed when miRNA-125b-5p is upregulated, miR-150-5p is upregulated, miR-342-3p is upregulated, miR-145-5p is upregulated, miR-143-3p is upregulated, miR-500a-3p is upregulated, or miR-18a-5p is upregulated. In other embodiments, the endometriosis is diagnosed when at least three miRNA are upregulated wherein the at least three miRNA are from the group consisting of miRNA-125b-5p, miR-150-5p, miR-342-3p, miR-145-5p, miR-143-3p, miR-500a-3p, and miR-18a-5p. In other embodiments, the endometriosis is diagnosed when miR-6755-3p is downregulated or miR-3613-5p is downregulated. In other embodiments, the endometriosis is diagnosed when miR-125b-5p is upregulated, miR-451a is upregulated, and miR-3613-5p is downregulated. In other embodiments the endometriosis is diagnosed when miR-125b-5p is upregulated.

In a further aspect, the disclosure provides a method of diagnosing and treating a subject suspected of having endometriosis, the method comprising: (a) detecting a presence of at least one miRNA that is not let-7, miR-449a, miR-34c, miR-200a, miR-200b, miR-150, miR-18a, or miR-141; (b) diagnosing the subject with endometriosis, when the detected miRNA level is above a threshold level, wherein the diagnosing the subject with endometriosis has a specificity or sensitivity greater than 90%; and (c) administering a treatment to the subject diagnosed with endometriosis.

In some embodiments, the at least one miRNA comprises miR-125b-5p, miR-451a, and miR-3613-5p. In other embodiments, the at least one miRNA is miR-125b-5p. In other embodiments the at least one miRNA is miR-3613-5p. In other embodiments, the at least one miRNA is cell-free miRNA. In other embodiments, the at least one miRNA is present in at least a 2-fold change compared to the comparator.

In some embodiments, the diagnosing the subject with endometriosis is diagnosing the subject with early stage endometriosis. In other embodiments, the diagnosing the subject with endometriosis is diagnosing the subject with moderate-to-severe disease. In other embodiments, the diagnosing the subject with endometriosis is diagnosing the subject with stage III or stage IV endometriosis. In other embodiments, the diagnosing the subject with endometriosis further comprises monitoring the subject for changes in miRNA expression levels following treatment.

In some embodiments, the diagnosing the subject with endometriosis has a specificity or sensitivity greater than 95%. In other embodiments, the treatment is a medication to relieve pain. In other embodiments, the treatment is hormone therapy. In other embodiments, treatment is selected from the group consisting of a hormonal contraceptive, a Gonadotropin-releasing hormone agonist, and a Gonadotropin-releasing hormone antagonist.

In some embodiments, the method further comprises detecting the at least one miRNA by performing a polymerase chain reaction (PCR). In some embodiments, the method further comprises detecting the at least one miRNA by performing quantitative PCR. In some embodiments, the method further comprises detecting the at least one miRNA by: (i) amplifying miRNA within the sample by performing a reverse transcription assay using a primer that specifically binds the at least one miRNA or using a universal primer, thereby producing cDNA; (ii) contacting the produced cDNA with an intercalating dye that emits a signal; and (iii) using a detector to detect the emitted signal over time. In other embodiments, the method further comprises detecting the at least one miRNA by: (i) amplifying miRNA within the sample by performing a reverse transcription assay using a primer that specifically binds the at least one miRNA or using a universal primer, thereby producing cDNA; (ii) contacting the produced cDNA with a probe specific for the at least one miRNA, wherein the probe emits a signal upon binding the produced cDNA; and (iii) using a detector to detect the signal emitted by the probe. In other embodiments, the method further comprises detecting the at least one miRNA by sequencing. In other embodiments, the method further comprises detecting the at least one miRNA by high-throughput sequencing or massively parallel sequencing.

In some embodiments, the at least one miRNA is present at a level at least 2-fold greater than the reference value. In some embodiments, the subject is negative for the presence of KRAS variant allele. In some embodiments the subject is a human subject. In some embodiments, a level of the at least one miRNA is used to determine severity of disease.

In some embodiments, the endometriosis is diagnosed when miRNA-125b-5p is upregulated, miR-150-5p is upregulated, miR-342-3p is upregulated, miR-145-5p is upregulated, miR-143-3p is upregulated, miR-500a-3p is upregulated, or miR-18a-5p is upregulated. In other embodiments, the endometriosis is diagnosed when at least three miRNA are upregulated wherein the at least three miRNA are from the group consisting of miRNA-125b-5p, miR-150-5p, miR-342-3p, miR-145-5p, miR-143-3p, miR-500a-3p, and miR-18a-5p. In other embodiments, the endometriosis is diagnosed when miR-6755-3p is downregulated or miR-3613-5p is downregulated. In other embodiments, the endometriosis is diagnosed when miR-125b-5p is upregulated, miR-451a is upregulated, and miR-3613-5p is downregulated. In other embodiments the endometriosis is diagnosed when miR-125b-5p is upregulated.

In another aspect, the disclosure provides a method of diagnosing endometriosis in a subject. In some embodiments, the method comprises determining the level of at least one miRNA in a biological sample of the subject, wherein the miRNA is at least one selected from the group consisting of miR-125, miR-150, miR-342, miR-145, miR-143, miR-500, miR-451, miR-18, miR-214, miR-126, miR-6755, miR-3613, miR-553, and miR-4668; and comparing the level of the at least one miRNA in the biological sample with the level of the at least one miRNA in a comparator, wherein when the level of the at least one miRNA in the biological sample is different than the level of the at least one miRNA in the comparator, the subject is diagnosed with endometriosis. In some embodiments, the method further comprises the step of treating the subject for endometriosis.

In some embodiments, the at least one miRNA is the combination of miR-125, miR-451 and miR-3613.

In some embodiments, the subject is human.

In some embodiments, the comparator is at least one comparator selected from the group consisting of a positive control, a negative control, a normal control, a wild-type control, a historical control, and a historical norm.

In some embodiments, the disclosure provides a method of diagnosing endometriosis in a subject, wherein the method comprises detecting that the level of at least one of miR-125, miR-150, miR-342, miR-145, miR-143, miR-500, miR-451, miR-18, miR-214, and miR-126 is increased in the biological sample compared to the level in the comparator. In another embodiment, the disclosure provides a method of diagnosing endometriosis in a subject, wherein the method comprises detecting that the level of at least one of miR-6755, miR-3613, miR-553, and miR-4668 are decreased in the biological sample compared to the level in the comparator.

In some embodiments, determining the level of the at least one miRNA utilizes at least one technique selected from the group consisting of reverse transcription, PCR, and a microarray.

In some embodiments, the biological sample is selected from the group consisting of blood, serum, plasma and any combination thereof.

In another aspect, the disclosure also provides a method of diagnosing or providing a prognosis for endometriosis in a subject, method comprising the step of: detecting altered expression of at least one gene selected from the group consisting of miR-125, miR-150, miR-342, miR-145, miR-143, miR-500, miR-451, miR-18, miR-214, miR-126, miR- 6755, miR-3613, miR-553, and miR-4668 in a biological sample of the subject suspected of or having endometriosis.

In some embodiments, the at least one gene is the combination of miR-125, miR-451 and miR-3613.

In some embodiments, the biological sample is selected from the group consisting of blood, serum, plasma, and any a combination thereof.

The disclosure also provides a kit comprising a reagent that selectively binds to at least one miRNA, wherein the at least one miRNA is at least one selected from the group consisting of miR-125, miR-150, miR-342, miR-145, miR-143, miR-500, miR-451, miR-18, miR-214, miR-126, miR-6755, miR-3613, miR-553, and miR-4668. In some embodiments, the kit comprises at least three reagents, wherein the first reagent selectively binds to miR-125, wherein the second reagent selectively binds to miR-451, and wherein the third reagent selectively binds to miR-3613.

In another aspect, the disclosure provides a method of treating a subject with endometriosis, comprising administering an endometriosis treatment to a subject identified as having a differential level of at least one selected from the group consisting of miR-125, miR-150, miR-342, miR-145, miR-143, miR-500, miR-451, miR-18, miR-214, miR-126, miR-6755, miR-3613, miR-553, and miR-4668 in a biological sample of the subject as compared to a comparator.

In another aspect, the disclosure provides a method of monitoring a response to an endometriosis treatment in a subject being treated for endometriosis, the method comprises determining the level of at least one miRNA in a biological sample of the subject, wherein the miRNA is at least one selected from the group consisting of miR-125, miR-150, miR-342, miR-145, miR-143, miR-500, miR-451, miR-18, miR-214, miR-126, miR-6755, miR-3613, miR-553, and miR-4668, and comparing the level of the at least one miRNA in the biological sample with the level of the at least one miRNA in a comparator.

BRIEF DESCRIPTION OF THE DRAWINGS

The following detailed description of preferred embodiments of the disclosure will be better understood when read in conjunction with the appended drawings. For the purpose of illustrating the disclosure, there are shown in the drawings embodiments which are presently preferred. It should be understood, however, that the disclosure is not limited to the precise arrangements and instrumentalities of the embodiments shown in the drawings.

FIG. 2 comprising

FIG. 3 comprising FIG. 3A, FIG. 3B, FIG. 3C, FIG. 3D, is an image illustrating that the combination of serum miR-125-b-5p, miR-451a, and miR-3613-5p showed the highest AUC value of 1.000

DETAILED DESCRIPTION

Figure 1:
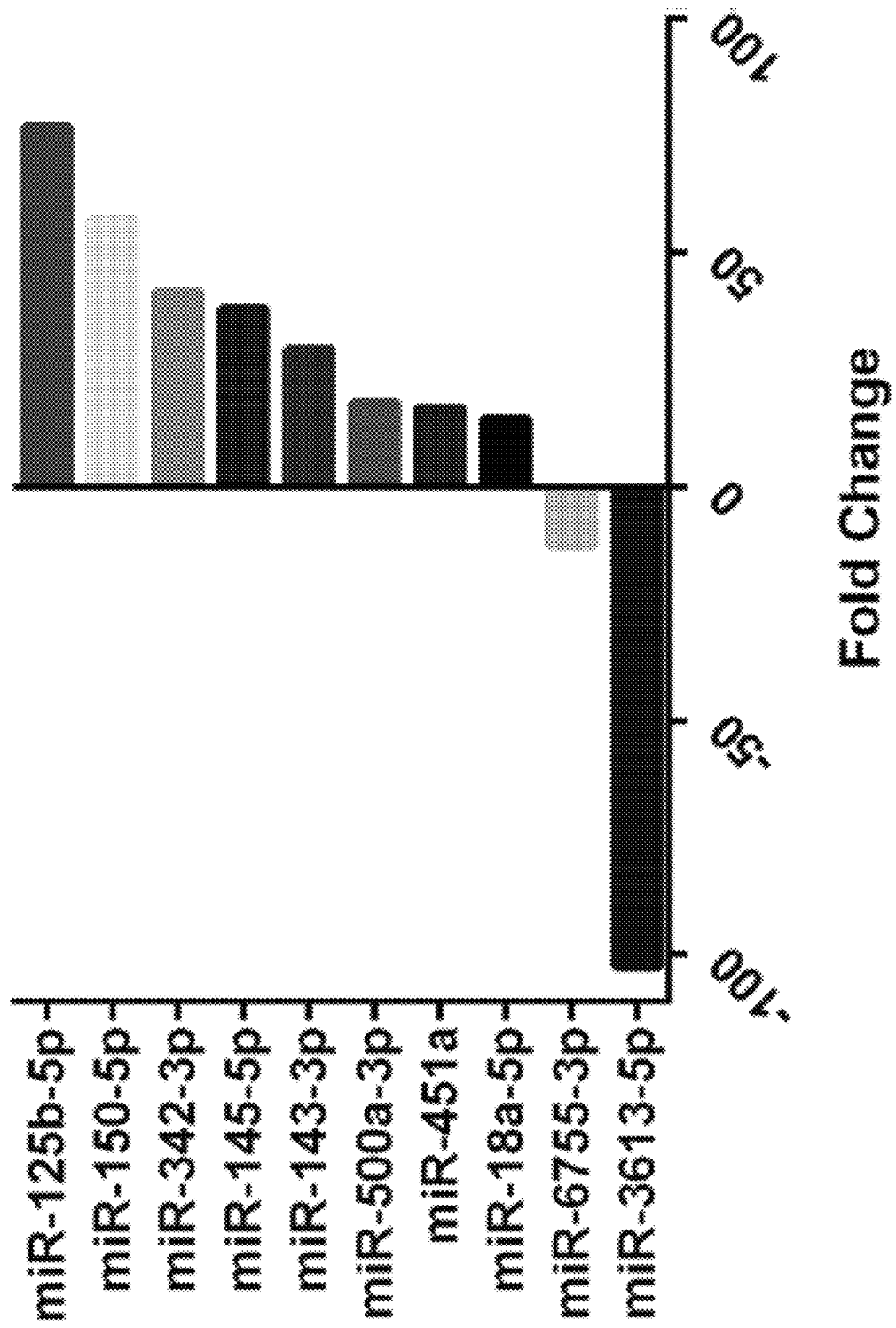
FIG. 1 is an image depicting the results of differentially expressed miRNAs in the Microarray Analysis.

The present disclosure relates to the discovery that the expression level of particular microRNAs (miRNAs) is associated with endometriosis, such as endometriosis during the proliferative phase. Thus, in various embodiments described herein, the methods of the disclosure relate to methods of diagnosing a subject as having endometriosis, methods of assessing a subject's risk of having or developing endometriosis, methods of assessing the severity of a subject's endometriosis, methods of stratifying a subject having endometriosis for assignment in a clinical trial, and methods of monitoring endometriosis treatment in a subject. Thus, the disclosure relates to compositions and methods useful for the detection and quantification of miRNAs for the diagnosis, assessment, and characterization of endometriosis in a subject in need thereof, based upon the expression level of at least one miRNA that is associated with endometriosis. The markers of the disclosure can be used to screen, diagnose, monitor the onset, monitor the progression, and assess the treatment of endometriosis. The markers of the disclosure can be used to establish and evaluate treatment plans.

In some embodiments, the miRNAs that are associated with endometriosis is a marker or biomarker of endometriosis. In various embodiments, the biomarkers of the disclosure include one or more of miR-125, miR-150, miR-342, miR-145, miR-143, miR-500, miR-451, miR-18, miR-214, miR-126, miR-6755, miR-3613, miR-553, and miR-4668. In some embodiments, the biomarkers of the disclosure include the combination of miR-125b, miR-451, and miR-3613. In some embodiments, the biomarkers of the disclosure comprise at least two of the following: miR-125b-5p, let-7b, miR-150, miR-342, and miR-3613. In some embodiments, the biomarkers of the disclosure comprise at least one of the following, at least two of the following, or all of the following: miR-125b-5p, miR-451a, and miR-3613-5p. In some embodiments, the biomarkers are at least one of the following, at least two of the following, or all of the following: miR-125b-5p, let-7b, miR-150, miR-342, and miR-3613. In some cases, the biomarkers may further comprise miR-451.

In some embodiments, the miRNAs that are associated with endometriosis is a marker or biomarker of endometriosis. In various embodiments, the biomarkers of the disclosure include one or more of miR-125b-5p, miR-150-5p, miR-342-3p, miR-145-5p, miR-143-3p, miR-500a-3p, miR-451a, miR-18a-5p, miR-214-3p, miR-126-3p, miR-6755-3p, miR-3613-5p, miR-553, and miR-4668-3p. In some embodiments, the biomarkers of the disclosure include the combination of miR-125b-5p, miR-451a, and miR-3613-5p. In some embodiments, the biomarkers include at least two of the following: miR-125b-5p, let-7b, miR-150, miR-342, and miR-3613. In some embodiments, the biomarkers include at least one of the following, at least two of the following, or all of the following: miR-125b-5p, miR-451a, and miR-3613-5p. In some embodiments, the biomarkers include at least one of the following, at least two of the following, or all of the following: miR-125b-5p, let-7b, miR-150, miR-342, and miR-3613. The biomarkers may, in some instances, further include let-7b.

In some embodiments, the disclosure provides a marker that predicts an individual's risk of developing endometriosis. In some embodiments, the markers of the disclosure can predict risk at a time when a prophylactic therapy can be administered such that the emergence of the disease is prevented.

In some embodiments, the markers of the disclosure are noninvasive biomarkers for endometriosis that allow for early detection of the disease without surgical procedures. For example, altered expression of specific miRNAs in the biological sample of the subject with endometriosis may correlate with other clinical parameters, such as pelvic pain, infertility, and disease recurrence. Therefore, the markers of the disclosure can be used, not only as biomarkers of the disease, but also as markers for prognosis and recurrence. This is an advantage because repeated surgical procedures used in the art for diagnosing endometriosis and related complications can be avoided.

The present disclosure provides biomarkers for the diagnosis and prognosis of endometriosis. Generally, the methods of this disclosure find use in diagnosing or for providing a prognosis for endometriosis by detecting the expression levels of biomarkers, which are differentially expressed (up- or down-regulated) in blood, plasma or serum from a patient. Similarly, these markers can be used to diagnose reduced fertility in a patient with endometriosis or to provide a prognosis for a fertility trial in a patient suffering from endometriosis. The present disclosure also provides methods of identifying a compound for treating or preventing endometriosis. The present disclosure provides kits for the diagnosis or prognosis of endometriosis.

Definitions

Unless defined otherwise, all technical and scientific terms used herein have the same meaning as commonly understood by one of ordinary skill in the art to which this disclosure belongs. Although any methods and materials similar or equivalent to those described herein can be used in the practice or testing of the present disclosure, the preferred methods and materials are described.

As used herein, each of the following terms has the meaning associated with it in this section.

The articles "a" and "an" are used herein to refer to one or to more than one (i.e., to at least one) of the grammatical object of the article. By way of example, "an element" means one element or more than one element.

"About" as used herein when referring to a measurable value such as an amount, a temporal duration, and the like, is meant to encompass variations of ±20%, ±10%, ±5%, ±1%, or ±0.1% from the specified value, as such variations are appropriate to perform the disclosed methods.

The term "abnormal" when used in the context of organisms, tissues, cells or components thereof, refers to those organisms, tissues, cells or components thereof that differ in at least one observable or detectable characteristic (e.g., age, treatment, time of day, etc.) from those organisms, tissues, cells or components thereof that display the "normal" (expected) respective characteristic. Characteristics which are normal or expected for one cell or tissue type, might be abnormal for a different cell or tissue type.

"Antisense," as used herein, refers to a nucleic acid sequence which is complementary to a target sequence, such as, by way of example, complementary to a target miRNA sequence, including, but not limited to, a mature target miRNA sequence, or a sub-sequence thereof. Typically, an antisense sequence is fully complementary to the target sequence across the full length of the antisense nucleic acid sequence.

The term "body fluid" or "bodily fluid" as used herein refers to any fluid from the body of an animal. Examples of body fluids include, but are not limited to, plasma, serum, blood, lymphatic fluid, cerebrospinal fluid, synovial fluid, urine, saliva, mucous, phlegm and sputum. A body fluid sample may be collected by any suitable method. The body fluid sample may be used immediately or may be stored for later use. Any suitable storage method known in the art may be used to store the body fluid sample: for example, the sample may be frozen at about −20° C. to about −70° C. Suitable body fluids are acellular fluids. "Acellular" fluids include body fluid samples in which cells are absent or are present in such low amounts that the miRNA level determined reflects its level in the liquid portion of the sample, rather than in the cellular portion. Such acellular body fluids are generally produced by processing a cell-containing body fluid by, for example, centrifugation or filtration, to remove the cells. Typically, an acellular body fluid contains no intact cells however, some may contain cell fragments or cellular debris. Examples of acellular fluids include plasma or serum, or body fluids from which cells have been removed.

As used herein, the term "cell-free" refers to the condition of the nucleic acid as it appeared in the body directly before the sample is obtained from the body. For example, nucleic acids may be present in a body fluid such as blood or saliva in a cell-free state in that they are not associated with a cell. However, the cell-free nucleic acids may have originally been associated with a cell, such as an endometrial cell prior to entering the bloodstream or other body fluid. In contrast, nucleic acids that are solely associated with cells in the body are generally not considered to be "cell-free." For example, nucleic acids extracted from a cellular sample are generally not considered "cell-free" as the term is used herein.

The term "clinical factors" as used herein, refers to any data that a medical practitioner may consider in determining a diagnosis or prognosis of disease. Such factors include, but are not limited to, the patient's medical history, a physical examination of the patient, complete blood count, analysis of the activity of enzymes, examination of cells, cytogenetics, and immunophenotyping of blood cells.

"Complementary" as used herein refers to the broad concept of subunit sequence complementarity between two nucleic acids. When a nucleotide position in both of the molecules is occupied by nucleotides normally capable of base pairing with each other, then the nucleic acids are considered to be complementary to each other at this position. Thus, two nucleic acids are substantially complementary to each other when at least about 50%, preferably at least about 60% and more preferably at least about 80% of corresponding positions in each of the molecules are occupied by nucleotides which normally base pair with each other (e.g., A:T and G:C nucleotide pairs).

As used herein, the term "diagnosis" means detecting a disease or disorder or determining the stage or degree of a disease or disorder. Usually, a diagnosis of a disease or disorder is based on the evaluation of one or more factors and/or symptoms that are indicative of the disease. That is, a diagnosis can be made based on the presence, absence or amount of a factor which is indicative of presence or absence of the disease or condition. Each factor or symptom that is considered to be indicative for the diagnosis of a particular disease does not need be exclusively related to the particular disease; i.e. there may be differential diagnoses that can be inferred from a diagnostic factor or symptom. Likewise, there may be instances where a factor or symptom that is indicative of a particular disease is present in an individual that does not have the particular disease. The diagnostic methods may be used independently, or in combination with other diagnosing and/or staging methods known in the medical art for a particular disease or disorder.

As used herein, the phrase "difference of the level" refers to differences in the quantity of a particular marker, such as a nucleic acid or a protein, in a sample as compared to a control or reference level. For example, the quantity of a particular biomarker may be present at an elevated amount or at a decreased amount in samples of patients with a disease compared to a reference level. In some embodiments, a "difference of a level" may be a difference between the quantity of a particular biomarker present in a sample as compared to a control of at least about 1%, at least about 2%, at least about 3%, at least about 5%, at least about 10%, at least about 15%, at least about 20%, at least about 25%, at least about 30%, at least about 35%, at least about 40%, at least about 50%, at least about 60%, at least about 75%, at least about 80% or more. In some embodiments, a "difference of a level" may be a statistically significant difference between the quantity of a biomarker present in a sample as compared to a control. For example, a difference may be statistically significant if the measured level of the biomarker falls outside of about 1.0 standard deviations, about 1.5 standard deviations, about 2.0 standard deviations, or about 2.5 stand deviations of the mean of any control or reference group.

A "disease" is a state of health of an animal wherein the animal cannot maintain homeostasis, and wherein if the disease is not ameliorated then the animal's health continues to deteriorate.

In contrast, a "disorder" in an animal is a state of health in which the animal is able to maintain homeostasis, but in which the animal's state of health is less favorable than it would be in the absence of the disorder. Left untreated, a disorder does not necessarily cause a further decrease in the animal's state of health.

A disease or disorder is "alleviated" if the severity of a sign or symptom of the disease or disorder, the frequency with which such a sign or symptom is experienced by a patient, or both, is reduced.

The term "comparator" describes a material comprising none, or a normal, low, or high level of one of more of the marker (or biomarker) expression products of one or more the markers (or biomarkers) of the disclosure, such that the comparator may serve as a control or reference standard against which a sample can be compared.

The terms "dysregulated" and "dysregulation" as used herein describes a decreased (down-regulated) or increased (up-regulated) level of expression of a miRNA present and detected in a sample obtained from subject as compared to the level of expression of that miRNA in a comparator sample, such as a comparator sample obtained from one or more normal, not-at-risk subjects, or from the same subject at a different time point. In some instances, the level of miRNA expression is compared with an average value obtained from more than one not-at-risk individuals. In other instances, the level of miRNA expression is compared with a miRNA level assessed in a sample obtained from one normal, not-at-risk subject.

By the phrase "determining the level of marker (or biomarker) expression" is meant an assessment of the degree of expression of a marker in a sample at the nucleic acid or protein level, using technology available to the skilled artisan to detect a sufficient portion of any marker expression product.

The terms "determining," "measuring," "assessing," and "assaying" are used interchangeably and include both quantitative and qualitative measurement, and include determining if a characteristic, trait, or feature is present or not. Assessing may be relative or absolute. "Assessing the presence of" includes determining the amount of something present, as well as determining whether it is present or absent.

"Differentially increased expression" or "up regulation" refers to expression levels which are at least 10% or more, for example, 20%, 30%, 40%, or 50%, 60%, 70%, 80%, 90% higher or more, and/or 1.1 fold, 1.2 fold, 1.4 fold, 1.6 fold, 1.8 fold, 2.0 fold higher or more, and any and all whole or partial increments there between than a comparator.

"Differentially decreased expression" or "down regulation" refers to expression levels which are at least 10% or more, for example, 20%, 30%, 40%, or 50%, 60%, 70%, 80%, 90% lower or less, and/or 2.0 fold, 1.8 fold, 1.6 fold, 1.4 fold, 1.2 fold, 1.1 fold or less lower, and any and all whole or partial increments there between than a comparator.

As used herein "endogenous" refers to any material from or produced inside an organism, cell, tissue or system.

The term "expression" as used herein is defined as the transcription and/or translation of a particular nucleotide sequence.

"Homologous" as used herein, refers to the subunit sequence similarity between two polymeric molecules, e.g., between two nucleic acid molecules, e.g., two DNA molecules or two RNA molecules, or between two polypeptide molecules. When a subunit position in both of the two molecules is occupied by the same monomeric subunit, e.g., if a position in each of two DNA molecules is occupied by adenine, then they are homologous at that position. The homology between two sequences is a direct function of the number of matching or homologous positions, e.g., if half (e.g., five positions in a polymer ten subunits in length) of the positions in two compound sequences are homologous then the two sequences are 50% homologous, if 90% of the positions, e.g., 9 of 10, are matched or homologous, the two sequences share 90% homology. By way of example, the DNA sequences 5'-ATTGCC-3' and 5'-TATGGC-3' share 50% homology.

As used herein, "homology" is used synonymously with "identity."

"Inhibitors," "activators," and "modulators" of the markers are used to refer to activating, inhibitory, or modulating molecules identified using in vitro and in vivo assays of endometriosis biomarkers. Inhibitors are compounds that, e.g., bind to, partially or totally block activity, decrease, prevent, delay activation, inactivate, desensitize, or down regulate the activity or expression of endometriosis biomarkers. "Activators" are compounds that increase, open, activate, facilitate, enhance activation, sensitize, agonize, or up regulate activity of endometriosis biomarkers, e.g., agonists Inhibitors, activators, or modulators also include genetically modified versions of endometriosis biomarkers, e.g., versions with altered activity, as well as naturally occurring and synthetic ligands, antagonists, agonists, antibodies, peptides, cyclic peptides, nucleic acids, antisense molecules, ribozymes, RNAi, microRNA, and siRNA molecules, small organic molecules and the like. Such assays for inhibitors and activators include, e.g., expressing endometriosis biomarkers in vitro, in cells, or cell extracts, applying putative modulator compounds, and then determining the functional effects on activity, as described elsewhere herein.

As used herein, an "instructional material" includes a publication, a recording, a diagram, or any other medium of expression which can be used to communicate the usefulness of a compound, composition, vector, method or delivery system of the disclosure in the kit for effecting alleviation of the various diseases or disorders recited herein. Optionally, or alternately, the instructional material can describe one or more methods of alleviating the diseases or disorders in a cell or a tissue of a mammal. The instructional material of the kit of the disclosure can, for example, be affixed to a container which contains the identified compound, composition, vector, or delivery system of the disclosure or be shipped together with a container which contains the identified compound, composition, vector, or delivery system. Alternatively, the instructional material can be shipped separately from the container with the intention that the instructional material and the compound be used cooperatively by the recipient.

As used herein, "isolated" means altered or removed from the natural state through the actions, directly or indirectly, of a human being. For example, a nucleic acid or a peptide naturally present in a living animal is not "isolated," but the same nucleic acid or peptide partially or completely separated from the coexisting materials of its natural state is "isolated." An isolated nucleic acid or protein can exist in substantially purified form, or can exist in a non-native environment such as, for example, a host cell.

"Measuring" or "measurement," or alternatively "detecting" or "detection," means assessing the presence, absence, quantity or amount (which can be an effective amount) of either a given substance within a clinical or subject-derived sample, including the derivation of qualitative or quantitative concentration levels of such substances, or otherwise evaluating the values or categorization of a subject's clinical parameters.

As used herein, "microRNA" or "miRNA" describes small non-coding RNA molecules, generally about 15 to about 50 nucleotides in length, preferably 17-23 nucleotides, which can play a role in regulating gene expression through, for example, a process termed RNA interference (RNAi). RNAi describes a phenomenon whereby the presence of an RNA sequence that is complementary or antisense to a sequence in a target gene messenger RNA (mRNA) results in inhibition of expression of the target gene. miRNAs are processed from hairpin precursors of about 70 or more nucleotides (pre-miRNA) which are derived from primary transcripts (pri-miRNA) through sequential cleavage by RNAse III enzymes. miRBase is a comprehensive microRNA database located at www.mirbase.org, incorporated by reference herein in its entirety for all purposes.

A "mutation," as used herein, refers to a change in nucleic acid or polypeptide sequence relative to a reference sequence (which is preferably a naturally-occurring normal or "wild-type" sequence), and includes translocations, deletions, insertions, and substitutions/point mutations. A "mutant," as used herein, refers to either a nucleic acid or protein comprising a mutation.

"Naturally occurring" as used herein describes a composition that can be found in nature as distinct from being artificially produced. For example, a nucleotide sequence present in an organism, which can be isolated from a source in nature and which has not been intentionally modified by a person, is naturally occurring.

By "nucleic acid" is meant any nucleic acid, whether composed of deoxyribonucleosides or ribonucleosides, and whether composed of phosphodiester linkages or modified linkages such as phosphotriester, phosphoramidate, siloxane, carbonate, carboxymethylester, acetamidate, carbamate, thioether, bridged phosphoramidate, bridged methylene phosphonate, phosphorothioate, methylphosphonate, phosphorodithioate, bridged phosphorothioate or sulfone linkages, and combinations of such linkages. The term nucleic acid also specifically includes nucleic acids composed of bases other than the five biologically occurring bases (adenine, guanine, thymine, cytosine and uracil).

Conventional notation is used herein to describe polynucleotide sequences: the left-hand end of a single-stranded polynucleotide sequence is the 5'-end; the left-hand direction of a double-stranded polynucleotide sequence is referred to as the 5'-direction.

The direction of 5' to 3' addition of nucleotides to nascent RNA transcripts is referred to as the transcription direction. The DNA strand having the same sequence as an mRNA is referred to as the "coding strand." Sequences on the DNA strand which are located 5' to a reference point on the DNA are referred to as "upstream sequences." Sequences on the DNA strand which are 3' to a reference point on the DNA are referred to as "downstream sequences."

As used herein, "polynucleotide" includes cDNA, RNA, DNA/RNA hybrid, anti-sense RNA, siRNA, miRNA, genomic DNA, synthetic forms, and mixed polymers, both sense and antisense strands, and may be chemically or biochemically modified to contain non-natural or derivatized, synthetic, or semi-synthetic nucleotide bases. Also, included within the scope of the disclosure are alterations of a wild type or synthetic gene, including but not limited to deletion, insertion, substitution of one or more nucleotides, or fusion to other polynucleotide sequences.

As used herein, a "primer" for amplification is an oligonucleotide that specifically anneals to a target or marker nucleotide sequence. The 3' nucleotide of the primer should be identical to the target or marker sequence at a corresponding nucleotide position for optimal primer extension by a polymerase. As used herein, a "forward primer" is a primer that anneals to the anti-sense strand of double stranded DNA (dsDNA). A "reverse primer" anneals to the sense-strand of dsDNA.

The term "recombinant DNA" as used herein is defined as DNA produced by joining pieces of DNA from different sources.

As used herein, the term "providing a prognosis" refers to providing a prediction of the probable course and outcome of endometriosis, including prediction of severity, duration, chances of recovery, etc. The methods can also be used to devise a suitable therapeutic plan, e.g., by indicating whether or not the condition is still at an early stage or if the condition has advanced to a stage where aggressive therapy would be ineffective.

A "reference level" of a biomarker means a level of the biomarker that is indicative of a particular disease state, phenotype, or lack thereof, as well as combinations of disease states, phenotypes, or lack thereof. A "positive" reference level of a biomarker means a level that is indicative of a particular disease state or phenotype. A "negative"

reference level of a biomarker means a level that is indicative of a lack of a particular disease state or phenotype.

"Sample" or "biological sample" as used herein means a biological material isolated from an individual. The biological sample may contain any biological material suitable for detecting the desired biomarkers, and may comprise cellular and/or non-cellular material obtained from the individual.

"Standard control value" as used herein refers to a predetermined amount of a particular protein or nucleic acid that is detectable in a biological sample. The standard control value is suitable for the use of a method of the present disclosure, in order for comparing the amount of a protein or nucleic acid of interest that is present in a biological sample. An established sample serving as a standard control provides an average amount of the protein or nucleic acid of interest in the biological sample that is typical for an average, healthy person of reasonably matched background, e.g., gender, age, ethnicity, and medical history. A standard control value may vary depending on the protein or nucleic acid of interest and the nature of the sample (e.g., serum).

The terms "subject," "patient," "individual," and the like are used interchangeably herein, and refer to any animal, or cells thereof whether in vitro or in situ, amenable to the methods described herein. In certain non-limiting embodiments, the patient, subject or individual is a human.

The terms "underexpress," "underexpression," "underexpressed," or "down-regulated" interchangeably refer to a protein or nucleic acid that is transcribed or translated at a detectably lower level in a biological sample from a woman with endometriosis, in comparison to a biological sample from a woman without endometriosis. The term includes underexpression due to transcription, post transcriptional processing, translation, post-translational processing, cellular localization (e.g., organelle, cytoplasm, nucleus, cell surface), and RNA and protein stability, as compared to a control. Underexpression can be detected using conventional techniques for detecting mRNA (i.e., Q-PCR, RT-PCR, PCR, hybridization) or proteins (i.e., ELISA, immunohistochemical techniques). Underexpression can be 10%, 20%, 30%, 40%, 50%, 60%, 70%, 80%, 90% or less in comparison to a control. In certain instances, underexpression is 1-, 2-, 3-, 4-, 5-, 6-, 7-, 8-, 9-, 10-fold or more lower levels of transcription or translation in comparison to a control.

The terms "overexpress," "overexpression," "overexpressed," or "up-regulated" interchangeably refer to a protein or nucleic acid (RNA) that is transcribed or translated at a detectably greater level, usually in a biological sample from a woman with endometriosis, in comparison to a biological sample from a woman without endometriosis. The term includes overexpression due to transcription, post transcriptional processing, translation, post-translational processing, cellular localization (e.g., organelle, cytoplasm, nucleus, cell surface), and RNA and protein stability, as compared to a cell from a woman without endometriosis. Overexpression can be detected using conventional techniques for detecting mRNA (i.e., Q-PCR, RT-PCR, PCR, hybridization) or proteins (i.e., ELISA, immunohistochemical techniques). Overexpression can be 10%, 20%, 30%, 40%, 50%, 60%, 70%, 80%, 90% or more in comparison to a cell from a woman without endometriosis. In certain instances, overexpression is 1-, 2-, 3-, 4-, 5-, 6-, 7-, 8-, 9-, 10-fold, or more higher levels of transcription or translation in comparison to a cell from a woman without endometriosis.

"Variant" as the term is used herein, is a nucleic acid sequence or a peptide sequence that differs in sequence from a reference nucleic acid sequence or peptide sequence respectively, but retains essential properties of the reference molecule. Changes in the sequence of a nucleic acid variant may not alter the amino acid sequence of a peptide encoded by the reference nucleic acid, or may result in amino acid substitutions, additions, deletions, fusions and truncations. Changes in the sequence of peptide variants are typically limited or conservative, so that the sequences of the reference peptide and the variant are closely similar overall and, in many regions, identical. A variant and reference peptide can differ in amino acid sequence by one or more substitutions, additions, deletions in any combination. A variant of a nucleic acid or peptide can be a naturally occurring such as an allelic variant, or can be a variant that is not known to occur naturally. Non-naturally occurring variants of nucleic acids and peptides may be made by mutagenesis techniques or by direct synthesis.

As used herein, the terms "treat," "ameliorate," "treatment," and "treating" are used interchangeably. These terms refer to an approach for obtaining beneficial or desired results including, but are not limited to, therapeutic benefit and/or a prophylactic benefit. Therapeutic benefit means eradication or amelioration of the underlying disorder being treated. Also, a therapeutic benefit is achieved with the eradication or amelioration of one or more of the physiological symptoms associated with the underlying disorder such that an improvement is observed in the patient, notwithstanding that the patient can still be afflicted with the underlying disorder. For prophylactic benefit, treatment may be administered to a patient at risk of developing a particular disease, or to a patient reporting one or more of the physiological symptoms of a disease, even though a diagnosis of this disease may not have been made.

The term "or" as used herein and throughout the disclosure, generally means "and/or" unless the context dictates otherwise.

As used herein, the term "circulating miRNA" refers to any miRNA in a body fluid, regardless of whether the body fluid is traditionally considered to be a part of the circulatory system. For example, "circulating miRNA" would encompass miRNA present in a subject's blood and would also encompass miRNA present in a subject's saliva, urine, or other bodily fluid.

Ranges: throughout this disclosure, various aspects of the disclosure can be presented in a range format. It should be understood that the description in range format is merely for convenience and brevity and should not be construed as an inflexible limitation on the scope of the disclosure. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

Description

In one aspect, the present disclosure relates to the discovery of a link between endometriosis and alterations in circulating miRNA levels. In some embodiments, the level of circulating miRNAs, alone and in combination with conventional endometriosis serum markers, are used to improve endometriosis detection. In exemplary embodiment, the miRNAs are selected from the group consisting of:

miR-125, miR-150, miR-342, miR-145, miR-143, miR-500, miR-451, miR-18, miR-214, miR-126, miR-6755, miR-3613, miR-553, and miR-4668 and any combination thereof. In exemplary embodiments, the miRNAs are selected from the group consisting of: miR-125b-5p, miR-150-5p, miR-342-3p, miR-145-5p, miR-143-3p, miR-500a-3p, miR-451a, miR-18a-5p, miR-214-3p, miR-126-3p, miR-6755-3p, miR-3613-5p, miR-553, and miR-4668-3p and any combination thereof. In some embodiments, the miRNA is at least two of the following: miR-125b-5p, let-7b, miR-150, miR-342, and miR-3613. In some embodiments, the miRNA is at least one of the following, at least two of the following, or all of the following: miR-125b-5p, miR-451a, and miR-3613-5p. In some embodiments, the miRNA is at least one of the following, at least two of the following, or all of the following: miR-125b-5p, let-7b, miR-150, miR-342, and miR-3613. In some cases, the miRNA of the disclosure further comprise let-7b.

In one aspect, the methods generally provide for the detection, measuring, and comparison of a pattern of circulating miRNA in a patient sample. In other aspects, the methods generally provide for detection, measuring and comparison of a pattern of miRNA present in a sample of bodily fluid (e.g., blood, plasma, serum, saliva, urine). In the context of endometriosis, it is frequently difficult to have access to the diseased cells. As such, a method that detects endometriosis using a relatively non-invasive method such as a blood draw or collection of saliva would be very beneficial. In various embodiments, the present methods overcome problems of cancer diagnosis by determining the levels of miRNAs in the plasma of patients with liver diseases. An alteration (i.e., an increase or decrease) in the level of a miRNA gene product in the sample obtained from the subject, relative to the level of a corresponding miRNA gene product in a control sample, is indicative of the presence of endometriosis in the subject. In some embodiments, the level of at least one miRNA gene product in the test sample is greater than the level of the corresponding miRNA gene product in the control sample. In another embodiment, the level of at least one miRNA gene product in the test sample is less than the level of the corresponding miRNA gene product in the control sample.

Additional diagnostic markers may be combined with the circulating miRNA level to construct models for predicting the presence or absence or stage of a disease. For example, clinical factors of relevance to the diagnosis of endometriosis diseases, include, but are not limited to, the patient's medical history, a physical examination, and other biomarkers. A diagnosis of endometriosis may also be informed by a patient's symptoms, including the type of symptoms, duration of symptoms and degree of symptoms.

Generally, the methods of this disclosure find use in diagnosing or for providing a prognosis for endometriosis by detecting the expression levels of biomarkers, which are differentially expressed (up- or down-regulated) in blood or serum from a patient. These markers can be used to distinguish the stage or severity of endometriosis. These markers can also be used to provide a prognosis for the course of treatment in a patient with endometriosis. Similarly, these markers can be used to diagnose infertility in a patient with endometriosis or to provide a prognosis for a fertility trial in a patient suffering from endometriosis. The biomarkers of the present disclosure can be used alone or in combination for the diagnosis or prognosis of endometriosis.

In some embodiments, the methods of the present disclosure find use in assigning treatment to a patient suffering from endometriosis. By detecting the expression levels of biomarkers found herein, the appropriate treatment can be assigned to a patient suffering from endometriosis. These treatments can include, but are not limited to, hormone therapy, chemotherapy, immunotherapy, and surgical treatment. Similarly, the methods of the current disclosure can be used to assign treatment to a patient with reduced fertility due to endometriosis. In this fashion, by determining the degree to which the patient's fertility has been reduced, through the detection of biomarkers found herein, the appropriate treatment can be assigned. Relevant treatments include, but are not limited to, hormone therapy, chemotherapy, immunotherapy, and surgical treatment.

Diagnostic and prognostic kits comprising one or more markers for use are provided herein. Also provided by the disclosure are methods for identifying compounds that are able to prevent or treat endometriosis or reduced fertility caused by endometriosis by modulating the expression level or activity of markers found in any one of the identified gene subsets. Therapeutic methods are provided, wherein endometriosis or reduced fertility caused by endometriosis is treated using an agent that targets the markers of the disclosure.

In various embodiments, the methods of the disclosure relate to methods of assessing a subject's risk of having or developing endometriosis, methods of assessing the severity of a subject's endometriosis, methods of diagnosing endometriosis, methods of characterizing endometriosis, and methods of stratifying a subject having endometriosis in a clinical trial.

In various embodiments of the compositions and methods of the disclosure described herein, the miRNA associated with endometriosis is at least one of the following miRNAs: miR-125, miR-150, miR-342, miR-145, miR-143, miR-500, miR-451, miR-18, miR-214, miR-126, miR-6755, miR-3613, miR-553, and miR-4668. Sequences of the miRNA family members are publicly available from miRBase at (www.mirbase.org). In some embodiments, the miRNA associated with endometriosis is at least one of the following miRNAs, or further comprises one of the following miR-NAs: let-7, let-7a, let-7b, let-7b-3p, let-7b-5p, let-7c, let-7d, let-7e, let-7f, or let-7g. In some embodiments, the miRNA associated with endometriosis is at least two of the following: miR-125b-5p, let-7b, miR-150, miR-342, and miR-3613. In some embodiments, the miRNA is at least one of the following, at least two of the following, or all of the following: miR-125b-5p, miR-451a, and miR-3613-5p. In some embodiments, the miRNA is at least one of the following, at least two of the following, or all of the following: miR-125b-5p, let-7b, miR-150, miR-342, and miR-3613.

In various embodiments of the compositions and methods of the disclosure described herein, the miRNA associated with endometriosis is at least one of the following miRNAs: miR-125b-5p, miR-150-5p, miR-342-3p, miR-145-5p, miR-143-3p, miR-500a-3p, miR-451a, miR-18a-5p, miR-214-3p, miR-126-3p, miR-6755-3p, miR-3613-5p, miR-553, and miR-4668-3p. Sequences of the miRNA family members are publicly available from miRBase at (www.mirbase.org).

In some embodiments, the biomarkers of the disclosure include one or more of miR-125, miR-150, miR-342, miR-145, miR-143, miR-500, miR-451, miR-18a, miR-214, miR-126, miR-6755, miR-3613, miR-553, and miR-4668. In some embodiments, biomarkers of the disclosure useful for diagnosing endometriosis include one or more of miR-125b, miR-150, miR-342, miR-145, miR-143, miR-500, miR-451, miR-18, miR-214, miR-126, miR-6755, miR-3613, miR-553, and miR-4668. In some embodiments, biomarkers of the disclosure useful for diagnosing endometriosis include the combination of miR-125b, miR-451 and miR-3613. In further embodiments, the biomarkers useful for diagnosing endometriosis further include one or more of the following: let-7, let-7a, let-7b, let-7b-3p, let-7b-5p, let-7c, let-7d, let-7e, let-7f, or let-7g. In some specific cases, the biomarkers further comprise let-7b. In some embodiments, the biomarkers include at least two of the following: miR-125b-5p, let-7b, miR-150, miR-342, and miR-3613. In some embodiments, the biomarkers include at least one of the following, at least two of the following, or all of the following: miR-125b-5p, miR-451a, and miR-3613-5p. In some embodiments, the biomarkers include at least one of the following, at least two of the following, or all of the following: miR-125b-5p, let-7b, miR-150, miR-342, and miR-3613. In some cases, the biomarkers may further include miR-451.

In some embodiments, the biomarkers of the disclosure include one or more of miR-125b-5p, miR-150-5p, miR-342-3p, miR-145-5p, miR-143-3p, miR-500a-3p, miR-451a, miR-18a-5p, miR-214-3p, miR-126-3p, miR-6755-3p, miR-3613-5p, miR-553, and miR-4668-3p. In some embodiments, biomarkers of the disclosure useful for diagnosing endometriosis include one or more of miR-125b-5p, miR-150-5p, miR-342-3p, miR-145-5p, miR-143-3p, miR-500a-3p, miR-451a, miR-18a-5p, miR-214-3p, miR-126-3p, miR-6755-3p, miR-3613-5p, miR-553, and miR-4668-3p. In a preferred embodiment, biomarkers of the disclosure useful for diagnosing endometriosis include the combination of miR-125b-5p, miR-451a and miR-3613-5p. In some embodiments, the biomarkers useful for diagnosing endometriosis include at least two of the following: miR-125b-5p, let-7b, miR-150, miR-342, and miR-3613. In some embodiments, the biomarkers useful for diagnosing endometriosis include at least one of the following, at least two of the following, or all of the following: miR-125b-5p, miR-451a, and miR-3613-5p. In some embodiments, the biomarkers useful for diagnosing endometriosis include at least one of the following, at least two of the following, or all of the following: miR-125b-5p, let-7b, miR-150, miR-342, and miR-3613. In some cases, they may further include miR-451. In some cases, they may further include let-7b.

In some embodiments, the biomarkers of the disclosure are one or more miRNA associated with endometriosis which are down-regulated, or expressed at a lower than normal level. For example, it is described herein that miR-6755, miR-3613, miR-553, and miR-4668 are down regulated or expressed at a lower than normal level in subjects with endometriosis. Thus, in certain embodiments, the disclosure relates to compositions and methods useful for the diagnosis, assessment, and characterization of endometriosis in a subject in need thereof, based upon the detection of a decreased level of at least one of miR-6755, miR3613, miR-553, and miR-4668.

In some embodiments, the biomarkers of the disclosure are one or more miRNA associated with endometriosis which are down-regulated, or expressed at a lower than normal level. For example, it is described herein that miR-6755-3p, miR-3613-5p, miR-553, and miR-4668-3p are down regulated or expressed at a lower than normal level in subjects with endometriosis. Thus, in certain embodiments, the disclosure relates to compositions and methods useful for the diagnosis, assessment, and characterization of endometriosis in a subject in need thereof, based upon the detection of a decreased level of at least one of miR-6755-3p, miR3613-5p, miR-553, and miR-4668-3p.

In some embodiments, the biomarkers of the disclosure are one or more miRNA associated with endometriosis which are upregulated, or expressed at a higher than normal level. For example, it is described herein that miR-125, miR-150, miR-342, miR-145, miR-143, miR-500, miR-451, miR-18, miR-214, and miR-126 are upregulated or expressed at a higher than normal level in subjects with endometriosis. Thus, in certain embodiments, the disclosure relates to compositions and methods useful for the diagnosis, assessment, and characterization of endometriosis in a subject in need thereof, based upon the detection of an increased level of at least one of miR-125, miR-150, miR-342, miR-145, miR-143, miR-500, miR-451, miR-18, miR-214, and miR-126. In some cases, one or more of the following miRNA are upregulated or expressed at a higher than normal level in subjects with endometriosis: let-7, let-7a, let-7b, let-7b-3p, let-7b-5p, let-7c, let-7d, let-7e, let-7f, or let-7g. In some embodiments, the biomarkers of the disclosure are one or more miRNA associated with endometriosis which are upregulated, or expressed at a higher than normal level. For example, it is described herein that miR-125b-5p, miR-150-5p, miR-342-3p, miR-145-5p, miR-143-3p, miR-500a-3p, miR-451a, miR-18a-5p, miR-214-3p, and miR-126-3p are upregulated or expressed at a higher than normal level in subjects with endometriosis. Thus, in certain embodiments, the disclosure relates to compositions and methods useful for the diagnosis, assessment, and characterization of endometriosis in a subject in need thereof, based upon the detection of an increased level of at least one of miR-125b-5p, miR-150-5p, miR-342-3p, miR-145-5p, miR-143-3p, miR-500a-3p, miR-451a, miR-18a-5p, miR-214-3p, and miR-126-3p.

In some embodiments, the disclosure provides a method for detecting a marker of endometriosis. In some embodiments, the disclosure provides a method for monitoring the levels of miRNAs in response to treatment. In some embodiments, the disclosure provides a method for monitoring at least one of miR-125b-5p, miR-150-5p, miR-342-3p, miR-145-5p, miR-143-3p, miR-500a-3p, miR-451a, miR-18a-5p, miR-214-3p, miR-126-3p, miR-6755-3p, miR-3613-5p, miR-553, and miR-4668-3p after treatment. In some embodiments, the disclosure provides a method for monitoring the levels of miR-125b-5p, miR-150-5p, miR-3613-5p or any combination thereof after endometriosis treatment. In some embodiments, the disclosure provides a method for monitoring the levels of let-7, let-7a, let-7b, let-7b-3p, let-7b-5p, let-7c, let-7d, let-7e, let-7f, or let-7g often in addition to another miRNA provided herein. In some embodiments, the monitored miRNA is at least two of the following: miR-125b-5p, let-7b, miR-150, miR-342, and miR-3613. In some embodiments, the monitored miRNA is at least one of the following, at least two of the following, or all of the following: miR-125b-5p, miR-451a, and miR-3613-5p. In some embodiments, the monitored miRNA is at least one of the following, at least two of the following, or all of the following: miR-125b-5p, let-7b, miR-150, miR-342, and miR-3613.

In some cases, the method may include diagnosing endometriosis by measuring the level of at least one of the following miRNA: let-7a, let-7b, let-7c, let-7c, let-7d, let-7e, let-7f, and let-7g. In some cases, the method may include diagnosing endometriosis by measuring the level of at least two of the following miRNA: let-7a, let-7b, let-7c, let-7c, let-7d, let-7e, let-7f, and let-7g. In some cases, the method may include diagnosing endometriosis by measuring the level of at least three of the following miRNA: let-7a, let-7b, let-7c, let-7c, let-7d, let-7e, let-7f, and let-7g.

In some embodiments, the disclosure provides a method for detecting at least one, at least two, at least three, at least four, at least five, or at least ten of the miRNAs listed in Table 1. In some embodiments, the disclosure provides a method for detecting nucleic acids that have at least 50%, at least 55%, at least 60%, at least 65%, at least 70%, at least 75%, at least 80%, at least 85%, at least 90%, or at least 100% homology to at least one of the sequences listed in Table 1.

TABLE 1 miRNA sequences

| SEQ ID NO.: | Name | Sequence |
|---|---|---|
| 1 | miR-18a-3p | ACUGCCCUAAGUGCUCCUUCUGG |
| 2 | miR-18a-5p | UAAGGUGCAUCUAGUGCAGAUAG |
| 3 | miR-18b-3p | UGCCCUAAAUGCCCCUUCUGGC |
| 4 | miR-18b-5p | UAAGGUGCAUCUAGUGCAGUUAG |
| 5 | miR-125a-3p | ACAGGUGAGGUUCUUGGGAGCC |
| 6 | miR-125a-5p | UCCCUGAGACCCUUUAACCUGUGA |
| 7 | miR-125b-1-3p | ACGGGUUAGGCUCUUGGGAGCU |
| 8 | miR-125b-2-3p | UCACAAGUCAGGCUCUUGGGAC |
| 9 | miR-125b-5p | UCCCUGAGACCCUAACUUGUGA |
| 10 | miR-126-3p | UCGUACCGUGAGUAAUAAUGCG |
| 11 | miR-126-5p | CAUUAUUACUUUUGGUACGCG |
| 12 | miR-143-3p | UGAGAUGAAGCACUGUAGCUC |
| 13 | miR-143-5p | GGUGCAGUGCUGCAUCUCUGGU |
| 14 | miR-145-3p | GGAUUCCUGGAAAUACUGUUCU |
| 15 | miR-145-5p | GUCCAGUUUUCCCAGGAAUCCCU |
| 16 | miR-150-3p | CUGGUACAGGCCUGGGGGACAG |
| 17 | miR-150-5p | UCUCCCAACCCUUGUACCAGUG |
| 18 | miR-214-3p | ACAGCAGGCACAGACAGGCAGU |
| 19 | miR-214-5p | UGCCUGUCUACACUUGCUGUGC |
| 20 | miR-342-3p | UCUCACACAGAAAUCGCACCCGU |
| 21 | miR-342-5p | AGGGGUGCUAUCUGUGAUUGA |
| 22 | miR-451a | AAACCGUUACCAUUACUGAGUU |
| 23 | miR-451b | UAGCAAGAGAACCAUUACCAUU |
| 24 | miR-500a-3p | AUGCACCUGGGCAAGGAUUCUG |
| 25 | miR-500a-5p | UAAUCCUUGCUACCUGGGUGAGA |
| 26 | miR-500b-3p | GCACCCAGGCAAGGAUUCUG |
| 27 | miR-500b-5p | AAUCCUUGCUACCUGGGU |
| 28 | miR-553 | AAAACGGUGAGAUUUUGUUUU |
| 29 | miR-3613-3p | ACAAAAAAAAAGCCCAACCCUUC |
| 30 | miR-3613-5p | UGUUGUACUUUUUUUUUUGUUC |
| 31 | miR-4668-3p | GAAAAUCCUUUUUGUUUUUCCAG |
| 32 | miR-4668-5p | AGGGAAAAAAAAAGGAUUUGUC |

TABLE 1 -continued miRNA sequences

| SEQ ID NO.: | Name | Sequence |
|---|---|---|
| 33 | miR-6755-3p | UGUUGUCAUGUUUUUUCCCUAG |
| 34 | miR-6755-5p | UAGGGUAGACACUGACAACGUU |
| 35 | let-7b-3p | CUAUACAACCUACUGCCUUCCC |
| 36 | let-7b-5p | UGAGGUAGUAGGUUGUGUGGUU |

Accordingly, the disclosure may provide a new and convenient platform for detecting a marker of endometriosis, often with relatively high sensitivity. In some embodiments, the system of the disclosure provides a platform for detecting a marker of endometriosis with at least 80% sensitivity, preferably at least 90%, preferably at least 91%, preferably at least 92%, preferably at least 93%, preferably at least 94%, preferably at least 95%, preferably at least 96%, preferably at least 97%, preferably at least 98%, preferably at least 99%, preferably at least 100%.

In some embodiments, the system of the disclosure provides a platform for detecting a marker of endometriosis. In some embodiments, the system of the disclosure provides a platform for detecting a marker of endometriosis with at least 80% specificity, preferably at least 90%, preferably at least 91%, preferably at least 92%, preferably at least 93%, preferably at least 94%, preferably at least 95%, preferably at least 96%, preferably at least 97%, preferably at least 98%, preferably at least 99%, preferably at least 100%.

In some embodiments, the disclosure provides a system for detecting a marker of endometriosis, with at least 90%, 91%, 92%, 93%, 94%, 95%, 96%, 97%, 98%, 99%, 100% sensitivity; at least 90%, 91%, 92%, 93%, 94%, 95%, 96%, 97%, 98%, 99%, 100% specificity; or both at least 90%, 91%, 92%, 93%, 94%, 95%, 96%, 97%, 98%, 99%, 100% sensitivity and specificity. In some embodiments, the disclosure provides a system for detecting a marker of endometriosis with at least 90%, 91%, 92%, 93%, 94%, 95%, 96%, 97%, 98%, 99%, 100% accuracy.

Accordingly, the disclosure may provide new and convenient methods for detecting one or more markers of endometriosis, often with relatively high sensitivity. In some embodiments, the methods detect or diagnose endometriosis with at least 80% sensitivity, preferably at least 90%, preferably at least 91%, preferably at least 92%, preferably at least 93%, preferably at least 94%, preferably at least 95%, preferably at least 96%, preferably at least 97%, preferably at least 98%, preferably at least 99%, preferably at least 100%.

In some embodiments, the methods of the disclosure detect endometriosis with at least 80% specificity, preferably at least 90%, preferably at least 91%, preferably at least 92%, preferably at least 93%, preferably at least 94%, preferably at least 95%, preferably at least 96%, preferably at least 97%, preferably at least 98%, preferably at least 99%, preferably at least 100%. In some embodiments, the disclosure provides methods of detecting or diagnosing endometriosis, with at least 90%, 91%, 92%, 93%, 94%, 95%, 96%, 97%, 98%, 99%, 100% sensitivity; at least 90%, 91%, 92%, 93%, 94%, 95%, 96%, 97%, 98%, 99%, 100% specificity; or both at least 90%, 91%, 92%, 93%, 94%, 95%, 96%, 97%, 98%, 99%, 100% sensitivity and specificity. In some embodiments, the disclosure provides methods of diagnosing endometriosis with at least 90%, 91%, 92%, 93%, 94%, 95%, 96%, 97%, 98%, 99%, 100% accuracy.

Sample Preparation

Test samples of acellular body fluid or cell-containing samples may be obtained from an individual or patient. Methods of obtaining test samples are well-known to those of skill in the art and include, but are not limited to aspirations or drawing of blood or other fluids. Samples may include, but are not limited to, whole blood, serum, plasma, saliva, cerebrospinal fluid (CSF), pericardial fluid, pleural fluid, urine, and eye fluid. In some embodiments in which the test sample contains cells, the cells may be removed from the liquid portion of the sample by methods known in the art (e.g., centrifugation) to yield acellular body fluid. In suitable embodiments, serum or plasma are used as the acellular body fluid sample. Plasma and serum can be prepared from whole blood using suitable methods well-known in the art. In these embodiments, data may be normalized by volume of acellular body fluid.

In some embodiments, test samples of saliva may be obtained from a subject. Methods of obtaining saliva samples may include, but are not limited to forcible ejection from the subject's mouth (e.g., spitting), aspiration, removal by a swab or other collection tool, or any other method known in the art. As used herein, the term "saliva" does not include sputum, since sputum pertains to mucus or phlegm samples. In some embodiments, the saliva may be separated into cellular and non-cellular fractions by methods known in the art (e.g., centrifugation). In some embodiments, nucleic acids may be extracted from the cellular or non-cellular fractions.

Variability in sample preparation of cell-containing samples can be corrected by normalizing the data by, for example, protein content or cell number. In certain embodiments, the sample may be normalized relative to the total protein content in the sample. Total protein content in the sample can be determined using standard procedures, including, without limitation, Bradford assay and the Lowry method. In other embodiments, the sample may be normalized relative to cell number.

Assays

The present disclosure relates to the discovery that the expression level of particular miRNAs is associated with the presence, development, progression and severity of endometriosis. In various embodiments, the disclosure relates to a genetic screening assay of a subject to determine the level of expression of at least one miRNA associated with endometriosis in the subject. The present disclosure provides methods of assessing level of at least one miRNA associated with endometriosis, as well as methods of diagnosing a subject as having, or as being at risk of developing, endometriosis based upon the level of expression of at least one miRNA associated with endometriosis. In some embodiments, the diagnostic assays described herein are in vitro assays.

In some embodiments, the method of the disclosure is a diagnostic assay for assessing the presence, development, progression and severity of endometriosis in a subject in need thereof, by determining whether the level of at least one miRNA associated with endometriosis is decreased in a biological sample obtained from the subject. In various embodiments, to determine whether the level of the at least one miRNA associated with endometriosis is decreased in a biological sample obtained from the subject, the level of the at least one miRNA is compared with the level of at least one comparator control, such as a positive control, a negative control, a normal control, a wild-type control, a historical control, a historical norm, or the level of another reference molecule in the biological sample. In some embodiments, the diagnostic assay of the disclosure is an in vitro assay. In other embodiments, the diagnostic assay of the disclosure is an in vivo assay. The miRNA identified by the assay can be any miRNA that is associated with endometriosis. In some embodiments, the miRNA is at least one of miR-125, miR-150, miR-342, miR-145, miR-143, miR-500, miR-451, miR-18, miR-214, miR-126, miR-6755, miR-3613, miR-553, and miR-4668. The miRNA identified by the assay can be any miRNA that is associated with endometriosis. In some embodiments, the miRNA is at least one of miR-125b-5p, miR-150-5p, miR-342-3p, miR-145-5p, miR-143-3p, miR-500a-3p, miR-451a, miR-18a-5p, miR-214-3p, miR-126-3p, miR-6755-3p, miR-3613-5p, miR-553, and miR-4668-3p. In various embodiments of the disclosure, the at least one miRNA associated with endometriosis is at least two miRNAs, at least three miRNAs, at least four miRNAs, at least five miRNAs, at least six miRNAs, at least seven miRNAs, at least eight miRNAs. The results of the diagnostic assay can be used alone, or in combination with other information from the subject, or other information from the biological sample obtained from the subject.

In various embodiments of the assays of the disclosure, the level of the at least one miRNA associated with endometriosis is determined to be down-regulated when the level of the at least one miRNA is decreased by at least 10%, by at least 20%, by at least 30%, by at least 40%, by at least 50%, by at least 60%, by at least 70%, by at least 80%, by at least 90%, by at least 100%, by at least 125%, by at least 150%, by at least 175%, by at least 200%, by at least 250%, by at least 300%, by at least 400%, by at least 500%, by at least 600%, by at least 700%, by at least 800%, by at least 900%, by at least 1000%, by at least 1500%, by at least 2000%, or by at least 5000%, when compared with a comparator control.

In various embodiments of the assays of the disclosure, the level of the at least one miRNA associated with endometriosis is determined to be up-regulated when the level of the at least one miRNA is increased by at least 10%, by at least 20%, by at least 30%, by at least 40%, by at least 50%, by at least 60%, by at least 70%, by at least 80%, by at least 90%, by at least 100%, by at least 125%, by at least 150%, by at least 175%, by at least 200%, by at least 250%, by at least 300%, by at least 400%, by at least 500%, by at least 600%, by at least 700%, by at least 800%, by at least 900%, by at least 1000%, by at least 1500%, by at least 2000%, or by at least 5000%, when compared with a comparator control.

In various embodiments of the assays of the disclosure, the level of the at least one miRNA associated with endometriosis is determined to be down-regulated when the level of the at least one miRNA is decreased by at least 1.5-fold, at least 2-fold, at least 3-fold, at least 5-fold, at least 10-fold, at least 25-fold, at least 50-fold, at least 100-fold, at least 150-fold, at least 200-fold, or at least 500-fold, when compared with a comparator control. In various embodiments of the assays of the disclosure, the level of the at least one miRNA associated with endometriosis is determined to be up-regulated when the level of the at least one miRNA is increased by at least 1.5-fold, at least 2-fold, at least 3-fold, at least 5-fold, at least 10-fold, at least 25-fold, at least 50-fold, at least 100-fold, at least 150-fold, at least 200-fold, or at least 500-fold, when compared with a comparator control.

In the assay methods of the disclosure, a test biological sample from a subject is assessed for the expression level of at least one miRNA associated with endometriosis. The test biological sample can be an in vitro sample or an in vivo sample. In various embodiments, the subject is a human subject, and may be of any race, sex and age. Representative subjects include those who are suspected of having endometriosis, those who have been diagnosed with endometriosis, those whose have endometriosis, those who have had endometriosis, those who at risk of a recurrence of endometriosis, and those who are at risk of developing endometriosis.

In some embodiments, an endometriosis associated miRNA-binding molecule is used in vivo for the diagnosis of endometriosis. In some embodiments, the endometriosis associated miRNA-binding molecule is nucleic acid that hybridizes with an endometriosis associated miRNA of the disclosure.

In some embodiments, the test sample is a sample containing at least a fragment of a nucleic acid comprising a miRNA associated with endometriosis. The term, "fragment," as used herein, indicates that the portion of a nucleic acid (e.g., DNA, mRNA or cDNA) that is sufficient to identify it as comprising a miRNA associated with endometriosis.

In some embodiments, the test sample is prepared from a biological sample obtained from the subject. The biological sample can be a sample from any source which contains a nucleic acid comprising endometriosis associated miRNA, such as a body fluid (e.g., blood, plasma, serum, saliva, urine, etc.), or a tissue, or an exosome, or a cell, or a combination thereof. A biological sample can be obtained by appropriate methods, such as, by way of examples, biopsy or fluid draw. The biological sample can be used as the test sample; alternatively, the biological sample can be processed to enhance access to polypeptides, nucleic acids, or copies of nucleic acids (e.g., copies of nucleic acids comprising a miRNA associated with endometriosis), and the processed biological sample can then be used as the test sample. For example, in various embodiments, nucleic acid is prepared from a biological sample, for use in the methods. Alternatively, or in addition, if desired, an amplification method can be used to amplify nucleic acids comprising all or a fragment of a nucleic acid in a biological sample, for use as the test sample in the assessment of the expression level of a miRNA associated with endometriosis.

The test sample is assessed to determine the level of expression of at least one miRNA associated with endometriosis present in the nucleic acid of the subject. In general, detecting a miRNA may be carried out by determining the presence or absence of a nucleic acid containing a miRNA of interest in the test sample.

In some embodiments, hybridization methods, such as Northern analysis, or in situ hybridizations, can be used (see Current Protocols in Molecular Biology, 2012, Ausubel, F. et al., eds., John Wiley & Sons, including all supplements). For example, the presence of a miRNA associated with endometriosis can be indicated by hybridization to a nucleic acid probe. A "nucleic acid probe," as used herein, can be a nucleic acid probe, such as a DNA probe or an RNA probe. For representative examples of use of nucleic acid probes, see, for example, U.S. Pat. Nos. 5,288,611 and 4,851,330.

To detect at least one miRNA of interest, a hybridization sample is formed by contacting the test sample with at least one nucleic acid probe. A preferred probe for detecting miRNA is a labeled nucleic acid probe capable of hybridizing to miRNA. The nucleic acid probe can be, for example, a full-length nucleic acid molecule, or a portion thereof, such as an oligonucleotide of at least 10, 15, or 25 nucleotides in length and sufficient to specifically hybridize under stringent conditions to appropriate miRNA. The hybridization sample is maintained under conditions which are sufficient to allow specific hybridization of the nucleic acid probe to a miRNA target of interest. Specific hybridization can be performed under high stringency conditions or moderate stringency conditions, as appropriate. In a preferred embodiment, the hybridization conditions for specific hybridization are high stringency. Specific hybridization, if present, is then detected using standard methods. If specific hybridization occurs between the nucleic acid probe and a miRNA in the test sample, the sequence that is present in the nucleic acid probe is also present in the miRNA of the subject. More than one nucleic acid probe can also be used concurrently in this method. Specific hybridization of any one of the nucleic acid probes is indicative of the presence of the miRNA of interest, as described herein.

Alternatively, a peptide nucleic acid (PNA) probe can be used instead of a nucleic acid probe in the hybridization methods described herein. PNA is a DNA mimic having a peptide-like, inorganic backbone, such as N-(2-aminoethyl) glycine units, with an organic base (A, G, C, T or U) attached to the glycine nitrogen via a methylene carbonyl linker (see, for example, 1994, Nielsen et al., Bioconjugate Chemistry 5:1). The PNA probe can be designed to specifically hybridize to a nucleic acid sequence comprising at least one miRNA of interest. Hybridization of the PNA probe to a nucleic acid sequence is indicative of the presence of a miRNA of interest.

Direct sequence analysis can also be used to detect miRNAs of interest. A sample comprising nucleic acid can be used, and PCR or other appropriate methods can be used to amplify all or a fragment of the nucleic acid, and/or its flanking sequences, if desired.

In another embodiment, arrays of oligonucleotide probes that are complementary to target nucleic acid sequences from a subject can be used to detect, identify and quantify miRNAs associated with endometriosis. For example, in some embodiments, an oligonucleotide array can be used. Oligonucleotide arrays typically comprise a plurality of different oligonucleotide probes that are coupled to a surface of a substrate in different known locations. These oligonucleotide arrays, also known as "Genechips," have been generally described in the art, for example, U.S. Pat. No. 5,143,854 and PCT patent publication Nos. WO 90/15070 and 92/10092. These arrays can generally be produced using mechanical synthesis methods or light directed synthesis methods which incorporate a combination of photolithographic methods and solid phase oligonucleotide synthesis methods. See Fodor et al., Science, 251:767-777 (1991), Pirrung et al., U.S. Pat. No. 5,143,854 (see also PCT Application No. WO 90/15070) and Fodor et al., PCT Publication No. WO 92/10092 and U.S. Pat. No. 5,424,186. Techniques for the synthesis of these arrays using mechanical synthesis methods are described in, e.g., U.S. Pat. No. 5,384,261.

After an oligonucleotide array is prepared, a sample containing miRNA is hybridized with the array and scanned for miRNAs. Hybridization and scanning are generally carried out by methods described herein and also in, e.g., Published PCT Application Nos. WO 92/10092 and WO 95/11995, and U.S. Pat. No. 5,424,186, the entire teachings of which are incorporated by reference herein.

In brief, a target miRNA sequence is amplified by well-known amplification techniques, e.g., RT, PCR. Typically, this involves the use of primer sequences that are complementary to the target miRNA. Amplified target, generally incorporating a label, is then hybridized with the array under appropriate conditions. Upon completion of hybridization and washing of the array, the array is scanned to determine the position on the array to which the target sequence hybridizes. The hybridization data obtained from the scan is typically in the form of fluorescence intensities as a function of location on the array.

Other methods of nucleic acid analysis can be used to detect miRNAs of interest. Representative methods include direct manual sequencing (1988, Church and Gilbert, Proc. Natl. Acad. Sci. USA 81:1991-1995; 1977, Sanger et al., Proc. Natl. Acad. Sci. 74:5463-5467; Beavis et al. U.S. Pat. No. 5,288,644); automated fluorescent sequencing; single-stranded conformation polymorphism assays (SSCP); clamped denaturing gel electrophoresis (CDGE); denaturing gradient gel electrophoresis (DGGE) (Sheffield et al., 1981, Proc. Natl. Acad. Sci. USA 86:232-236), mobility shift analysis (Orita et al., 1989, Proc. Natl. Acad. Sci. USA 86:2766-2770; Rosenbaum and Reissner, 1987, Biophys. Chem. 265:1275; 1991, Keen et al., Trends Genet. 7:5); RNase protection assays (Myers, et al., 1985, Science 230: 1242); Luminex xMAP™ technology; high-throughput sequencing (HTS) (Gundry and Vijg, 2011, Mutat Res, doi:10.1016/j.mrfmmm.2011.10.001); next-generation sequencing (NGS) (Voelkerding et al., 2009, Clinical Chemistry 55:641-658; Su et al., 2011, Expert Rev Mol Diagn. 11:333-343; Ji and Myllykangas, 2011, Biotechnol Genet Eng Rev 27:135-158); and/or ion semiconductor sequencing (Rusk, 2011, Nature Methods doi:10.1038/nmeth.f.330; Rothberg et al., 2011, Nature 475:348-352). These and other methods, alone or in combination, can be used to detect and quantify of at least one miRNA of interest, in a biological sample obtained from a subject. In some embodiments of the disclosure, the methods of assessing a biological sample to detect and quantify a miRNA of interest, as described herein, are used to diagnose, assess and characterize endometriosis in a subject in need thereof.

In some embodiments, sequencing can be performed using a next generation sequencing assay. As used herein, the term "next generation" is well-understood in the art and generally refers to any high-throughput sequencing approach including, but not limited to one or more of the following: massively-parallel signature sequencing, pyrosequencing (e.g., using a Roche 454 sequencing device), Illumina (Solexa) sequencing, sequencing by synthesis (Illumina), Ion torrent sequencing, sequencing by ligation (e.g., SOLiD sequencing), single molecule real-time (SMRT) sequencing (e.g., Pacific Bioscience), polony sequencing, DNA nanoball sequencing, heliscope single molecule sequencing (Helicos Biosciences), and nanopore sequencing (e.g., Oxford Nanopore). In some cases, the sequencing assay uses nanopore sequencing. In some cases, the sequencing assay includes some form of Sanger sequencing. In some cases, the sequencing involves shotgun sequencing; in some cases, the sequencing includes bridge PCR. In some cases, the sequencing is broad spectrum. In some cases, the sequencing is targeted.

The probes and primers according to the disclosure can be labeled directly or indirectly with a radioactive or nonradioactive compound, by methods well known to those skilled in the art, in order to obtain a detectable and/or quantifiable signal; the labeling of the primers or of the probes according to the disclosure is carried out with radioactive elements or with nonradioactive molecules. Among the radioactive isotopes used, mention may be made of $^{32}P$, $^{33}P$, $^{35}S$ or $^{3}H$. The nonradioactive entities are selected from ligands such as biotin, avidin, streptavidin or digoxigenin, haptenes, dyes, and luminescent agents such as radioluminescent, chemoluminescent, bioluminescent, fluorescent or phosphorescent agents.

Nucleic acids can be obtained from the biological sample using known techniques. Nucleic acid herein includes RNA, including mRNA, miRNA, etc. The nucleic acid can be double-stranded or single-stranded (i.e., a sense or an antisense single strand) and can be complementary to a nucleic acid encoding a polypeptide. The nucleic acid content may also be obtained from an extraction performed on a fresh or fixed biological sample.

There are many methods known in the art for the detection of specific nucleic acid sequences and new methods are continually reported. A great majority of the known specific nucleic acid detection methods utilize nucleic acid probes in specific hybridization reactions.

In the Northern blot, the nucleic acid probe is preferably labeled with a tag. That tag can be a radioactive isotope, a fluorescent dye or the other well-known materials. Another type of process for the specific detection of nucleic acids of exogenous organisms in a body sample known in the art are the hybridization methods as exemplified by U.S. Pat. Nos. 6,159,693 and 6,270,974, and related patents. To briefly summarize one of those methods, a nucleic acid probe of at least 10 nucleotides, preferably at least 15 nucleotides, more preferably at least 25 nucleotides, having a sequence complementary to a desired region of the target nucleic acid of interest is hybridized in a sample, subjected to depolymerizing conditions, and the sample is treated with an ATP/luciferase system, which will luminesce if the nucleic sequence is present. In quantitative Northern blotting, levels of the polymorphic nucleic acid can be compared to wild-type levels of the nucleic acid.

A further process for the detection of hybridized nucleic acid takes advantage of the polymerase chain reaction (PCR). The PCR process is well known in the art (U.S. Pat. Nos. 4,683,195, 4,683,202, and 4,800,159). To briefly summarize PCR, nucleic acid primers, complementary to opposite strands of a nucleic acid amplification target nucleic acid sequence, are permitted to anneal to the denatured sample. A DNA polymerase (typically heat stable) extends the DNA duplex from the hybridized primer. The process is repeated to amplify the nucleic acid target. If the nucleic acid primers do not hybridize to the sample, then there is no corresponding amplified PCR product.

In PCR, the nucleic acid probe can be labeled with a tag as discussed before. Most preferably the detection of the duplex is done using at least one primer directed to the target nucleic acid. In yet another embodiment of PCR, the detection of the hybridized duplex comprises electrophoretic gel separation followed by dye-based visualization.

Nucleic acid amplification procedures by PCR are well known and are described in U.S. Pat. No. 4,683,202. Briefly, the primers anneal to the target nucleic acid at sites distinct from one another and in an opposite orientation. A primer annealed to the target sequence is extended by the enzymatic action of a heat stable polymerase. The extension product is then denatured from the target sequence by heating, and the process is repeated. Successive cycling of this procedure on both strands provides exponential amplification of the region flanked by the primers.

Amplification is then performed using a PCR-type technique, that is to say the PCR technique or any other related technique. Two primers, complementary to the target nucleic acid sequence are then added to the nucleic acid content along with a polymerase, and the polymerase amplifies the DNA region between the primers.

Amplification may refer to any method for increasing the number of copies of a nucleic acid sequence. For example, the amplification may be performed with a polymerase, e.g., in one or more polymerase chain reactions. Amplification may be performed using methods known in the art. These methods often depend on the product catalyzed formation of multiple copies of a nucleic acid or its complement. One of such methods is polymerase chain reaction (PCR), including AFLP (amplified fragment length polymorphism) PCR, allele-specific PCR, Alu PCR, assembly, asymmetric PCR, colony PCR, helicase dependent PCR, hot start PCR, inverse PCR, in situ PCR, intersequence-specific PCR or IS SR PCR, digital PCR, droplet digital PCR, linear-after-the-exponential-PCR or Late PCR, long PCR, nested PCR, real-time PCR, duplex PCR, multiplex PCR, quantitative PCR, or single cell PCR. Other amplification methods may also be used, including ligase chain reaction (LCR), nucleic acid sequence based amplification (NASBA), linear amplification, isothermal linear amplification, Q-beta-replicase method, 3SR, Transcription Mediated Amplification (TMA), Strand Displacement Amplification (SDA), or Rolling Circle Amplification (RCA).

Stem-loop RT-PCR is a PCR method that is useful in the methods of the disclosure to amplify and quantify miRNAs of interest (See Caifu et al., 2005, Nucleic Acids Research 33:e179; Mestdagh et al., 2008, Nucleic Acids Research 36:e143; Varkonyi-Gasic et al., 2011, Methods Mol Biol. 744:145-57). Briefly, the method includes two steps: RT and real-time PCR. First, a stem-loop RT primer is hybridized to a miRNA molecule and then reverse transcribed with a reverse transcriptase. Then, the RT products are quantified using conventional real-time PCR.

The expression specifically hybridizing in stringent conditions refers to a hybridizing step in the process of the disclosure where the oligonucleotide sequences selected as probes or primers are of adequate length and sufficiently unambiguous so as to minimize the amount of non-specific binding that may occur during the amplification. The oligonucleotide probes or primers herein described may be prepared by any suitable methods such as chemical synthesis methods.

Hybridization is typically accomplished by annealing the oligonucleotide probe or primer to the template nucleic acid under conditions of stringency that prevent non-specific binding but permit binding of this template nucleic acid which has a significant level of homology with the probe or primer.

Among the conditions of stringency is the melting temperature (Tm) for the amplification step using the set of primers, which is in the range of about 50° C. to about 95° C. Typical hybridization and washing stringency conditions depend in part on the size (i.e., number of nucleotides in length) of the template nucleic acid or the oligonucleotide probe, the base composition and monovalent and divalent cation concentrations (Ausubel et al., 1994, eds Current Protocols in Molecular Biology).

In a preferred embodiment, the process for determining the quantitative and qualitative profile according to the present disclosure is characterized in that the amplifications are real-time amplifications performed using a labeled probe, preferably a labeled hydrolysis-probe, capable of specifically hybridizing in stringent conditions with a segment of a nucleic acid sequence, or polymorphic nucleic acid sequence. The labeled probe is capable of emitting a detectable signal every time each amplification cycle occurs. The real-time amplification, such as real-time PCR, is well known in the art, and the various known techniques will be employed in the best way for the implementation of the present process. These techniques are performed using various categories of probes, such as hydrolysis probes, hybridization adjacent probes, or molecular beacons. The techniques employing hydrolysis probes or molecular beacons are based on the use of a fluorescence quencher/reporter system, and the hybridization adjacent probes are based on the use of fluorescence acceptor/donor molecules.

Hydrolysis probes with a fluorescence quencher/reporter system are available in the market, and are for example commercialized by the Applied Biosystems group (USA). Many fluorescent dyes may be employed, such as FAM dyes (6-carboxy-fluorescein), or any other dye phosphoramidite reagents.

Among the stringent conditions applied for any one of the hydrolysis-probes of the present disclosure is the Tm, which is in the range of about 50° C. to 95° C. Preferably, the Tm for any one of the hydrolysis-probes of the present disclosure is in the range of about 55° C. to about 80° C. Most preferably, the Tm applied for any one of the hydrolysis-probes of the present disclosure is about 75° C.

In another preferred embodiment, the process for determining the quantitative and qualitative profile according to the present disclosure is characterized in that the amplification products can be elongated, wherein the elongation products are separated relative to their length. The signal obtained for the elongation products is measured, and the quantitative and qualitative profile of the labeling intensity relative to the elongation product length is established.

The elongation step, also called a run-off reaction, allows one to determine the length of the amplification product. The length can be determined using conventional techniques, for example, using gels such as polyacrylamide gels for the separation, DNA sequencers, and adapted software. Because some mutations display length heterogeneity, some mutations can be determined by a change in length of elongation products.

In one aspect, the disclosure includes a primer that is complementary to a nucleic acid sequence of the miRNA of interest, and more particularly the primer includes 12 or more contiguous nucleotides substantially complementary to the sequence of the miRNA of interest. Preferably, a primer featured in the disclosure includes a nucleotide sequence sufficiently complementary to hybridize to a nucleic acid sequence of about 12 to 25 nucleotides. More preferably, the primer differs by no more than 1, 2, or 3 nucleotides from the target nucleotide sequence. In another aspect, the length of the primer can vary in length, preferably about 15 to 28 nucleotides in length (e.g., 15, 16, 17, 18, 19, 20, 21, 22, 23, 24, 25, 26, 27 or 28 nucleotides in length).

Determining Effectiveness of Therapy or Prognosis

In one aspect, the level of one or more circulating miRNAs in a biological sample of a patient is used to monitor the effectiveness of treatment or the prognosis of disease. In some embodiments, the level of one or more circulating miRNAs in a test sample obtained from a treated patient can be compared to the level from a reference sample obtained from that patient prior to initiation of a treatment. Clinical monitoring of treatment typically entails that each patient serve as his or her own baseline control. In some embodiments, test samples are obtained at multiple time points following administration of the treatment. In these embodiments, measurement of level of one or more circulating miRNAs in the test samples provides an indication of the extent and duration of in vivo effect of the treatment.

Measurement of biomarker levels allow for the course of treatment of a disease to be monitored. The effectiveness of a treatment regimen for a disease can be monitored by detecting one or more biomarkers in an effective amount from samples obtained from a subject over time and comparing the amount of biomarkers detected. For example, a first sample can be obtained prior to the subject receiving treatment and one or more subsequent samples are taken after or during treatment of the subject. Changes in biomarker levels across the samples may provide an indication as to the effectiveness of the therapy.

In some embodiments, the disclosure provides a method for monitoring the levels of miRNAs in response to treatment. For example, in certain embodiments, the disclosure provides for a method of determining the efficacy of treatment in a subject, by measuring the levels of one or more miRNAs described herein. In some embodiments, the level of the one or more miRNAs can be measured over time, where the level at one timepoint after the initiation of treatment is compared to the level at another timepoint after the initiation of treatment. In some embodiments, the level of the one or more miRNAs can be measured over time, where the level at one timepoint after the initiation of treatment is compared to the level prior to the initiation of treatment. In some embodiments, the disclosure provides a method for monitoring at least one of miR-125, miR-150, miR-342, miR-145, miR-143, miR-500, miR-451, miR-18, miR-214, miR-126, miR-6755, miR-3613, miR-553, and miR-4668 after treatment. In some embodiments, the disclosure provides a method for monitoring the levels of miR-125, miR-150, miR-3613 or any combination thereof after endometriosis treatment.

In some embodiments, the disclosure provides a method for monitoring at least one of miR-125b-5p, miR-150-5p, miR-342-3p, miR-145-5p, miR-143-3p, miR-500a-3p, miR-451a, miR-18a-5p, miR-214-3p, miR-126-3p, miR-6755-3p, miR-3613-5p, miR-553, and miR-4668-3p after treatment. In some embodiments, the disclosure provides a method for monitoring the levels of miR-125, miR-150, miR3613 or any combination thereof after endometriosis treatment.

In some embodiments, the disclosure provides a method for assessing the efficacy of an endometriosis treatment. For example, in some embodiments, the method indicates that the treatment is effective when the level of miR-125 is decreased in a sample of a treated subject as compared to a control diseased subject or population not receiving treatment. In some embodiments, the method indicates that the treatment is effective when the level of miR-150 is increased in a sample of a treated subject as compared to a control diseased subject or population not receiving treatment. In some embodiments, the method indicates that the treatment is effective when the level of miR-3613 is increased in a sample of a treated subject as compared to a control diseased subject or population not receiving treatment.

In some embodiments, the disclosure provides a method for assessing the efficacy of an endometriosis treatment. For example, in some embodiments, the method indicates that the treatment is effective when the level of miR-125b-5p is decreased in a sample of a treated subject as compared to a control diseased subject or population not receiving treatment. In some embodiments, the method indicates that the treatment is effective when the level of miR-150-5p is increased in a sample of a treated subject as compared to a control diseased subject or population not receiving treatment. In some embodiments, the method indicates that the treatment is effective when the level of miR-3613-5p is increased in a sample of a treated subject as compared to a control diseased subject or population not receiving treatment.

To identify therapeutics or drugs that are appropriate for a specific subject, a test sample from the subject can also be exposed to a therapeutic agent or a drug, and the level of one or more biomarkers can be determined. Biomarker levels can be compared to a sample derived from the subject before and after treatment or exposure to a therapeutic agent or a drug, or can be compared to samples derived from one or more subjects who have shown improvements relative to a disease as a result of such treatment or exposure. Thus, in one aspect, the disclosure provides a method of assessing the efficacy of a therapy with respect to a subject comprising taking a first measurement of a biomarker panel in a first sample from the subject; effecting the therapy with respect to the subject; taking a second measurement of the biomarker panel in a second sample from the subject and comparing the first and second measurements to assess the efficacy of the therapy.

Additionally, therapeutic agents suitable for administration to a particular subject can be identified by detecting one or more biomarkers in an effective amount from a sample obtained from a subject and exposing the subject-derived sample to a test compound that determines the amount of the biomarker(s) in the subject-derived sample. Accordingly, treatments or therapeutic regimens for use in subjects having endometriosis can be selected based on the amounts of biomarkers in samples obtained from the subjects and compared to a reference value. Two or more treatments or therapeutic regimens can be evaluated in parallel to determine which treatment or therapeutic regimen would be the most efficacious for use in a subject to delay onset, or slow progression of a disease. In various embodiments, a recommendation is made on whether to initiate or continue treatment of a disease.

A prognosis may be expressed as the amount of time a patient can be expected to survive. Alternatively, a prognosis may refer to the likelihood that the disease goes into remission or to the amount of time the disease can be expected to remain in remission. Prognosis can be expressed in various ways; for example, prognosis can be expressed as a percent chance that a patient will survive after one year, five years, ten years or the like. Alternatively, prognosis may be expressed as the number of years, on average that a patient can expect to survive as a result of a condition or disease. The prognosis of a patient may be considered as an expression of relativism, with many factors affecting the ultimate outcome. For example, for patients with certain conditions, prognosis can be appropriately expressed as the likelihood that a condition may be treatable or curable, or the likelihood that a disease will go into remission, whereas for patients with more severe conditions prognosis may be more appropriately expressed as likelihood of survival for a specified period of time. Additionally, a change in a clinical factor from a baseline level may impact a patient's prognosis, and the degree of change in level of the clinical factor may be related to the severity of adverse events. Statistical significance is often determined by comparing two or more populations, and determining a confidence interval and/or a p value.

Multiple determinations of circulating miRNA levels can be made, and a temporal change in activity can be used to determine a prognosis. For example, comparative measurements are made of the circulating miRNA of an acellular body fluid in a patient at multiple time points, and a comparison of a circulating miRNA value at two or more time points may be indicative of a particular prognosis.

In certain embodiments, the levels of activity of one or more circulating miRNAs are used as indicators of an unfavorable prognosis. According to the method, the determination of prognosis can be performed by comparing the measured circulating miRNA level to levels determined in comparable samples from healthy individuals or to levels known to corresponding with favorable or unfavorable outcomes. The circulating miRNA levels obtained may depend on a number of factors, including, but not limited to, the laboratory performing the assays, the assay methods used, the type of body fluid sample used and the type of disease a patient is afflicted with. According to the method, values can be collected from a series of patients with a particular disorder to determine appropriate reference ranges of circulating miRNA for that disorder. One of ordinary skill in the art is capable of performing a retrospective study that compares the determined levels to the observed outcome of the patients and establishing ranges of levels that can be used to designate the prognosis of the patients with a particular disorder. For example, levels in the lowest range would be indicative of a more favorable prognosis, while circulating miRNA levels in the highest ranges would be indicative of an unfavorable prognosis. Thus, in this aspect the term "elevated levels" refers to levels of that are above the range of the reference value. In some embodiments patients with "high" or "elevated" levels have levels that are higher than the median activity in a population of patients with that disease. In certain embodiments, "high" or "elevated" levels for a patient with a particular disease refers to levels that are above the median values for patients with that disorder and are in the upper 40% of patients with the disorder, or to levels that are in the upper 20% of patients with the disorder, or to levels that are in the upper 10% of patients with the disorder, or to levels that are in the upper 5% of patients with the disorder.

Because the level of circulating miRNA in a test sample from a patient relates to the prognosis of a patient in a continuous fashion, the determination of prognosis can be performed using statistical analyses to relate the determined circulating miRNA levels to the prognosis of the patient. A skilled artisan is capable of designing appropriate statistical methods. For example, the methods may employ the chi-squared test, the Kaplan-Meier method, the log-rank test, multivariate logistic regression analysis, Cox's proportional-hazard model and the like in determining the prognosis. Computers and computer software programs may be used in organizing data and performing statistical analyses. The approach by Giles et. al., British Journal of Hemotology, 121:578-585, is exemplary. As in Giles et al., associations between categorical variables (e.g., miRNA levels and clinical characteristics) can be assessed via cross-tabulation and Fisher's exact test. Unadjusted survival probabilities can be estimated using the method of Kaplan and Meier. The Cox proportional hazards regression model also can be used to assess the ability of patient characteristics (such as miRNA levels) to predict survival, with 'goodness of fit' assessed by the Grambsch-Therneau test, Schoenfeld residual plots, martingale residual plots and likelihood ratio statistics (see Grambsch et al, 1995). In some embodiments, this approach can be adapted as a simple computer program that can be used with personal computers or personal digital assistants (PDA). The prediction of patients' survival time in based on their circulating miRNA levels can be performed via the use of a visual basic for applications (VBA) computer program developed within Microsoft Excel. The core construction and analysis may be based on the Cox proportional hazard models. The VBA application can be developed by obtaining a base hazard rate and parameter estimates. These statistical analyses can be performed using a statistical program such as the SAS proportional hazards regression, PHREG, procedure. Estimates can then be used to obtain probabilities of surviving from one to 24 months given the patient's covariates. The program can make use of estimated probabilities to create a graphical representation of a given patient's predicted survival curve. In certain embodiments, the program also provides 6-month, 1-year and 18-month survival probabilities. A graphical interface can be used to input patient characteristics in a user-friendly manner. In some embodiments of the disclosure, multiple prognostic factors, including circulating miRNA level, are considered when determining the prognosis of a patient. For example, the prognosis of an endometriosis subject or may be determined based on the presence of miRNA in a body fluid and one or more prognostic factors selected from the group consisting of cytogenetics, performance status, age, gender and previous diagnosis. In another example, the prognosis of a cancer patient may be determined based on circulating miRNA and one or more prognostic factors selected from the group consisting of cytogenetics, performance status, age, gender and previous diagnosis. In certain embodiments, other prognostic factors may be combined with the circulating miRNA level or other biomarkers in the algorithm to determine prognosis with greater accuracy.

Treatment

The present disclosure provides therapeutic molecules for the treatment or prevention of endometriosis. In some embodiments, the therapeutic molecules include but are not limited to inhibitors, activators, and modulators of the markers of the disclosure. For example, if a gene is downregulated in endometriosis, than it would be desirable to increase the expression of the downregulated gene to normal levels using an activator as a form of therapy. Activators are compounds that increase, open, activate, facilitate, enhance activation, sensitize, agonize, or up regulate activity of endometriosis biomarkers. Alternatively, if a gene is upregulated in endometriosis, than it would be desirable to decrease the expression of the upregulated gene to normal levels using an inhibitor as a form of therapy. Inhibitors are compounds that, e.g., bind to, partially or totally block activity, decrease, prevent, delay activation, inactivate, desensitize, or down regulate the activity or expression of endometriosis biomarkers.

Methods and materials for increasing or decreasing the expression levels of the markers of the present disclosure are well known and within the skill of a person in the art. A non-limitative list of known methods and materials includes: diet, vitamins, dietary supplements, gene therapy methods, antisense oligonucleotides, drugs and hormonal medications.

The disclosure provides a method of treating endometriosis by targeting the miRNAs described herein. For example, in some embodiments, the disclosure provides a method of treating endometriosis in a subject comprising administering an agent that increases the expression or level of one more miRNAs described herein. For example, in some embodiments, the method comprises administering an agent that increases the expression or level of one more of miR-6755, miR3613, miR-553, and miR-4668. In some embodiments, the disclosure provides a method of treating endometriosis in a subject comprising administering an agent that decreases the expression or level of one more miRNAs described herein. For example, in some embodiments, the method comprises administering an agent that decreases the expression or level of one more of miR-125, miR-150, miR-342, miR-145, miR-143, miR-500, miR-451, miR-18, miR-214, and miR-126.

The disclosure provides a method of treating endometriosis by targeting the miRNAs described herein. For example, in some embodiments, the disclosure provides a method of treating endometriosis in a subject comprising administering an agent that increases the expression or level of one more miRNAs described herein. For example, in some embodiments, the method comprises administering an agent that increases the expression or level of one more of miR-6755-3p, miR3613-5p, miR-553, and miR-4668-3p. In some embodiments, the disclosure provides a method of treating endometriosis in a subject comprising administering an agent that decreases the expression or level of one more miRNAs described herein. For example, in some embodiments, the method comprises administering an agent that decreases the expression or level of one more of miR-125b-5p, miR-150-5p, miR-342-3p, miR-145-5p, miR-143-3p, miR-500a-3p, miR-451a, miR-18a-5p, miR-214-3p, and miR-126-3p.

Once a patient is diagnosed with having or is at risk of having endometriosis, the patient can be treated using methods known in the art. Well known treatments for endometriosis include, but are not limited to, pain killers, hormonal treatments, chemotherapy, and surgical treatments. Pain killers used for the treatment of endometriosis include both simple analgesics, such as paracetamol, COX-2 inhibitors, aspirin, and other non-steroidal anti-inflammatory drugs well known in the art, and narcotic analgesics, such as morphine, codine, oxycodone, and others well known in the art. Hormonal treatments include, but are not limited to, oral contraceptives, progestins, such as Dydrogesterone, Medroxyprogesterone acetate, Depot medroxyprogesterone acetate, Norethisterone, Levonorgestrel, and others well known in the art, progesterone and progesterone-like substances, GnRH agonists, such as leuprorelin, buserelin, goserelin, histrelin, deslorelin, nafarelin, and triptorelin, androgens and synthetic androgens like Danazol, and aromatase inhibitors. Surgical treatments include, but are not limited to, laparoscopic surgery, hysterectomy, and oophorectomy. Other treatments particularly well suited for use in the present disclosure are well known in the art. In some embodiments, the patient can be treated using a statin, including but not limited to, atorvastatin, cerivastatin, fluvastatin, lovastatin, mevastatin, pitavastatin, pravastatin, rosuvastatin and simvastatin.

Kits

The present disclosure also pertains to kits useful in the methods of the disclosure. Such kits comprise components useful in any of the methods described herein, including for example, hybridization probes or primers (e.g., labeled probes or primers), reagents for detection of labeled molecules, oligonucleotide arrays, restriction enzymes, antibodies, allele-specific oligonucleotides, means for amplification of a subject's nucleic acids, means for reverse transcribing a subject's RNA, means for analyzing a subject's nucleic acid sequence, and instructional materials. For example, in some embodiments, the kit comprises components useful for the detection and quantification of at least one miRNA associated with endometriosis. In a preferred embodiment of the disclosure, the kit comprises components for detecting one or more of the miRNAs associated with endometriosis as elsewhere described herein.

The present disclosure also provides kits for diagnosing endometriosis or reduced fertility caused by endometriosis, comprising a probe for one or more nucleic acid biomarkers known to be differentially expressed in endometriosis. In one particular embodiment, the kit comprises reagents for quantitative amplification of the selected biomarkers. Alternatively, the kit may comprise a microarray. In some embodiments the kit comprises 2 or more probes. In other embodiments, the kits may contain 3, 4, 5, 6, 7, 8, 9, 10, 15, 20, 25, or more probes.

The present disclosure also pertains to kits useful in the methods of the disclosure. Such kits comprise various combinations of components useful in any of the methods described elsewhere herein, including for example, materials for quantitatively analyzing a biomarker of the disclosure (e.g., polypeptide and/or nucleic acid), materials for assessing the activity of a biomarker of the disclosure (e.g., polypeptide and/or nucleic acid), and instructional material. For example, in some embodiments, the kit comprises components useful for the quantification of a desired nucleic acid in a biological sample.

In a further embodiment, the kit comprises the components of an assay for monitoring the effectiveness of a treatment administered to a subject in need thereof, containing instructional material and the components for determining whether the level of a biomarker of the disclosure in a biological sample obtained from the subject is modulated during or after administration of the treatment. In various embodiments, to determine whether the level of a biomarker of the disclosure is modulated in a biological sample obtained from the subject, the level of the biomarker is compared with the level of at least one comparator control contained in the kit, such as a positive control, a negative control, a historical control, a historical norm, or the level of another reference molecule in the biological sample. In certain embodiments, the ratio of the biomarker and a reference molecule is determined to aid in the monitoring of the treatment.

EXPERIMENTAL EXAMPLES

The disclosure is further described in detail by reference to the following experimental examples. These examples are provided for purposes of illustration only, and are not intended to be limiting unless otherwise specified. Thus, the disclosure should in no way be construed as being limited to the following examples, but rather, should be construed to encompass any and all variations which become evident as a result of the teaching provided herein.

Without further description, it is believed that one of ordinary skill in the art can, using the preceding description and the following illustrative examples, make and utilize the present disclosure and practice the claimed methods. The following working examples therefore, specifically point out the preferred embodiments of the present disclosure, and are not to be construed as limiting in any way the remainder of the disclosure.

Example 1: Serum Micro RNAs as Diagnostic Markers of Endometriosis; a Comprehensive Array Based Analysis Microarray studies from eutopic and ectopic endometrial tissue of women with and without endometriosis show differential expression of several miRNAs (Ohlsson et al., 2009, Mol Endocrinol, 23:265-275, Petracco et al., 2011, J Clin Endocrinol Metab, 96:E1925-1933). They play an important role in the pathogenesis of endometriosis and related infertility by regulating gene expression (Teague et al., 2010, Hum Reprod Update, 16:142-165). The tissue miRNAs are shed from the pathologic tissues to the circulation, and a strong correlation has been shown between circulating and tissue levels (Resnick et al., 2009, Gynecol Oncol, 112:55-59). Several differentially expressed miRNA have been identified in serum of endometriosis patients (Jia et al., 2013, Hum Reprod, 28:322-330, Wang et al., 2013, J Clin Endocrinol Metab, 98:281-289). Previously it has been demonstrated that let-7b and miR-135a were differentially expressed in the serum from endometriosis patients and are useful biomarkers of the disease (Cho et al., 2015, Fertil Steril, 103(5):1252-1260). In this study, it has been demonstrated that other miRNAs are markers of this disease. This study, is a comprehensive evaluation of the global miRNA profile in serum of women with endometriosis and identifying several miRNAs used as noninvasive biomarkers of the disease.

The materials and methods employed in these experiments are now described.

Study Population

Serum samples were collected from 48 women with and without endometriosis. The study population was selected from patients that underwent laparascopy for multiple benign indications including pelvic masses, pelvic pain, infertility, and endometriosis between June 2010 and March 2013. Patients gave informed consent to participate in the study. Criteria for inclusion were age 20 to 50 years, no hormonal therapy for at least 3 months preceding surgery, no other inflammatory disease. The exclusion criteria included postmenopausal status, previous hormone or gonadotropin-releasing hormone (GnRH) agonist use within 3 months of the surgery, adenomyosis, endometrial cancer, hyperplasia, or endometrial polyps, infectious diseases, chronic or acute inflammatory diseases, malignancy, autoimmune disease, and cardiovascular disease. Pretreatment serum CA-125 levels in all patients were measured using CA-125 II electrochemiluminescence immunoassay (ECLIA) with the Roche/Hitachi Modular Analytics E170 system (Roche Diagnostics). During surgery, all possible endometriotic lesions were excised and examined for the final diagnosis. Patients were assigned to the endometriosis group after pathologic confirmation of the excised tissue. The extent of endometriosis was determined using the American Society of Reproductive Medicine (ASRM) revised classification (Revised American Society for Reproductive Medicine classification of endometriosis. Fertil Steril 1996, 67:817-821). Twenty-four patients had histologically confirmed peritoneal and/or ovarian endometriosis, with moderate-to-severe disease (stages III and IV). Twenty-four patients participated as controls, which included 10 cases of dermoid cysts (n=10), serous cystadenoma (n=5), mucinous cystadenoma (n=3), simple ovarian cysts (n=5), and paratubal cysts (n=1).

Sample Collection and RNA Extraction

Blood samples (10 ml) were collected after 8 hours of fasting before surgery. Sterile tubes containing no additives were used. The samples were immediately centrifuged and the serums were frozen at −80° C. for further analysis. Half of the sample from each individual were pooled for microarray analysis and the remaining half of the sample was used for individual analysis of micro RNAs. The total RNA was extracted from 400 µl of serum using the miRVana RNA Isolation Kit (Applied Biosystems) according to the manufacturer's specifications and was eluted with 50 ml of nuclease-free water. The yield of RNA was determined using a Nano Drop ND-2000-spectrophotometer (Nano drop Technologies, USA).

miRNA Microarray Expression Profiling

Total RNAs from the pooled samples of women with endometriosis and controls were used for microRNA microarray profiling. Total RNA (100 ng) was labeled with the microRNA. Complete Labeling and Hyb Kit (Affymetrix, USA) and hybridized on the Human microRNA Microarray Kit (Release 16.0, Affymetrix), which contains 60000 probes for 1205 human and 144 human viral microRNAs. Hybridization signals were detected with the Affymetrix Microarray Scanner (Affymetrix) and the scanned images were analyzed using Affymetrix Feature Extraction Software (Affymetrix).

Quantitative Real-Time Polymerase Chain Reaction for miRNAs

Invitrogen NCode miRNA First-Strand cDNA Synthesis MIRC-50 kit (Life Technologies) following the manufacturer's instructions. Total RNA (25 ng) from each sample was reverse transcribed, and the miRNAs were quantified using the iQ SYBR Green supermix kit (Bio-Rad Laboratories) with the specific forward primers for miR-125b-5p (SEQ ID NO:37), miR-150-5p (SEQ ID NO:38), miR-342-3p (SEQ ID NO:39), miR-145-5p (SEQ ID NO:40), miR-143-3p (SEQ ID NO:41), miR-500a-3p (SEQ ID NO:42), miR-451a (SEQ ID NO:43), miR-18a-5p (SEQ ID NO:44), miR-6755-3p (SEQ ID NO:45), miR-3613-5p (SEQ ID NO:46), miR-553 (SEQ ID NO:47), miR-4668-3p (SEQ ID NO:48) and the universal reverse primer complementary to the anchor primer:

```
                                        (SEQ ID NO: 37)
miR-125b-5p forward UCCCUGAGACCCUAACUUGUGA;

(SEQ ID NO: 38)
miR-150-5p forward UCUCCCAACCCUUGUACCAGUG;

(SEQ ID NO: 39)
miR-342-3p forward UCUCACACAGAAAUCGCACCCGU;

(SEQ ID NO: 40)
miR-145-5p forward GUCCAGUUUUCCCAGGAAUCCCU;

(SEQ ID NO: 41)
miR-143-3p forward UGAGAUGAAGCACUGUAGCUC;

(SEQ ID NO: 42)
miR-500a-3p forward AUGCACCUGGGCAAGGAUUCUG;

(SEQ ID NO: 43)
miR-451a forward AAACCGUUACCAUUACUGAGUU;

(SEQ ID NO: 44)
miR-18a-5p forward UAAGGUGCAUCUAGUGCAGAUAG;

(SEQ ID NO: 45)
miR-6755-3p forward UGUUGUCAUGUUUUUUCCCUAG;

(SEQ ID NO: 46)
miR-3613-5p forward UGUUGUACUUUUUUUUUUGUUC;

(SEQ ID NO: 47)
miR-553 forward AAAACGGUGAGAUUUUGUUUU;

(SEQ ID NO: 48)
miR-4668-3p forward GAAAAUCCUUUUUGUUUUUCCAG;

(SEQ ID NO: 49)
miR-214-3p forward ACAGCAGGCACAGACAGGCAGU;

(SEQ ID NO: 50)
miR-126-3p forward UCGUACCGUGAGUAAUAAUGCG;
```

The reaction mixture included 4 µl of cDNA, 5 µl of iQSYBR Green Supermix, 0.5 µl of forward primer, 0.5 µl of universal quantitative polymerase chain reaction primer for a final reaction volume of 10 µl. The thermal cycling conditions were initiated by uracil-N-glycosylase activation at 50° C. for 2 minutes and initial denaturation at 95° C. for 15 minutes, followed by 50 cycles at 95° C. for 15 seconds and annealing at 59° C. for 50 seconds. Threshold cycle and melting curves were acquired by using the quantitation and melting curve program of the Bio-Rad iCycleri Qsystem (Bio-Rad Laboratories). Anchor reverse-transcription primer was used as the template for negative control, and U6 (U6 forward, CTCGCTTCGGCAGCACA) (SEQ ID NO:51) small nuclear RNA was used as a control to determine relative miRNA expression (Kuwabara et al., 2011, Circ Cardiovasc Genet, 4:446-454). The relative mRNA level was determined using comparative cycle threshold (Ct) method (known as $2^{\Delta\Delta CT}$ method).

Statistical Analysis

Student's t-test and Fisher's exact test were used determine the statistical significance of differences in clinical characteristics between the endometriosis and control groups. The expression levels of serum miRNAs between the groups were compared using the Mann-Whitney U test. Receiver operating characteristics (ROC) curves and the area under the ROC curve (AUC) were established to evaluate the diagnostic value of plasma microRNAs for differentiating between endometriosis and controls. Based on ROC analysis, the best statistical cut-off values of plasma miRNAs was calculated, and the sensitivity and specificity for selected cut-off points were then assessed. All statistical analysis was performed using SPSS 16.0 (SPSS Inc, Chicago, IL). $P<0.05$ was considered statistically significant.

The results of the experiments are now described.

Clinical Characteristics

The mean (±SD) age of the women with endometriosis was 33.08±6.63 years and 32.16±9.46 years of controls (p>0.05). There was also no statistically significant difference between the other clinical parameters including gravidity, parity, alcohol usage and other comorbidities. Pelvic pain intensity of the endometriosis group determined with VAS (visual analogue scale) was higher than the control group (5.4±3.4, 2.1±2.4 respectively, p<0.001). CA-125 values were significantly higher in endometriosis group than control group but highly variable (103.3±121.7, 17.5±6.3 respectively, p<0.003). All women with endometriosis had ovarian endometriosis, 16 of them had peritoneal disease and 8 of them had deep infiltrating endometriosis.

Expression of Circulating miRNAs in Serum of Study Population

Affymetrix miRNA 4.0 Arrays were used to detect miRNA profile of the pooled samples and analyzed a total of 36,354 miRNAs from these array studies. Out of these miRNAs 11,653 were down regulated and 10,010 were upregulated. Differentially expressed miRNAs with more than 10-fold change in their expression between the endometriosis and the control groups were selected (FIG. 1). As shown in FIG. 1, miR-125b-5p, miR-150-5p, miR-342-3p, miR-145-5p, miR-143-3p, miR-500a-3p, miR-451a, miR-18a-5p were upregulated while miR-3613-5p, and miR-6755-3p were down regulated.

Figure 2A:
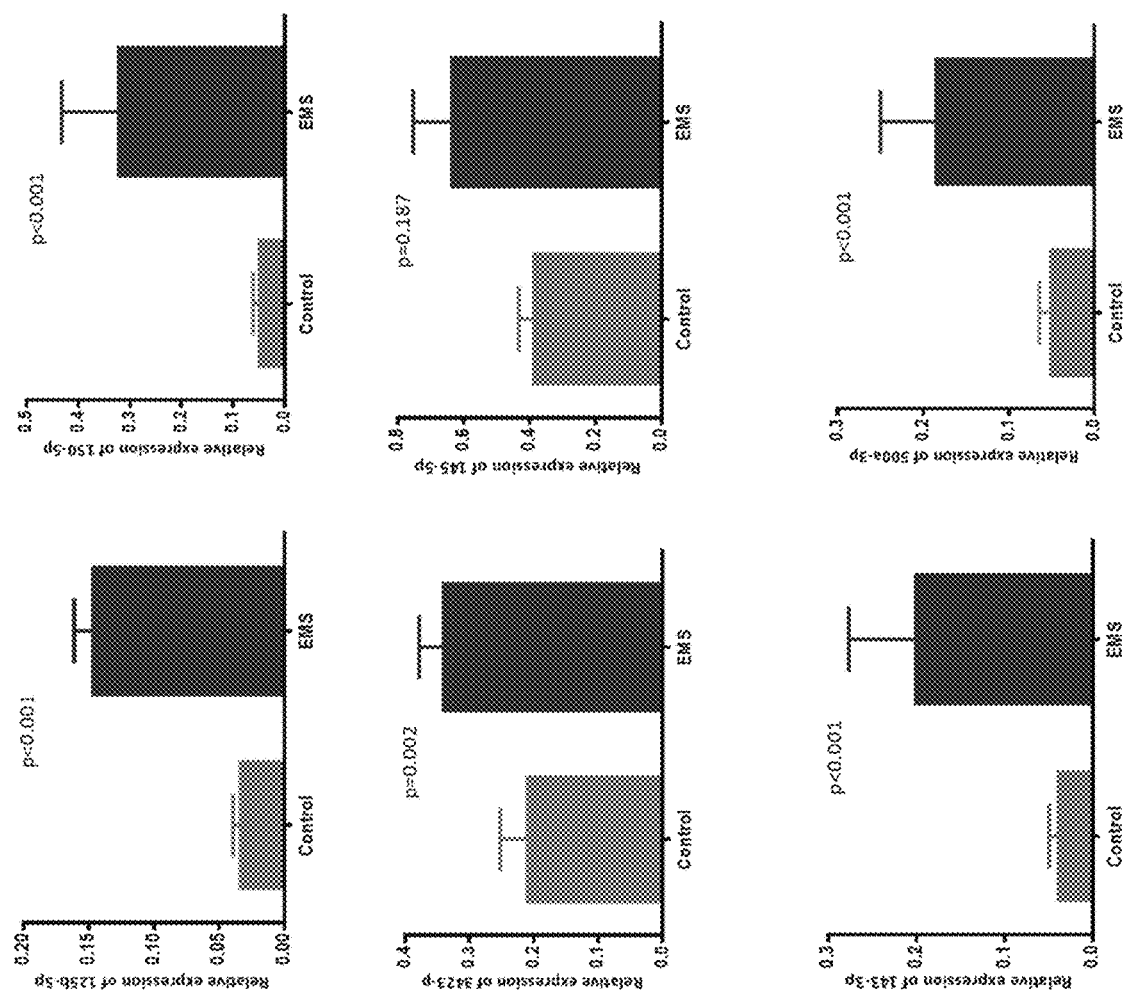
FIG. 2A and FIG. 2B, is a set of images depicting the results of differentially expressed miRNAs in the endometriosis and control groups as determined by real time quantitative PCR. p-values based on analysis using the Mann-Whitney U test.
Figure 2B:
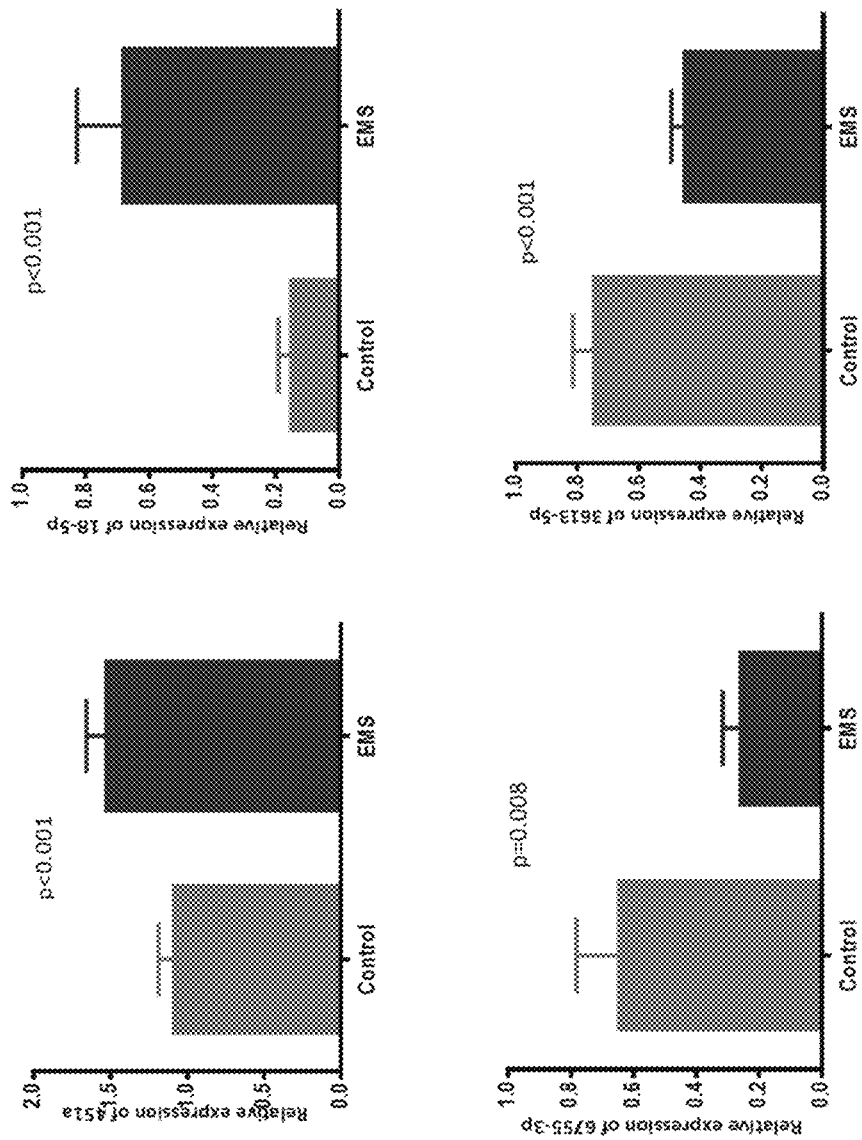

The relative expression of miR-125b-5p, miR-150-5p, miR-342-3p, miR-145-5p, miR-143-3p, miR-500a-3p, miR-451a, miR-18a-5p, miR-6755-3p, miR-3613-5p in the serum of women with and without endometriosis were assessed using real-time quantitative polymerase chain reaction. Expression levels of miR-125b-5p, miR-150-5p, miR-342-3p, miR-145-5p, miR-143-3p, miR-500a-3p, miR-451a, miR-18a-5p were unregulated (p<0.05), while miR-6755-3p and miR-3613-5p levels were downregulated in women with endometriosis (p<0.05) as shown in FIG. 2A and FIG. 2B. The variation of these miRNAs through the menstrual cycle was also determined. In the endometriosis group there were 8 and 16 proliferative and secretory samples, respectively. In the control group there were 13 proliferative and 11 secretory: samples. There was no differential menstrual cyclic stage specific expression of these miRNAs among endometriotic patients (p>0.05).

Assessment of the Diagnostic Value of Circulating miRNAs in Endometriosis

Figure 3A:
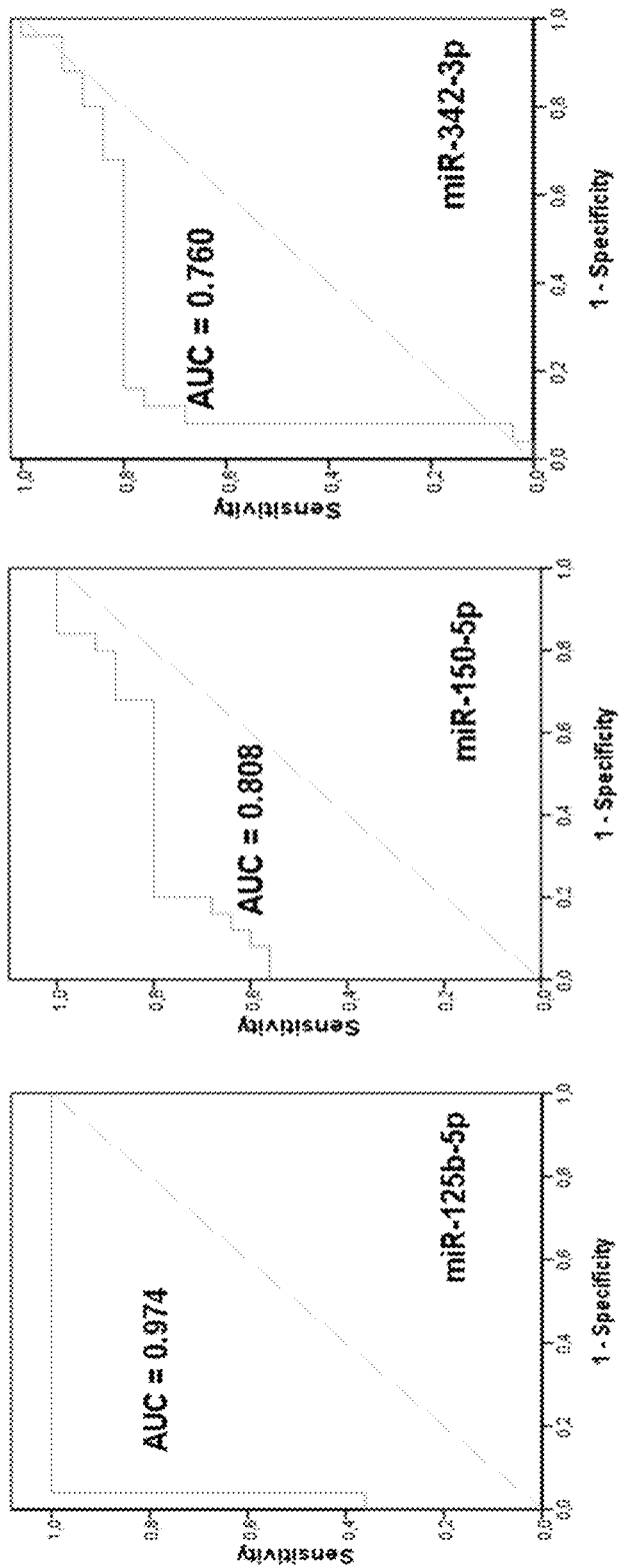
FIG. 3A, is an image illustrating receiver operating characteristic (ROC) curve analysis of serum miR-125b-5p, miR-150-5p, and miR-342-3p.
Figure 3B:
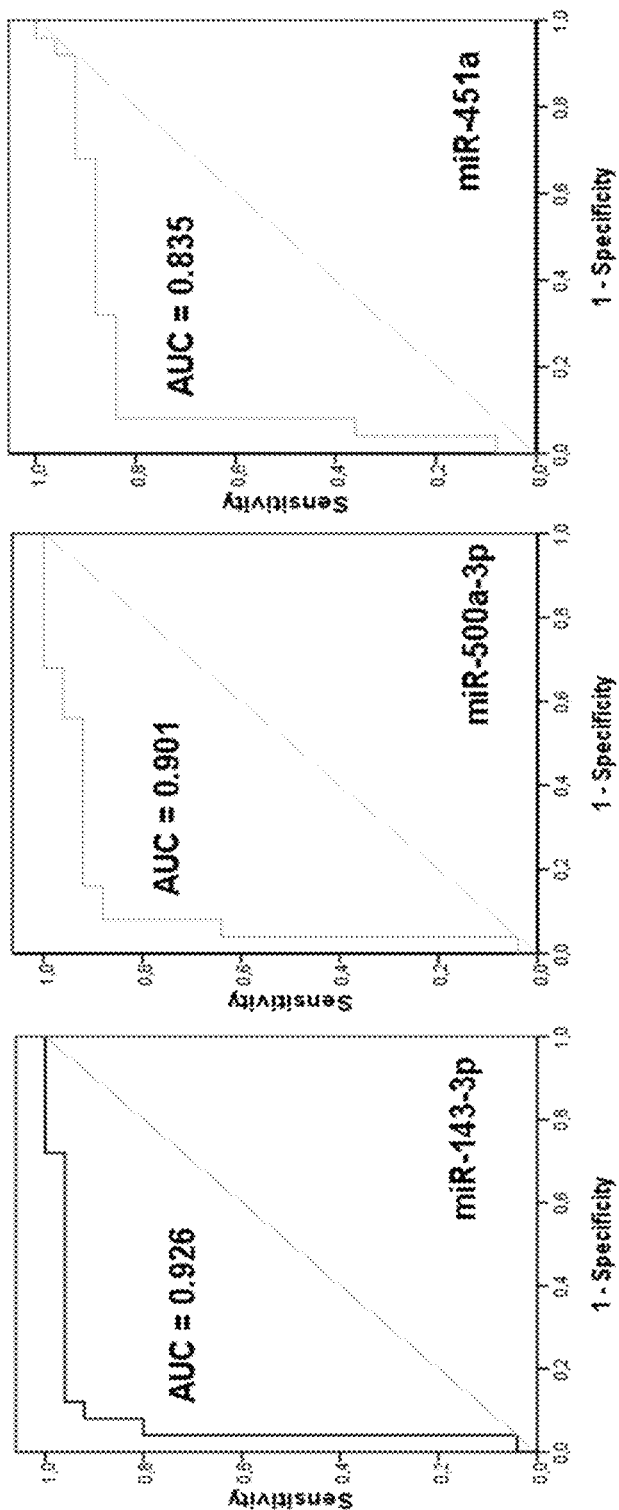
FIG. 3B, is an image illustrating ROC curve analysis of serum miR-451a, miR-500a-3p, miR-143-3p.
Figure 3C:
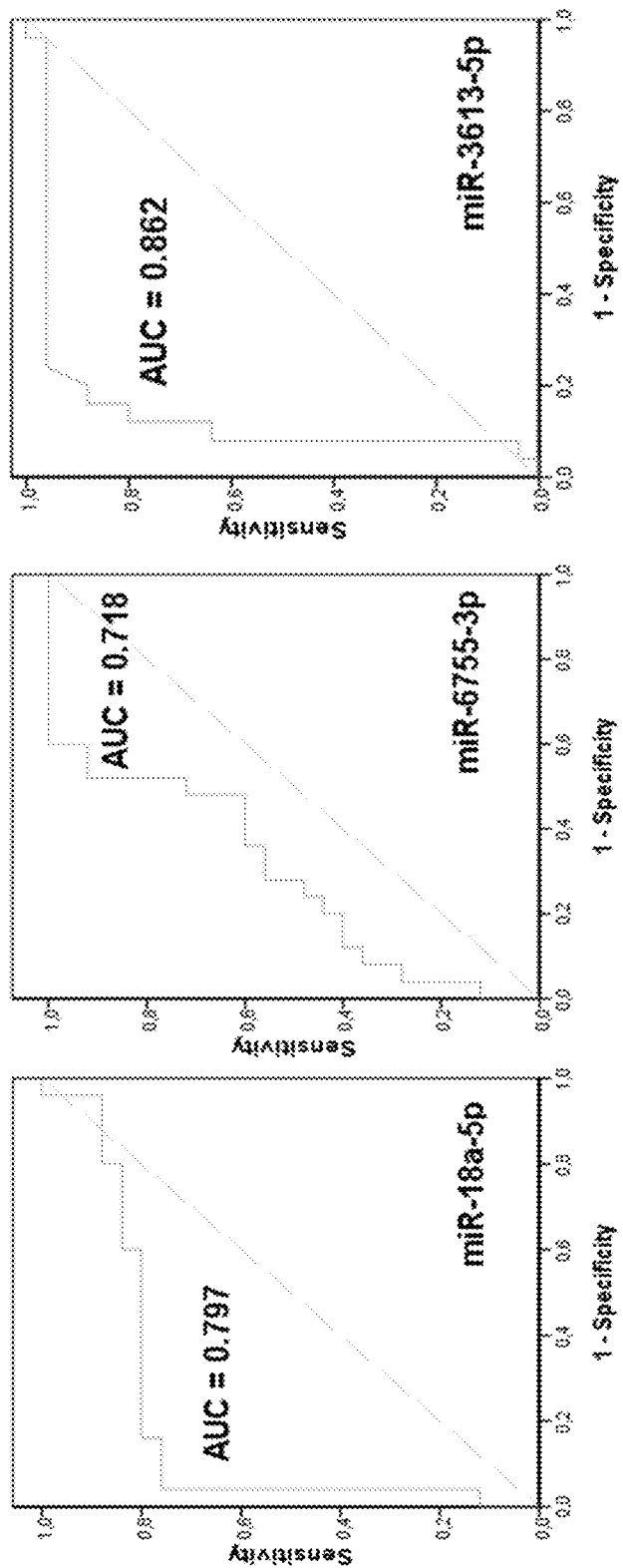
FIG. 3C, is an image illustrating ROC curve analysis of serum miR-18a-5p, miR-6755-3p, and miR-3613-5p. miR-125b-5p (FIG. 3A) showed the highest AUC of 0.974.
Figure 3D:
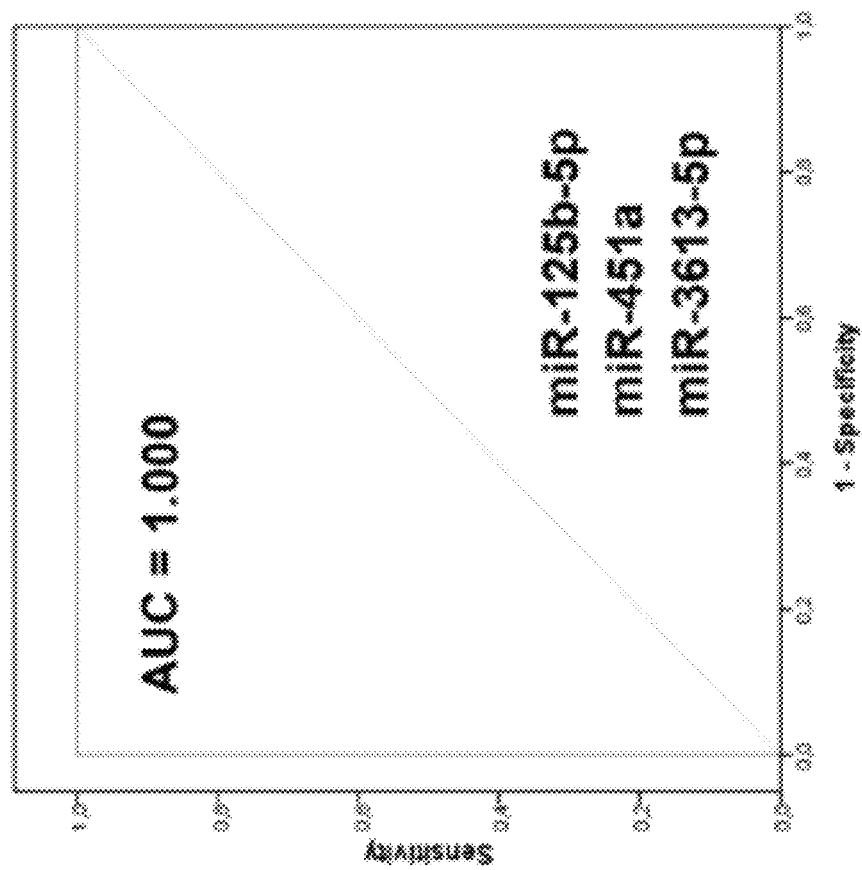
FIG. 3D is a set of images depicting the result of AUC values of the differentially expressed miRNAs.

The ROC curve analysis of serum miRNAs that were differentially expressed between the two groups, was performed. AUC values of the differentially expressed miRNAs are shown in Table 2 and FIG. 3. Among the differentially expressed miRNAs, miR-125b-5p expression levels had the highest AUC (0.974, 95% Confidence Interval [CI], 0.00-1.00, p<0.001), with a sensitivity and specificity of 100% and 96%, respectively, for the cut off value of 0.0688. miRNA expressions in diagnosing endometriosis was improved by applying a logistic regression model to data with disease versus control samples. Since the distributions of all the biomarkers were not skewed normally, the variables were logarithmically transformed (FIGS. 3A-3C). A high AUC was observed for miR-125b-5p alone. A further increase in the AUC to 1.000 was achieved when combining the predictors 125b-5p, 451a and 3613-5p (FIG. 3D). The sensitivity and specificity reached 100% when these three microRNAs were combined. Therefore, the combination of micro RNAs demonstrated improved diagnostic ability over any individual micro RNAs. The following logistic model was selected: miRNA combination=118.406+108.751×log 10(125b-5p)+41.015×log 10(451a)−57.935×log 10(3613-5p). The microarray data shown in Table 3 demonstrates the top miRNA hits and the comparison of endometriosis (E1) upregulation vs. control (C1), E1 downregulation vs. C1.

The Use for microRNAs as Biomarkers for Endometriosis

In this study, the differentially expressed circulating miRNAs as biomarkers for endometriosis, was demonstrated. The results demonstrated that miR-125b-5p expression had the highest AUC levels among the miRNAs identified in the microarray data. Endometriosis is associated with a 6.7 year average diagnostic delay, resulting in progression of the disease and impairment in quality of life (Nnoaham et al., 2011, Fertil Steril, 96:366-373). Early diagnosis of endometriosis would allow prompt treatment, improvement in quality of life and potentially preservation of fertility. Several growth factors and cytokines have been studied in serum, plasma and urine as potential biomarkers of this disease (Cho et al., 2012, Hum Reprod, 27:515-522, Reis et al., 2012, Hum Reprod, 27:1445-1450); however, none of these are sufficiently sensitive or specific to be translated into a clinical diagnostic tool for endometriosis (May et al., 2010, Hum Reprod, 16:651-674).

There is little known about the mechanisms by which miRNAs are transported to plasma and their biological impact on distant organs. Normal endometrium as well as paired eutopic and ectopic endometrium samples have differential miRNA expression patterns (Jia et al., 2013, Hum Reprod, 28:322-330). Furthermore, a strong association between the miRNA profiles of the serum/plasma and tissues has been demonstrated in studies examining several cancers (Resnick et al., 2009, Gynecol Oncol, 112:55-59, Wang et al., 2013, J Clin Endocrinol Metab, 98:281-289). In addition to their role as biomarkers, circulating miRNAs have a regulatory effect on distant tissues. The circulating miRNAs identified here is a means of communication between endometriosis and endometrium. Further, they have systemic effects, altering distant organ systems. It has been demonstrated in an animal model that endometriosis far removed from the peritoneal cavity affects uterine gene expression (Naqvi et al., 2016, Reprod Sci, 23:186-191). Circulating miRNAs is a signaling mechanism by which endometriosis has an effect on the uterus.

It has been demonstrated that miRNAs contribute to the pathogenesis of endometriosis by regulating the abnormal cell differentiation, invasion and inflammation (Petracco et al., 2011, J Clin Endocrinol Metab, 96:E1925-E1933, Teague et al., 2010, Hum Reprod Update, 16:142-165, Naqvi et al., 2016, Reprod Sci, 23:186-191). It has also been demonstrated that many individual circulating miRNAs are identified in endometriosis (Jia et al., 2013, Hum Reprod, 28:322-330, Wang et al., 2013, J Clin Endocrinol Metab, 98:281-289, Cho et al., 2015, Fertil Steril, 103(5):1252-1260). Jia et al. reported that plasma miR-17-5p, miR-20a and miR-22 were down-regulated in women with endometriosis (Jia et al., 2013, Hum Reprod, 28:322-330), however these miRNAs did not reach the cut off threshold and was not examined further in this study. The differences in miRNAs identified are due to the differences in age, race disease severity or use of medical therapies.

In the first comprehensive analysis of all miRNA in the circulation of women with endometriosis it was identified that miR-125b-5p is the best single candidate biomarker of endometriosis. miR-125b-5p was significantly upregulated in serum of women with endometriosis and it had the highest AUC as well as sensitivity and specificity (AUC=0.974, 95% Confidence Interval [CI], 0.00-1.00, p<0.001) (100% and 96% respectively) of any single miRNA. miR-125b-5p has demonstrated a role in invasion and the pathogenesis of cancer and acts as a oncogene in lung cancer (Wang et al., 2015, Mol Med Rep, 11(5):3880-3887). It is upregulated in the serum of breast cancer patients and is associated with chemotherapeutic resistance, nonresponsive patients having higher expression levels (Wang et al., 2012, PLoS One, 7:e34210, Matamala et al., 2015, Clin Chem, 61(8):1098-1106), while significantly higher levels found in the serum of HBV positive hepatocellular carcinoma patients (Giray et al., 2014, Mol Biol Rep, 41(7):4513-4519). It has also been demonstrated that miR-125b-5p regulates osteogenic differentiation of hBMSCs through the modulation of Osx expression (Chen et al., 2014, Mol Med Rep, 9(5):1820-1826). In this study, majority of cases had severe endometriosis with invasion and miRNA 125, which contributes to that phenotype. Other miRNAs found in this study also contribute to the etiology of this disease. miR-451a has tumor suppressing function in neuroblastoma and osteosarcoma (Liu et al., 2016, Mol Med Rep, doi: 10.3892/mmr. 4770, Xu et al., 2014, Cell Biochem Biophys, 69(1):163-168) and elevated levels found in endometriotic tissue that function to limit endometriotic lesion cell survival (Graham et al., 2015, Hum Reprod, 30(3):642-652).

In conclusion, this study showed the differential expression of circulating miRNAs, particularly miR-125b-5p, in endometriosis. The findings also support the clinical utility of plasma miRNA profiling in the diagnosis of this disease. Given the lack of biomarkers of disease and the delay in diagnosis, miRNA is useful in early detection and intervention. Further, the role of circulating miRNAs provides a better understanding of the systemic effects of endometriosis and allow for more novel treatments.

TABLE 2

AUC, 95% Confidence Interval (CI) and P values of the differentially expressed miRNAs

| miRNAs | AUC | 95% CI | p-value |
| --- | --- | --- | --- |
| miR-125b-5p | 0.974 | 0.000-1.000 | <0.001 |
| miR-150-5p | 0.808 | 0.680-0.936 | <0.001 |
| miR-342-3p | 0.760 | 0.608-0.912 | 0.002 |
| miR-143-3p | 0.926 | 0.000-1.000 | <0.001 |
| miR-500a-3p | 0.901 | 0.803-0.998 | <0.001 |
| miR-451a | 0.835 | 0.707-0.963 | <0.001 |
| miR-18a-5p | 0.797 | 0.653-0.940 | 0.001 |
| miR-6755-3p | 0.718 | 0.577-0.860 | 0.008 |
| miR-3613-5p | 0.862 | 0.740-0.985 | <0.001 |

TABLE 3

Top Hits Microarray Data

| | |
| --- | --- |
| miR-125b-5p | 77.07 E1 up vs C1 |
| miR-214-3p | 62.5954 E1 up vs C1 |
| miR-150-5p | 57.2203 E1 up vs C1 |
| miR-342-3p | 41.5546 E1 up vs C1 |
| miR-145-5p | 38.1178 E1 up vs C1 |
| miR-143-3p | 29.4994 E1 up vs C1 |
| miR-126-3p | 27.3483 E1 up vs C1 |
| miR-500a-3p | 18.0946 E1 up vs C1 |
| miR-451a | 16.8822 E1 up vs C1 |
| miR-18a-5p | 14.4632 E1 up vs C1 |
| miR-6755-3p | -12.4883 E1 down vs C1 |
| miR-553 | -18.6982 E1 down vs C1 |
| miR-3613-5p | -102.613 E1 down vs C1 |
| miR-4668-3p | -124.901 E1 down vs C1 |

Example 2: Relative Expression of miRNAs in Endometriosis Lesions in Baboons

Figure 4:
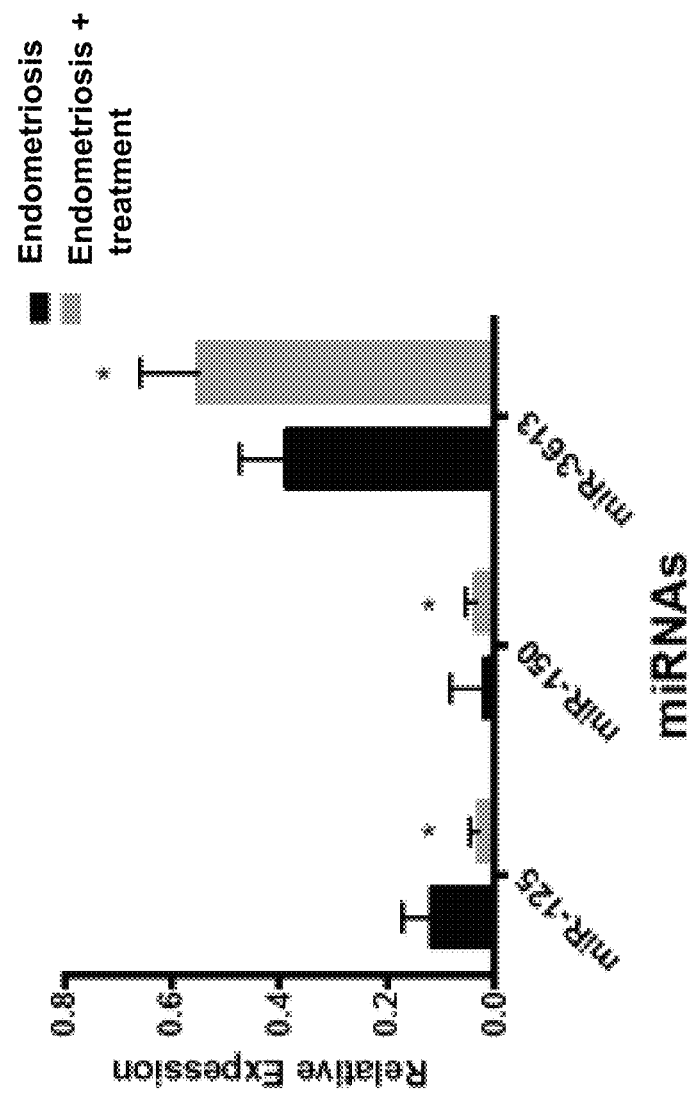
FIG. 4 is an image depicting the result of relative expression of miRNAs in endometriosis and groups with treatment in baboons as determined by real time quantitative PCR. p-values based on analysis using the Mann-Whitney U test.

The relative expression of miRNAs in endometriotic lesions in Baboons as determined by real time quantitative PCR as shown in FIG. 4. The comparison of the relative expression levels of miR-125b-5p, miR-150-5p and miR-3613-5p with the relative expression levels of the respective miRNAs after statin treatment was performed. It was observed that the lesions shrunk in the statin treated animals. The miR-125b-5p expression levels in samples of untreated animals were shown to have higher relative expression levels than samples that were taken from treated animals. Further, it was observed that the relative level of miR-3613-5p was lower in samples from control untreated animals in comparison to the level of miR-3613-5p in samples from treated animals. Lastly, it was observed that the relative level of miR-150-5p was lower in samples from control untreated animals, in comparison to the level of miR-150-5p in samples from treated animals.

Example 3: Saliva MicroRNAs as Diagnostic Markers for Endometriosis

Step 1: RNA Extraction from Saliva

Saliva samples (200 µL) were collected and transferred to 1.5 mL tubes. RNase free water was added to samples with volumes less than 200 µL in order to bring the total sample volume to 200 µL. 1 mL of QIAzol Lysis Reagent (Qiagen) was added to the sample. The tube was vortexed briefly, and the sample was allowed to incubate at room temperature for five minutes. Then, 200 µL of choloroform was added to the lysate and vortexed for approximately 15 seconds. The sample mixture was then incubated for two minutes at room temperature and centrifuged at 12,000×g for fifteen minutes in a cold room (approximately 4° C.). Approximately 560 µL of the aqueous phase was transferred to a new 1.5 mL tube. 840 µL of 100% ethanol was added to the 560 µL of aqueous phase to obtain a total volume of 1400 µL. 700 µL of the mixture was then transferred into a RNeasy MiniElute spin column with 2 mL collection tube. The spin column with collection tube was centrifuged at 9,000×g for 15 seconds. The flow-through was discarded and the remaining 700 µL of mixture was transferred to the spin column with collection tube and again centrifuged at 9,000×g for 15 seconds. The flow-through was discarded and 700 µL of buffer RWT was added to each spin column and then centrifuged at 9,000×g for 15 seconds. The flow-through was discarded and 500 µL of buffer RPE was added to each spin column and then centrifuged at 9,000×g for 15 seconds. The flow-through was discarded and another 500 µL of buffer RPE was added to the spin column and again centrifuged at 9,000×g for 15 seconds. Then, 500 µL of 80% ethanol was added to the spin column and centrifuged at 9,000×g for 2 minutes. The flow-through and collection tube were subsequently discarded and the spin column was transferred to a new 2 mL collection tube. The lid of the spin column was left open and then centrifuged at 12,000×g for 5 minutes to dry the membrane. The spin column was then placed in a 1.5 mL tube. 14 µL of RNase-free water was added to the spin column and it was centrifuged at 12,000×g for 1 minute to elute total RNA. The spin column was discarded and the RNA was stored at −80° C.

Step 2: Preparation of cDNA

The TaqMan Advanced miRNA cDNA Synthesis Kit was used to prepare cDNA (ThermoFisher, catalog number: A28007) in four sequential steps: A, B, C, and D.

Step A was performed with the following contents in each reaction: 0.5 µL 10× Poly A buffer; 0.5 µL 10 mM ATP; 0.3 µL Poly A enzyme, 5 U/µL; 1.7 µL RNase-free water; 2.0 µL sample. The plate or tube was sealed and vortexed briefly. The plate or tube was centrifuged to spin down the contents and eliminate any air bubbles. The plate or tube was placed into a thermal cycler and incubated with the following settings:
1. Polyadenylation at 37° C. for 45 minutes.
2. Stop reaction at 65° C. for 10 minutes.
3. Hold at 4° C.

Step B was performed with the following contents in each reaction: 3.0 µL 5×DNA Ligase Buffer; 4.5 µL 50% PEG 8000; 0.6 µL 25× Ligation Adaptor; 1.5 µL RNA Ligase; 0.4 µL RNase-free water. The Ligation Reaction Mix was vortexed to thoroughly mix the contents and then centrifuged briefly to spin down the contents and eliminate air bubbles. 10 µL of the Ligation Reaction Mix was transferred to each well of the reaction plate or each reaction tube containing the poly(A) tailing reaction product. The reaction plate or tubes were sealed, then vortexed briefly or shaken (1,900 RPM for 1 minute with an Eppendorf™ MixMate™) to thoroughly mix the contents. The reaction plate or tubes were centrifuged to spin down the contents. The plate or tube was placed into the thermal cycler.

Step C was performed with the following contents in each reaction: 6 µL 5×RT Buffer; 1.2 µL dNTP Mix (25 mM each); 1.5 µL 20× Universal RT Primer; 3 µL 10×RT Enzyme Mix; 3.3 µL RNase-free water. The RT Reaction Mix was vortexed to thoroughly mix the contents, then centrifuged briefly to spin down the contents and eliminate air bubbles. 15 µl of the RT Reaction Mix was transferred to each well of the reaction plate or each reaction tube containing the adaptor ligation reaction product. The total volume was 30 µl per well or tube. The reaction plate or tubes were then sealed and vortexed briefly to thoroughly mix the contents. The reaction plate or tubes were then centrifuged briefly to spin down the contents. The plate or tube was placed in the thermal cycler and incubated with the following settings:
1. Reverse transcription at 42° C. for 15 minutes
2. Stop reaction at 85° C. for 5 minutes
3. Hold at 4° C.

Step D was performed with the following contents in each reaction: 25 µL 2×miR-Amp Master Mix; 2.5 µL 20×miR-Amp Primer Mix; 17.5 µL RNase-free water. The miR-Amp Reaction Mix was vortexed to thoroughly mix the contents, then centrifuged briefly to spin down the contents and eliminate air bubbles. 45 µL of the miR-Amp Reaction Mix was transferred to each well of a new reaction plate or reaction tube. 5 µL of the RT reaction product was added to each reaction well or reaction tube. The total volume in each well or tube was 50 µL. The reaction plate or tubes were sealed and then vortexed briefly to thoroughly mix the contents. The reaction plate or tubes were then briefly centrifuged to spin down to mix the contents. The reaction plate or tubes were placed into a thermal cycler and then incubated using the following settings, MAX ramp speed, and standard cycling:
1. Enzyme activation at 95° C. for 5 minutes, 1 cycle
2. Denature at 95° C. for 3 seconds, 14 cycles
3. Anneal/Extend at 60° C. for 30 seconds, 14 cycles
4. Stop reaction at 99° C. for 10 minutes, 1 cycle
5. Hold at 4° C.

Step 3: Amplification of microRNAs
RT-PCR Protocol:
1. 95° C. for 3 min
2. 95° C. for 15 s
3. 59° C. for 5 s
4. 72° C. for 55 s
5. Repeat 2-4 steps for 39 cycles
6. Melting Curve at 55° C. for 10 s
7. 95° C. for 5 s
8. Hold at 4° C.

Figure 5:
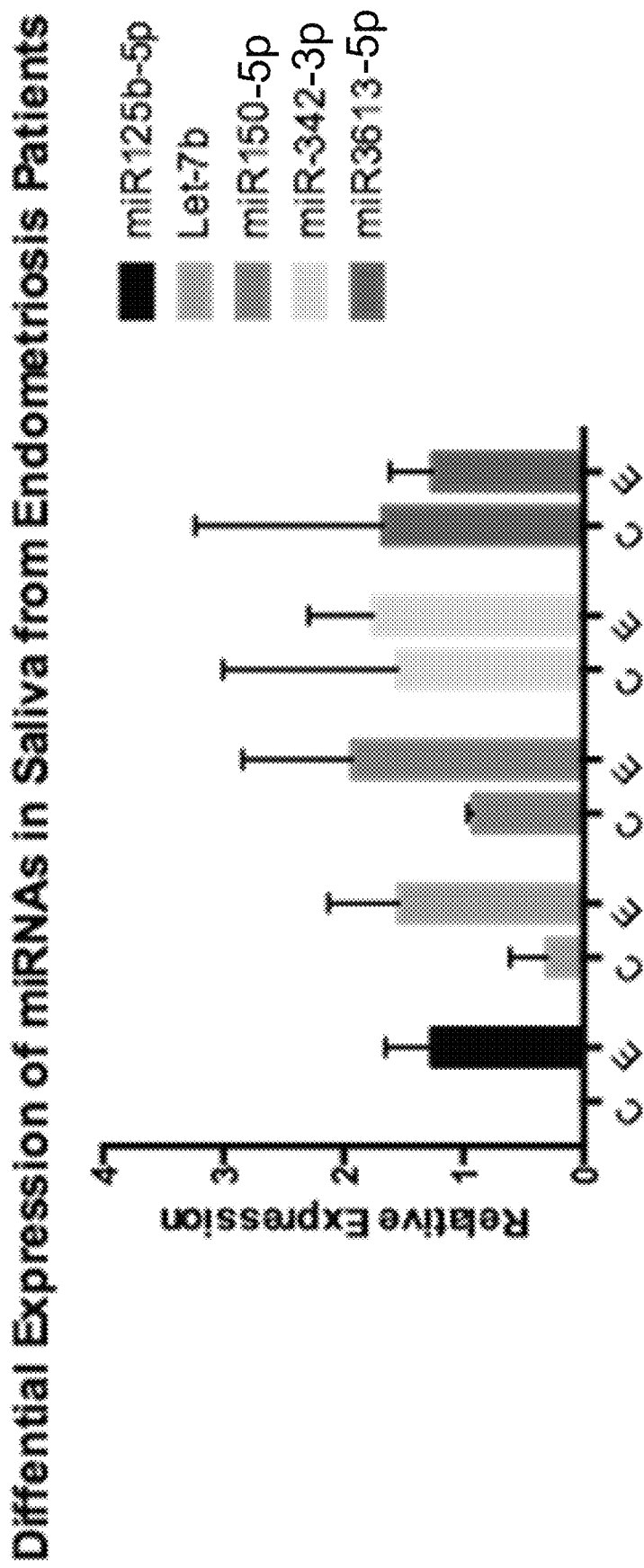
FIG. 5 is an image depicting the result of relative expression of miRNAs in saliva in endometriosis and control groups.
Figure 6:
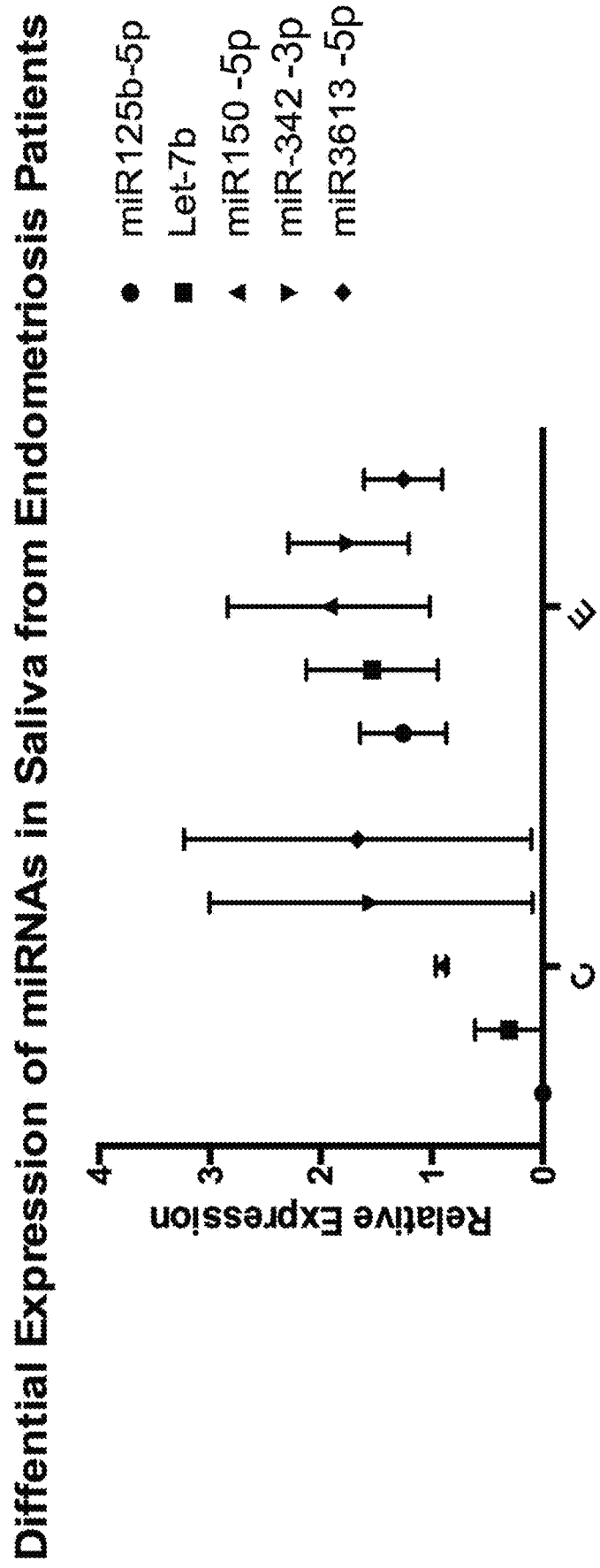
FIG. 6 is an image depicting the result of relative expression of miRNAs in saliva in endometriosis and control groups.

The relative expression of saliva miRNAs that were differentially expressed between the control group and the endometriosis group are shown in FIG. 5 and FIG. 6. The data represents fifteen samples in each group. The fold change for miR 125b-5p, Let7b and miR150-5p are 25, 7 and 1.8 fold respectively. These fold changes are statistically significant when comparing the endometriosis group to the control group as the p-value is less than 0.05 ($p<0.05$) for the above miRs. The p-values are as follows: miR 125b-5p ($p<0.001$), Let7b ($p<0.025$) and miR 150-5p ($p<0.047$). A statistically-significant downregulation of miR-3613-5p was observed.

Example 4: Serum MicroRNAs Used to Diagnose Endometriosis Prior to Surgical Diagnosis Reproductive age women undergoing laparoscopy or laparotomy for benign gynecologic indication were enrolled in a prospective case control study. Patients were stratified into the disease group if surgery confirmed presence of endometriosis, and control if surgery revealed other benign pathology. Twenty-three control patients and seventeen endometriosis patients were enrolled and met inclusion criteria in the study. Controls included 4 patients with dermoid cysts, 3 with cystadenomas, 6 with fibroids, 2 with evidence of chronic pelvic infection, and 8 without abnormal pathology. Expression levels of microRNAs 125b and 150 were significantly higher in patients with endometriosis compared to control (microRNA 125: X vs Y; p=0.028, MicroRNA 150: Z vs W; p=0.014, respectively). 4 patients with pelvic pain and suspected endometriosis were not found to have endometriosis on surgical evaluation. Expression of 125b and 150 in these patients was consistent with that of controls, and differed from that of patients with surgically confirmed endometriosis.

Figure 7:
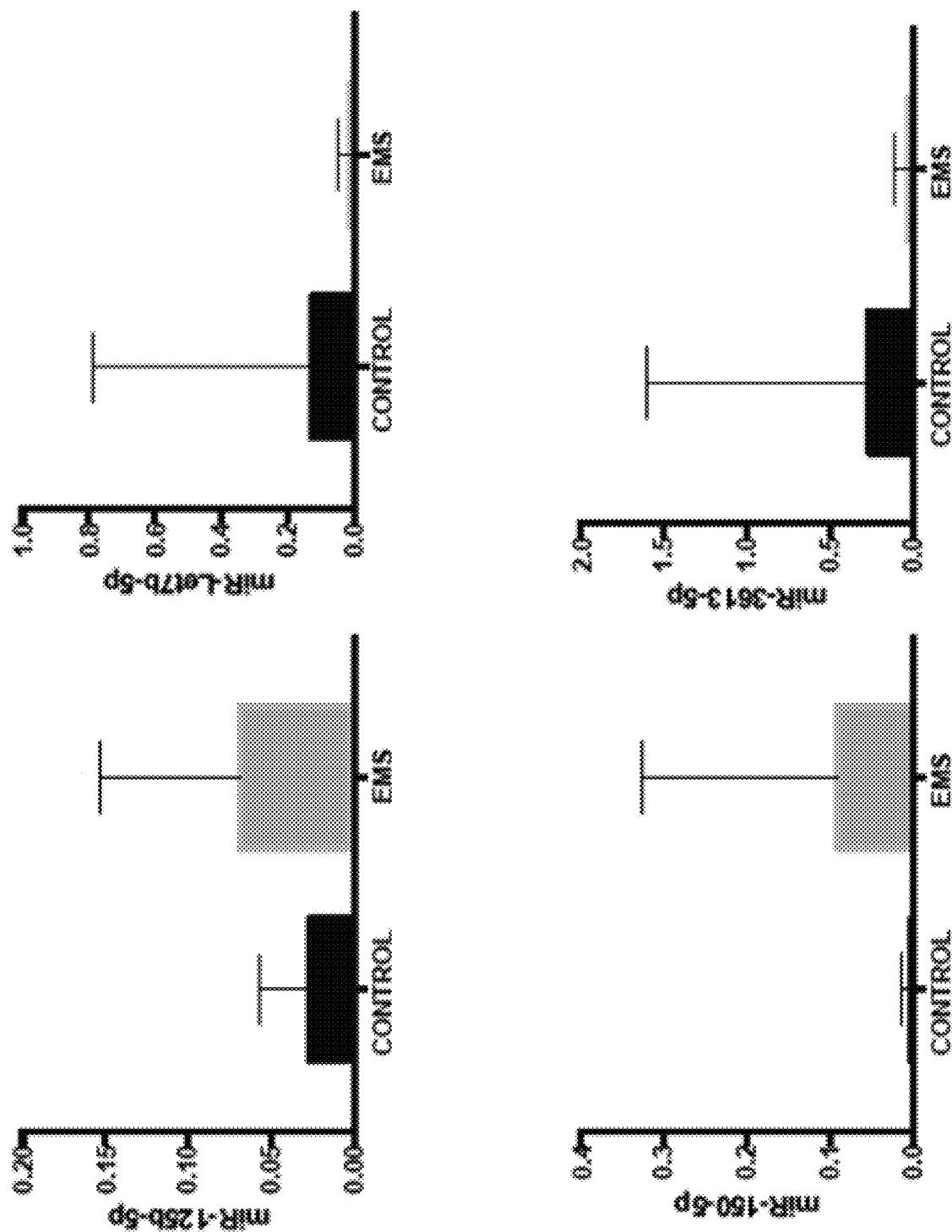
FIG. 7 is an image depicting expression levels of miRNA in serum of women who underwent laparoscopy or laparotomy that either confirmed presence of endometriosis (disease group) or revealed other benign pathology (control group).

Total microRNA was extracted from serum using a miRNeasy mini kit, (Qiagen) following manufacturer's protocol. Preparation of cDNA was performed using TaqMan Advanced miRNA cDNA Synthesis Kit (ThermoFisher). Quantitative Real-Time Polymerase Chain Reaction (qRT-PCR) was carried out to determine the expression levels of microRNAs 125b-5p and 150-5p. The expression levels of the serum microRNAs between the control and endometriosis group were compared using the Mann-Whitney U test. Results of the study (FIG. 7) showed that microRNAs 125b-5p and 150-5p were significantly elevated in patients with endometriosis compared to controls.

Example 5: Diagnosis and Treatment of Endometriosis

In this prophetic example, a blood or saliva sample is taken from a female patient with symptoms of endometriosis. The quantity of microRNA 125b-5p is then determined in the sample, and the patient is diagnosed with endometriosis if the quantity is above a threshold value. The patient is treated with a therapeutically effective dose of a compound. The compound is given to the patient by oral, intravenous, or intramuscular administration. The compound causes a reduction in the symptoms of endometriosis. The patient is treated about once every month. After one month of treatment, six months of treatment, and one year of treatment, the patient is assessed for reduction in symptoms of endometriosis.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the disclosure described herein may be employed in practicing the invention. It is intended that the following claims define the scope of the invention and that methods and structures within the scope of these claims and their equivalents be covered thereby.

What is claimed is:

1. A method of treating endometriosis in a subject, the method comprising:
   (I) determining that the subject has endometriosis by:
   (a) providing a blood, serum, or plasma sample comprising nucleic acids from the subject;
   (b) obtaining a detected level of at least one miRNA, wherein the level of the at least one miRNA is determined by performing an amplification reaction on at least one miRNA selected from the group consisting of: miR-125b, miR143, miR-145, miR-150, miR-342, miR-451, miR-3613, miR-500, miR-18, miR-214, miR-126, miR-553, miR-4668, and miR-6755;
   (c) detecting endometriosis in the subject based on the level of the at least one miRNA; and
   (II) administering a treatment for the endometriosis to the subject, thereby treating the endometriosis.

2. The method of claim 1, wherein the blood, serum, or plasma sample is a serum sample.

3. The method of claim 1, wherein the at least one miRNA is a circulating, cell-free miRNA.

4. The method of claim 1, wherein the treatment is selected from the group consisting of: a non-steroidal anti-inflammatory drug, a hormone therapy, a hormonal contraceptive, surgical laparoscopy, chemotherapy, and immunotherapy.

5. The method of claim 1, wherein the treatment is surgical laparotomy.

6. The method of claim 1, wherein the treatment is selected from the group consisting of: a gonadotropin-releasing hormone agonist, a progestin, an oral contraceptive, an aromatase inhibitor, and a statin.

7. The method of claim 1, wherein the at least one miRNA comprises at least two miRNAs selected from the group consisting of: miR-125b, miR-150, miR-342, miR-451a, miR-3613, and let-7b.

8. The method of claim 1, wherein the at least one miRNA comprises at least four miRNAs selected from the group consisting of: miR-125b, miR-150, miR-342, miR-451a, miR-3613, and let-7b.

9. The method of claim 1, wherein the at least one miRNA comprises miR-342.

10. The method of claim 1, wherein the at least one miRNA comprises miR-451a.

11. The method of claim 1, wherein the at least one miRNA comprises miR-125b.

12. The method of claim 1, wherein the at least one miRNA comprises miR-150.

13. The method of claim 1, wherein the at least one miRNA comprises miR-3613.

14. The method of claim 1, wherein the endometriosis is detected with a sensitivity of at least 80%.

15. The method of claim 1, wherein the at least one miRNA is selected from the group consisting of: miR-125b, miR-150, miR-342, and miR-451a, and is at least 20% up-regulated in the blood, plasma, or serum sample compared with a control.

16. The method of claim 1, wherein the level of miR-3613 is at least 20% down-regulated in the blood, plasma or serum sample compared with a control.

* * * * *

```
                      SEQUENCE LISTING

<160> NUMBER OF SEQ ID NOS: 51

<210> SEQ ID NO 1
<211> LENGTH: 23
<212> TYPE: RNA
<213> ORGANISM: Homo sapiens

<400> SEQUENCE: 1
acugcccuaa gugcuccuuc ugg                                              23

<210> SEQ ID NO 2
<211> LENGTH: 23
<212> TYPE: RNA
<213> ORGANISM: Homo sapiens

<400> SEQUENCE: 2
uaaggugcau cuagugcaga uag                                              23

<210> SEQ ID NO 3
<211> LENGTH: 22
<212> TYPE: RNA
<213> ORGANISM: Homo sapiens

<400> SEQUENCE: 3
ugcccuaaau gccccuucug gc                                               22

<210> SEQ ID NO 4
<211> LENGTH: 23
<212> TYPE: RNA
<213> ORGANISM: Homo sapiens

<400> SEQUENCE: 4
uaaggugcau cuagugcagu uag                                              23

<210> SEQ ID NO 5
<211> LENGTH: 22
<212> TYPE: RNA
<213> ORGANISM: Homo sapiens
```

```
<400> SEQUENCE: 5
acaggugagg uucuugggag cc                                          22

<210> SEQ ID NO 6
<211> LENGTH: 24
<212> TYPE: RNA
<213> ORGANISM: Homo sapiens

<400> SEQUENCE: 6
ucccugagac ccuuuaaccu guga                                        24

<210> SEQ ID NO 7
<211> LENGTH: 22
<212> TYPE: RNA
<213> ORGANISM: Homo sapiens

<400> SEQUENCE: 7
acggguuagg cucuugggag cu                                          22

<210> SEQ ID NO 8
<211> LENGTH: 22
<212> TYPE: RNA
<213> ORGANISM: Homo sapiens

<400> SEQUENCE: 8
ucacaaguca ggcucuuggg ac                                          22

<210> SEQ ID NO 9
<211> LENGTH: 22
<212> TYPE: RNA
<213> ORGANISM: Homo sapiens

<400> SEQUENCE: 9
ucccugagac ccuaacuugu ga                                          22

<210> SEQ ID NO 10
<211> LENGTH: 22
<212> TYPE: RNA
<213> ORGANISM: Homo sapiens

<400> SEQUENCE: 10
ucguaccgug aguaauaaug cg                                          22

<210> SEQ ID NO 11
<211> LENGTH: 21
<212> TYPE: RNA
<213> ORGANISM: Homo sapiens

<400> SEQUENCE: 11
cauuauuacu uuugguacgc g                                           21

<210> SEQ ID NO 12
<211> LENGTH: 21
<212> TYPE: RNA
<213> ORGANISM: Homo sapiens

<400> SEQUENCE: 12
ugagaugaag cacguagcu c                                            21

<210> SEQ ID NO 13
<211> LENGTH: 22
<212> TYPE: RNA
<213> ORGANISM: Homo sapiens
```

<400> SEQUENCE: 13
ggugcagugc ugcaucucug gu                                                   22

<210> SEQ ID NO 14
<211> LENGTH: 22
<212> TYPE: RNA
<213> ORGANISM: Homo sapiens

<400> SEQUENCE: 14
ggauuccugg aaauacuguu cu                                                   22

<210> SEQ ID NO 15
<211> LENGTH: 23
<212> TYPE: RNA
<213> ORGANISM: Homo sapiens

<400> SEQUENCE: 15
guccaguuuu cccaggaauc ccu                                                  23

<210> SEQ ID NO 16
<211> LENGTH: 22
<212> TYPE: RNA
<213> ORGANISM: Homo sapiens

<400> SEQUENCE: 16
cugguacagg ccuggggac ag                                                    22

<210> SEQ ID NO 17
<211> LENGTH: 22
<212> TYPE: RNA
<213> ORGANISM: Homo sapiens

<400> SEQUENCE: 17
ucucccaacc cuuguaccag ug                                                   22

<210> SEQ ID NO 18
<211> LENGTH: 22
<212> TYPE: RNA
<213> ORGANISM: Homo sapiens

<400> SEQUENCE: 18
acagcaggca cagacaggca gu                                                   22

<210> SEQ ID NO 19
<211> LENGTH: 22
<212> TYPE: RNA
<213> ORGANISM: Homo sapiens

<400> SEQUENCE: 19
ugccugucua cacuugcugu gc                                                   22

<210> SEQ ID NO 20
<211> LENGTH: 23
<212> TYPE: RNA
<213> ORGANISM: Homo sapiens

<400> SEQUENCE: 20
ucucacacag aaaucgcacc cgu                                                  23

<210> SEQ ID NO 21
<211> LENGTH: 21
<212> TYPE: RNA

```
<213> ORGANISM: Homo sapiens

<400> SEQUENCE: 21
aggggugcua ucugugauug a                                            21

<210> SEQ ID NO 22
<211> LENGTH: 22
<212> TYPE: RNA
<213> ORGANISM: Homo sapiens

<400> SEQUENCE: 22
aaaccguuac cauuacugag uu                                           22

<210> SEQ ID NO 23
<211> LENGTH: 22
<212> TYPE: RNA
<213> ORGANISM: Homo sapiens

<400> SEQUENCE: 23
uagcaagaga accauuacca uu                                           22

<210> SEQ ID NO 24
<211> LENGTH: 22
<212> TYPE: RNA
<213> ORGANISM: Homo sapiens

<400> SEQUENCE: 24
augcaccugg gcaaggauuc ug                                           22

<210> SEQ ID NO 25
<211> LENGTH: 23
<212> TYPE: RNA
<213> ORGANISM: Homo sapiens

<400> SEQUENCE: 25
uaauccuugc uaccugggug aga                                          23

<210> SEQ ID NO 26
<211> LENGTH: 20
<212> TYPE: RNA
<213> ORGANISM: Homo sapiens

<400> SEQUENCE: 26
gcacccaggc aaggauucug                                              20

<210> SEQ ID NO 27
<211> LENGTH: 18
<212> TYPE: RNA
<213> ORGANISM: Homo sapiens

<400> SEQUENCE: 27
aauccuugcu accugggu                                                18

<210> SEQ ID NO 28
<211> LENGTH: 21
<212> TYPE: RNA
<213> ORGANISM: Homo sapiens

<400> SEQUENCE: 28
aaaacgguga gauuuuguuu u                                            21

<210> SEQ ID NO 29
<211> LENGTH: 24
```

-continued

```
<212> TYPE: RNA
<213> ORGANISM: Homo sapiens

<400> SEQUENCE: 29
acaaaaaaaa aagcccaacc cuuc                                          24

<210> SEQ ID NO 30
<211> LENGTH: 22
<212> TYPE: RNA
<213> ORGANISM: Homo sapiens

<400> SEQUENCE: 30
uguuguacuu uuuuuuugu uc                                             22

<210> SEQ ID NO 31
<211> LENGTH: 23
<212> TYPE: RNA
<213> ORGANISM: Homo sapiens

<400> SEQUENCE: 31
gaaaauccuu uuuguuuuc cag                                            23

<210> SEQ ID NO 32
<211> LENGTH: 23
<212> TYPE: RNA
<213> ORGANISM: Homo sapiens

<400> SEQUENCE: 32
agggaaaaaa aaaaggauuu guc                                           23

<210> SEQ ID NO 33
<211> LENGTH: 22
<212> TYPE: RNA
<213> ORGANISM: Homo sapiens

<400> SEQUENCE: 33
uguugucaug uuuuuucccu ag                                            22

<210> SEQ ID NO 34
<211> LENGTH: 22
<212> TYPE: RNA
<213> ORGANISM: Homo sapiens

<400> SEQUENCE: 34 uagguagac acugacaacg uu                                             22

<210> SEQ ID NO 35
<211> LENGTH: 22
<212> TYPE: RNA
<213> ORGANISM: Homo sapiens

<400> SEQUENCE: 35
cuauacaacc uacugccuuc cc                                            22

<210> SEQ ID NO 36
<211> LENGTH: 22
<212> TYPE: RNA
<213> ORGANISM: Homo sapiens

<400> SEQUENCE: 36
ugagguagua gguugugugg uu                                            22

<210> SEQ ID NO 37
```

<211> LENGTH: 22
<212> TYPE: RNA
<213> ORGANISM: Artificial Sequence
<220> FEATURE:
<223> OTHER INFORMATION: chemically synthesized

<400> SEQUENCE: 37
ucccugagac ccuaacuugu ga                                        22

<210> SEQ ID NO 38
<211> LENGTH: 22
<212> TYPE: RNA
<213> ORGANISM: Artificial Sequence
<220> FEATURE:
<223> OTHER INFORMATION: chemically synthesized

<400> SEQUENCE: 38
ucucccaacc cuuguaccag ug                                        22

<210> SEQ ID NO 39
<211> LENGTH: 23
<212> TYPE: RNA
<213> ORGANISM: Artificial Sequence
<220> FEATURE:
<223> OTHER INFORMATION: chemically synthesized

<400> SEQUENCE: 39
ucucacacag aaaucgcacc cgu                                       23

<210> SEQ ID NO 40
<211> LENGTH: 23
<212> TYPE: RNA
<213> ORGANISM: Artificial Sequence
<220> FEATURE:
<223> OTHER INFORMATION: chemically synthesized

<400> SEQUENCE: 40
guccaguuuu cccaggaauc ccu                                       23

<210> SEQ ID NO 41
<211> LENGTH: 21
<212> TYPE: RNA
<213> ORGANISM: Artificial Sequence
<220> FEATURE:
<223> OTHER INFORMATION: chemically synthesized

<400> SEQUENCE: 41
ugagaugaag cacuguagcu c                                         21

<210> SEQ ID NO 42
<211> LENGTH: 22
<212> TYPE: RNA
<213> ORGANISM: Artificial Sequence
<220> FEATURE:
<223> OTHER INFORMATION: chemically synthesized

<400> SEQUENCE: 42
augcaccugg gcaaggauuc ug                                        22

<210> SEQ ID NO 43
<211> LENGTH: 22
<212> TYPE: RNA
<213> ORGANISM: Artificial Sequence
<220> FEATURE:
<223> OTHER INFORMATION: chemically synthesized

```
<400> SEQUENCE: 43
aaaccguuac cauuacugag uu                                              22

<210> SEQ ID NO 44
<211> LENGTH: 23
<212> TYPE: RNA
<213> ORGANISM: Artificial Sequence
<220> FEATURE:
<223> OTHER INFORMATION: chemically synthesized

<400> SEQUENCE: 44
uaaggugcau cuagugcaga uag                                             23

<210> SEQ ID NO 45
<211> LENGTH: 22
<212> TYPE: RNA
<213> ORGANISM: Artificial Sequence
<220> FEATURE:
<223> OTHER INFORMATION: chemically synthesized

<400> SEQUENCE: 45
uguugucaug uuuuuucccu ag                                              22

<210> SEQ ID NO 46
<211> LENGTH: 22
<212> TYPE: RNA
<213> ORGANISM: Artificial Sequence
<220> FEATURE:
<223> OTHER INFORMATION: chemically synthesized

<400> SEQUENCE: 46
uguuguacuu uuuuuuugu uc                                               22

<210> SEQ ID NO 47
<211> LENGTH: 21
<212> TYPE: RNA
<213> ORGANISM: Artificial Sequence
<220> FEATURE:
<223> OTHER INFORMATION: chemically synthesized

<400> SEQUENCE: 47
aaaacgguga gauuuuguuu u                                               21

<210> SEQ ID NO 48
<211> LENGTH: 23
<212> TYPE: RNA
<213> ORGANISM: Artificial Sequence
<220> FEATURE:
<223> OTHER INFORMATION: chemically synthesized

<400> SEQUENCE: 48
gaaaauccuu uuuguuuuc cag                                              23

<210> SEQ ID NO 49
<211> LENGTH: 22
<212> TYPE: RNA
<213> ORGANISM: Artificial Sequence
<220> FEATURE:
<223> OTHER INFORMATION: chemically synthesized

<400> SEQUENCE: 49
acagcaggca cagacaggca gu                                              22

<210> SEQ ID NO 50
```

```
<211> LENGTH: 22
<212> TYPE: RNA
<213> ORGANISM: Artificial Sequence
<220> FEATURE:
<223> OTHER INFORMATION: chemically synthesized

<400> SEQUENCE: 50
ucguaccgug aguaauaaug cg                                          22

<210> SEQ ID NO 51
<211> LENGTH: 17
<212> TYPE: DNA
<213> ORGANISM: Artificial Sequence
<220> FEATURE:
<223> OTHER INFORMATION: chemically synthesized

<400> SEQUENCE: 51
ctcgcttcgg cagcaca                                                17
```